United States Patent
Sajda et al.

(10) Patent No.: US 12,125,593 B2
(45) Date of Patent: Oct. 22, 2024

(54) SYSTEMS AND METHODS FOR FUSING EEG AND fMRI THROUGH HIERARCHICAL DEEP TRANSCODING

(71) Applicant: THE TRUSTEES OF COLUMBIA UNIVERSITY IN THE CITY OF NEW YORK, New York, NY (US)

(72) Inventors: Paul Sajda, New York, NY (US); Xueqing Liu, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 336 days.

(21) Appl. No.: 17/494,562

(22) Filed: Oct. 5, 2021

(65) Prior Publication Data

US 2022/0215955 A1 Jul. 7, 2022

Related U.S. Application Data

(60) Provisional application No. 63/087,806, filed on Oct. 5, 2020.

(51) Int. Cl.
  *G16H 50/20* (2018.01)
  *G06T 7/00* (2017.01)
  *G06T 9/00* (2006.01)
(52) U.S. Cl.
  CPC .......... *G16H 50/20* (2018.01); *G06T 7/0012* (2013.01); *G06T 9/002* (2013.01); *G06T 2207/10088* (2013.01)

(58) Field of Classification Search
  None
  See application file for complete search history.

(56) References Cited

U.S. PATENT DOCUMENTS

| | | | |
|---|---|---|---|
| 5,445,162 A | 8/1995 | Ives | |
| 7,286,871 B2 | 10/2007 | Cohen | |
| 9,636,019 B2 | 5/2017 | Hendler et al. | |
| 2018/0228423 A1 | 8/2018 | Intrator | |
| 2020/0402643 A1* | 12/2020 | Trees | G16H 10/20 |
| 2022/0054033 A1* | 2/2022 | Honke | A61B 5/6814 |

FOREIGN PATENT DOCUMENTS

WO WO 2003/100450 A1 12/2003

OTHER PUBLICATIONS

Curry et al., "A sparse EEG-informed fMRI model for hybrid EEG-fMRI neurofeedback prediction," Frontiers in Neuroscience, 13: 1451 (2019).

(Continued)

*Primary Examiner* — Andrew H Lam
(74) *Attorney, Agent, or Firm* — Baker Botts LLP

(57) ABSTRACT

The present subject matter relates to techniques for hierarchical deep transcoding. The disclosed system can include a processor that can be configured to receive a functional magnetic resonance imaging (fMRI) data and/or an extracranial electroencephalogram (EEG) data and reconstruct a latent source space from the fMRI data and/or the EEG data by decoding the EEG data and/or the fMRI data to a latent source space. The fMRI data and the EEG data can be simultaneously acquired.

18 Claims, 48 Drawing Sheets
(40 of 48 Drawing Sheet(s) Filed in Color)

(56) References Cited

OTHER PUBLICATIONS

Dong et al., "Neuroscience information toolbox: an open source toolbox for EEG-fMRI multimodal fusion analysis," Frontiers in Neuroinformatics, vol. 12, 12 pages (2018).

Gonçalves et al., "Correlating the alpha rhythm to BOLD using simultaneous EEG/fMRI: Inter-subject variability," NeuroImage, vol. 30 / Issue 1, 203-213 (2006).

Hao et al., "DeepIED: An epileptic discharge detector for EEG-fMRI based on deep learning," NeuroImage: Clinical, vol. 17, 962-975 (2018).

Hosseini et al., "Multimodal data analysis of epileptic EEG and rs-fMRI via deep learning and edge computing," Artificial Intelligence in Medicine, vol. 104 (2020).

Huster et al., "Methods for Simultaneous EEG-fMRI: An Introductory Review," The Journal of Neuroscience, 32(18):6053-6060 (2012).

Lei et al., "Multimodal functional network connectivity: an EEG-fMRI fusion in network space," PloS One, 6(9) e24642 (2011).

Martinez-Montes et al., "Concurrent EEG/fMRI analysis by multiway partial least squares," NeuroImage, vol. 22 / Issue 3, 1023-1034 (2004).

Meir-Hasson et al., "An EEG Finger-Print of fMRI deep regional activation," NeuroImage, vol. 102, 128-141 (2014).

Oberlin et al., "Symmetrical EEG-fMRI imaging by sparse regularization," 2015 23rd European Signal Processing Conference, 1915-1919 (2015).

Olbrich et al., "EEG-vigilance and BOLD effect during simultaneous EEG/fMRI measurement," NeuroImage, 45 (2), 319-332 (2009).

Safi-Harb et al., "Advantages and disadvantages of a fast fMRI sequence in the context of EEG-fMRI investigation of epilepsy patients: a realistic simulation study," NeuroImage, 119, 20-32 (2015).

Steyrl et al., "Reference layer adaptive filtering (RLAF) for EEG artifact reduction in simultaneous EEG-fMRI," J. Neural Eng., 14 (2017).

\* cited by examiner

| i) EEG-to-fMRI | corrcoef Vanilla | std Vanilla | corrcoef Cyclic | std Cyclic |
|---|---|---|---|---|
| Interleave0 | 0.657 | 0.006 | 0.673 | 0.003 |
| Interleave5 | 0.583 | 0.025 | 0.641 | 0.004 |
| Interleave5Noise5 | 0.695 | 0.006 | 0.646 | 0.004 |

| ii) fMRI-to-EEG | corrcoef Vanilla | std Vanilla | corrcoef Cyclic | std Cyclic |
|---|---|---|---|---|
| Interleave0 | 0.328 | 0.024 | 0.705 | 0.012 |
| Interleave5 | 0.361 | 0.037 | 0.825 | 0.010 |
| Interleave5Noise5 | 0.363 | 0.026 | 0.416 | 0.019 |

| iii) fMRI source est. | corrcoef osc | std osc | corrcoef sparse | std sparse |
|---|---|---|---|---|
| Interleave0 | 0.661 | 0.040 | 0.590 | 0.015 |
| Interleave5 | 0.123 | 0.015 | 0.533 | 0.025 |
| Interleave5Noise5 | 0.187 | 0.022 | 0.567 | 0.021 |

| iv) EEG source est. | corrcoef osc | std osc | corrcoef sparse | std sparse |
|---|---|---|---|---|
| Interleave0 | 0.355 | 0.008 | 0.052 | 0.006 |
| Interleave5 | 0.637 | 0.012 | 0.192 | 0.014 |
| Interleave5Noise5 | 0.733 | 0.014 | 0.320 | 0.013 |

| v) Classic Method | corrcoef osc | std osc | corrcoef sparse | std sparse |
|---|---|---|---|---|
| Interleave0 | 0.716 | 0.013 | 0.226 | 0.015 |
| Interleave5 | 0.716 | 0.013 | 0.226 | 0.015 |
| Interleave5Noise5 | 0.716 | 0.013 | 0.226 | 0.015 |

| vi) Cyclic Transcoder | corrcoef osc | std osc | corrcoef sparse | std sparse |
|---|---|---|---|---|
| Interleave0 | 0.765 | 0.017 | 0.408 | 0.011 |
| Interleave5 | 0.776 | 0.016 | 0.390 | 0.010 |
| Interleave5Noise5 | 0.775 | 0.015 | 0.390 | 0.011 |

FIG. 5B

SYSTEMS AND METHODS FOR FUSING EEG AND fMRI THROUGH HIERARCHICAL DEEP TRANSCODING

CROSS-REFERENCE TO RELATED APPLICATION

This application claims priority to U.S. Provisional Patent Application Nos. 63/087,806, which was filed on Oct. 5, 2020, the entire contents of which are incorporated by reference herein.

GRANT INFORMATION

This invention was made with government support under grant number W911NF-10-2-0022 from the Army Research Lab and N00014-20-1-2027 from the Office of Naval Research. The government has certain rights in the invention.

BACKGROUND

Functional magnetic resonance imaging (fMRI) is a neuroimaging modality that can be used for cognitive neuroscience and clinical psychiatry. While fMRI scans can provide full brain coverage at a relatively high spatial resolution, temporal resolution can be limited due to a sluggish hemodynamic response. The cost of certain fMRI scans can range between about $600 to $1200 per scan, with the scan machine itself costing about $3 million or more.

Electroencephalograph (EEG) is a neuroimaging modality that can have high temporal resolution low spatial resolution. The cost of certain EEG scans can be lower than certain fMRI scans, e.g., less than $10 per scan with certain EEG equipment available for less than $50 thousand.

There is a need for a technique that can estimate fMRI data from collected EEG data and vice versa.

SUMMARY

The disclosed subject matter provides techniques for hierarchical transcoding. An example system can include a processor configured to receive a functional magnetic resonance imaging (fMRI) data and/or an extracranial electroencephalogram (EEG) data and reconstruct a latent source space from the fMRI data and/or the EEG data by decoding the EEG data and/or the fMRI data to the latent source space. In non-limiting embodiments, the fMRI data and the EEG data can be simultaneously acquired.

In certain embodiments, the processor can be configured to transcode the EEG data in the latent source space to have an fMRI signal and/or the fMRI data in the latent source space to an EEG signal.

In certain embodiments, the processor is further configured to train a group-level model with a plurality of EEG and fMRI signals obtained from at least two subjects to determine an intermediate spatial/temporal resolution of the EEG and fMRI signals, and generates estimates of the latent source space of the intermediate resolution from the EEG and fMRI signals based on the trained group-level model. In non-limiting embodiments, the interpolated EEG and fMRI signals can have the same intermediate resolution for training the group-level model.

In certain embodiments, the processor can be configured to train a subject-level model with the group-level latent space estimates from the EEG and fMRI signals to determine a spatial/temporal resolution of the subject-level latent source space, and determine the subject-level latent source space using the subject-level model. The group-level latent space estimates can be epoched to achieve a 3D event related potential (ERP) representation. In non-limiting embodiments, the epoched signals can be sliced in a spatial and temporal direction.

In certain embodiments, the group-level model and the subject-level model are a cyclic convolutional transcoder. In non-limiting embodiments, the cyclic convolutional transcoder can include an fMRI decoder, an fMRI encoder, an EEG decoder, an EEG encoder, or combinations thereof. In non-limiting embodiments, the fMRI decoder can decode the latent source space from an fMRI encoding. The EEG decoder can decode the latent source space from an EEG encoding. In non-limiting embodiments, the fMRI encoder can encode the latent source space into an fMRI encoding, and the EEG encoder can encode the latent source space into an EEG encoding.

In certain embodiments, the fMRI decoder and the fMRI encoder can include temporal convolutional layers. In non-limiting embodiments, the EEG decoder and the EGG encoder can include spatial convolutional layers.

In certain embodiments, the EEG data can be transcoded to an fMRI signal and/or the fMRI data can be transcoded to an EEG signal based on the spatial/temporal resolution of the latent source space determined by both the group-level and subject-level models. In non-limiting embodiments, the processor can be configured to generate a map based on the reconstructed the EEG signal and/or the fMRI signal. In non-limiting embodiments, the map can include an activation map, a Z-statistic map, or a combination thereof.

In certain embodiments, the disclosed subject matter provides methods for hierarchical deep transcoding. An example method can include receiving a functional magnetic resonance imaging (fMRI) data and/or an extracranial electroencephalogram (EEG) data, and reconstructing a latent source space from the EEG data and/or fMRI data by decoding the EEG data and/or the fMRI data in the latent source space. In non-limiting embodiments, the fMRI data and the EEG data can be simultaneously acquired.

In certain embodiments, the method can further include training a group-level model with a plurality of EEG and fMRI signals obtained from at least two subjects to determine an intermediate spatial/temporal resolution of the EEG and fMRI signals, and generating estimates of the latent source space of the intermediate resolution from the EEG and fMRI signals based on the trained group-level model. In non-limiting embodiments, the interpolated EEG and fMRI signals can have the same intermediate resolution for training the group-level model.

In certain embodiments, the method can include training a subject-level model with the group-level latent space estimates from the EEG and fMRI signals to determine a spatial/temporal resolution of the subject-level latent source space, and determining the subject-level latent source space using the subject-level model. In non-limiting embodiments, the ground-level latent space estimates can be epoched to achieve a 3D event related potential (ERP) representation. In non-limiting embodiments, the EEG data and the fMRI data in the latent source space can be transcoded to an EEG signal or the EEG data in the latent source space can be transcoded to an fMRI signal based on the spatial/temporal resolution of the latent source space determined by both the group-level and subject-level models.

In certain embodiments, the method can include generating a map based on the reconstructed the EEG signal and/or the fMRI signal. In non-limiting embodiments, the map can include an activation map, a Z-statistic map, or combinations thereof.

The disclosed subject matter will be further described below.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 5B provides a chart showing the qualitative evaluation of simulated data.

Figure 1A:
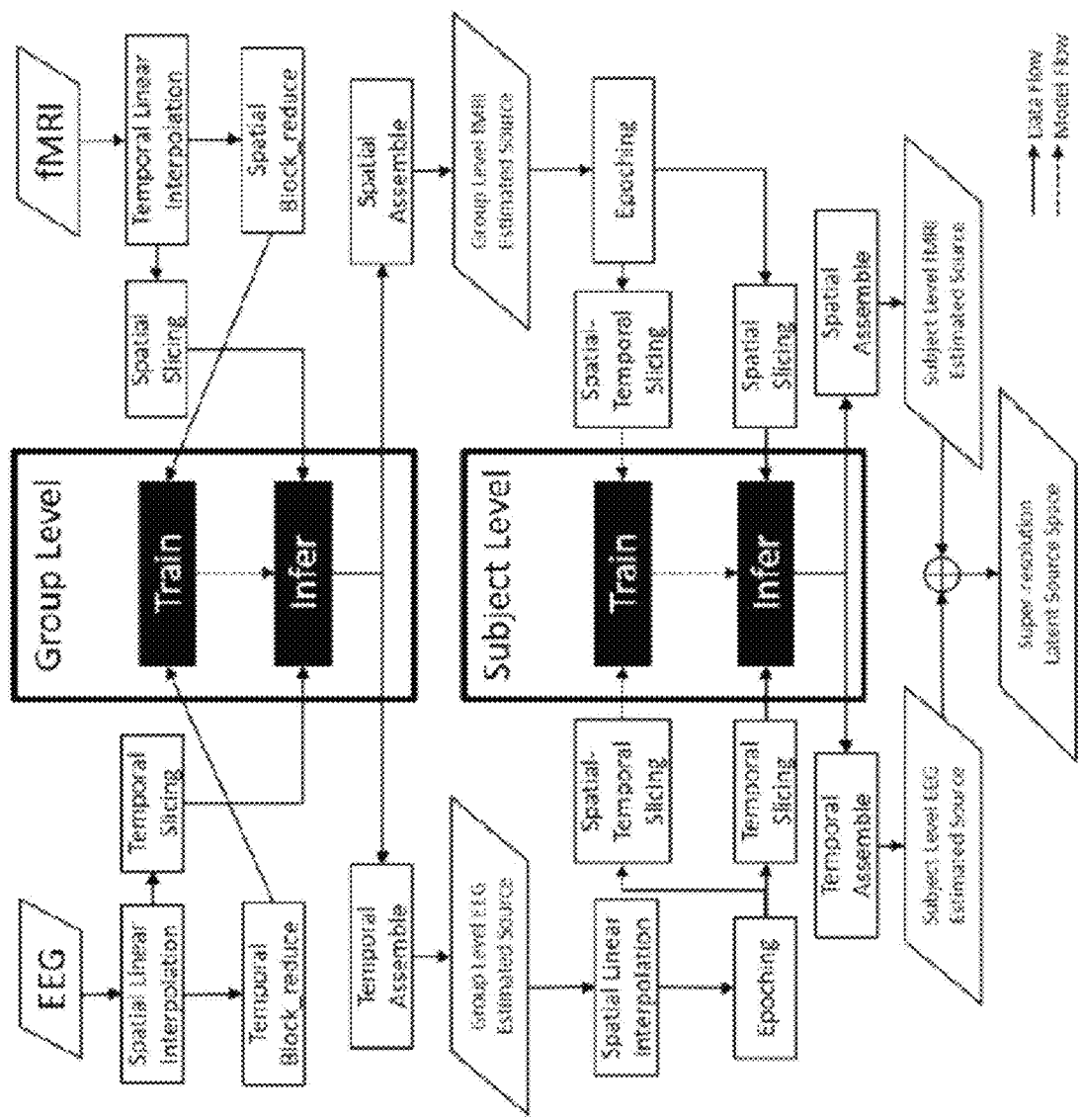
FIG. 1A provides a diagram showing a framework of hierarchical deep transcoding for modality fusing.

It is to be understood that both the foregoing general description and the following detailed description are exemplary and are intended to provide further explanation of the disclosed subject matter.

DETAILED DESCRIPTION

The disclosed subject matter provides techniques for hierarchical deep transcoding. The disclosed system provides systems and methods for latent neural source recovery via transcoding/reconstruction of simultaneous electroencephalography (EEG) and functional magnetic resonance imaging (fMRI).

The terms "comprise(s)," "include(s)," "having," "has," "can," "contain(s)," and variants thereof, as used herein, are intended to be open-ended transitional phrases, terms, or words that do not preclude additional acts or structures. The singular forms "a," "an," and "the" include plural references unless the context clearly dictates otherwise. The present disclosure also contemplates other embodiments "comprising," "consisting of," and "consisting essentially of," the embodiments or elements presented herein, whether explicitly set forth or not.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, up to 10%, up to 5%, and up to 1% of a given value. Alternatively, e.g., with respect to biological systems or processes, the term can mean within an order of magnitude, within 5-fold, and within 2-fold, of a value.

The term "coupled," as used herein, refers to the connection of a device component to another device component by methods known in the art.

As used herein, the term "subject" includes any human or nonhuman animal. The term "nonhuman animal" includes, but is not limited to, all vertebrates, e.g., mammals and non-mammals, such as nonhuman primates, dogs, cats, sheep, horses, cows, chickens, amphibians, reptiles, etc.

In certain embodiments, the disclosed subject matter provides a system for hierarchical deep transcoding. An example system can include a processor. The processor can be configured to perform the instructions specified by software stored in a hard drive, a removable storage medium, or any other storage media. The software can be written in a variety of languages, e.g., MATLAB and/or Microsoft Visual C++. Additionally or alternatively, the processor can include hardware logic, such as logic implemented in an application-specific integrated circuit (ASIC). The processor can be configured to control one or more of the system components.

In certain embodiments, the processor can be configured to receive functional magnetic resonance imaging (fMRI) data and extracranial electroencephalogram (EEG) data and reconstruct the EEG data and the fMRI data in latent source space. In non-limiting embodiments, the fMRI and EEG signals can be simultaneously acquired data/signals. In non-limiting embodiments, the processor can be configured to transcode the modalities (e.g., fMRI data and EEG data) from one to another (e.g., fMRI data to EEG format and/or EEG data to fMRI format) via the latent source space.

The latent source space can be the underlying spatiotemporal neural activity that can generate multiple sets of measurements (e.g., the two sets of measurements: the EEG and fMRI). The disclosed system can be a data driven system and can perform inference of the source space by exploiting the complementarity of the EEG and fMRI measurements to measure brain activities. In non-limiting embodiments, the disclosed system can reconstruct the fMRI and EEG data in the latent source space without any knowledge of hemodynamic coupling and/or leadfield estimates. In some embodiments, the processor can be configured to generate a map showing the reconstructed EEG and fMRI data in the latent source space. In non-limiting embodiments, the terms "EEG sourcing" or "EEG source localization" refer to the estimating the latent source space from EEG. In non-limiting embodiments, the terms "fMRI deconvolution" refers to the estimating the latent source space from fMRI. In certain embodiments, the processor can include a cyclic convolutional transcoder that can transcode the data (e.g., EEG to fMRI or fMRI to EEG) and/or generate the super-resolution latent source space. For example, the processor can include a group-level model and/or a subject-level model that can transcode the data.

In certain embodiments, the processor can be configured to train the cyclic convolutional transcoder with a plurality of EEG and fMRI signals/data. For example, the processor can be configured to train a group-level model with a plurality of EEG and fMRI signals obtained from different subjects to determine an intermediate resolution of the plurality of EEG and fMRI signals. The intermediate resolution can include a spatial resolution and a temporal resolution.

In the group-level model, the simultaneous EEG and fMRI data can go through spatial/temporal linear interpolation to reach the intermediate spatial/temporal resolution. The interpolated EEG/fMRI data can be temporally/spatially block reduced respectively, so both of them are of the same intermediate spatial/temporal resolution (e.g., about 12 mm/2.7 Hz) for training the group-level model. The intermediate spatial/temporal resolution can vary depending on fMRI's slice-timing setting for training the group-level model. In non-limiting embodiments, the trained group-level model can be configured to infer and generate a temporal assemble and a spatial assemble. For example, the assembled group-level EEG estimated source can include a spatial/temporal resolution of about 12 mm/100 Hz and the assembled group-level fMRI estimated source can include spatial/temporal resolution of 2 mm/2.7 Hz.

In certain embodiments, the processor can be configured to train a subject-level model to determine a spatial/temporal resolution of the latent source space based on the interpolated signals. For example, the assembled group-level sources can be epoched according to task onsets to achieve 3D event-related potential (ERP) representations after the group-level EEG estimated source is spatially linearly interpolated (e.g., to 2 mm). By taking advantage of the jittering nature of the event onset of the experimental design, epoched group-level fMRI estimated source can have denser information. In non-limiting embodiments, the epoched signals can have the improved signal-to-noise ratio of the group-level EEG/fMRI estimated source. In non-limiting embodiments, the epoched group-level EEG/fMRI estimated source can be both sliced in spatial and temporal direction for training a subject-level model for each single subject.

In certain embodiments, the trained subject-level model can be configured to infer a desirable spatial and temporal resolution of the latent source space (e.g., super-resolution latent source space) and create a temporal/spatial assemble. For example, during inferring, the subject-level model can be applied to each time point/3D volume for EEG/fMRI signals, respectively. After assembling, both the subject-level EEG/fMRI estimated source, which can have the inferred spatial and temporal resolution of super-resolution latent source space, can be generated. In non-limiting embodiments, the EEG estimated source and the fMRI estimated source can be added to achieve the super-resolution latent source space. In some embodiments, the EEG estimated source and the fMRI estimated source can be separately analyzed.

In certain embodiments, the group-level model and the subject-level model can be cyclic convolutional transcoders. The cyclic convolutional transcoder can include an fMRI decoder, an fMRI encoder, an EEG decoder, an EEG encoder, or combinations thereof. In non-limiting embodiments, both EEG and fMRI can be an encoding of the latent source space so a decoder can decode the latent source space from an encoding (e.g., EEG/fMRI), while an encoder encodes the latent source space into an encoding (e.g., EEG/fMRI). In some embodiments, the fMRI/EEG decoder can include transpose temporal/spatial convolutional layers, while the fMRI/EEG encoder can include temporal/spatial convolutional layers. This structure can ensure that the fMRI encoder/decoder can apply a temporal transformation to the original fMRI data, and EEG encoder/decoder can apply a temporal transformation to the original EEG data. In non-limiting embodiments, the processor can include loss functions. The loss functions can be the functions that can be minimized in the training process. For example, the processor can have loss functions, which can include four error terms—two representing the transcoding loss and two the cycle loss.

In non-limiting embodiments, the group-level and subject-level models can have the disclosed encoder/decoder structures. The models with the disclosed structure can maintain the temporal/spatial information of EEG/fMRI and be interpretable models. For example, the fMRI decoder can improve the fMRI blind deconvolution to decode the latent source space from fMRI. The EEG decoder can improve the EEG blind signal separation to achieve source localization from channel-wise EEG recordings to 3D brain volume. The fMRI encoder can convolve the latent source space with an HRF estimated from data to encode it to fMRI data. The EEG encoder can perform mapping the latent source space signal from 3D brain volume to electrodes on the surface of the scalp through a forward head model (e.g., lead field matrix) estimated from the data to encode it to EEG data.

In certain embodiments, the EEG data and fMRI data can be simultaneously acquired data/signals. For example, the EEG data and fMRI data can be simultaneously recorded while a subject performs an oddball auditory task (e.g., including 80% standard and 20% oddball stimuli). The standard stimuli can include pure tones (e.g., with a frequency of 350 Hz), while the oddball stimuli can include broadband (laser gun) sounds. Stimuli can last for a predetermined time (e.g., about 200 ms) with an inter-trial interval (ITI) sampled from a uniform distribution (e.g., between about 2 s and 3 s). Subjects can be instructed to ignore standard tones and respond to oddball sounds as quickly and as accurately as possible by pressing a button.

In certain embodiments, the processor can be configured additional data. For example, additional data can include structural images, functional echo plannar imaging (EPI) images, one single-volume high-resolution EPI image, or combinations thereof.

In certain embodiments, the data can be pre-processed. For example, for EEG data-processing, raw EEG data can be imported to the processor and be low-pass filtered with a cutoff frequency (e.g., 70 Hz by a non-causal finite impulse response (FIR) filter). In non-limiting embodiments, an fMRI Artifact Slice Template Removal algorithm (FASTR) can be used for gradient artifact removal. Then, the EEG data can be resampled (e.g., to 500 Hz). The EEG data can be high-pass filtered (e.g., at 0.25 Hz with another FIR filter) to reduce electrode drift before performing QRS complex detection. The generated QRS complex event times can be used to remove the ballistocardiogram (BCG) effect of another copy of the EEG data (not high-pass filtered), with the FMRIB plugin's BCG suppression function set to Optimal Basis Set (OBS) mode with a number of bases set to four (the default).

In certain embodiments, the fMRI data can be preprocessed. For example, using FEAT analysis, a brain/background threshold can be set (e.g., at 10%), and a high-pass filter with a cutoff (e.g., at 60 seconds) can be applied. Spatial normalization can be achieved by first registering the fMRI data to a high-resolution functional image, which can then be registered to the structural image (T1) and finally to a standard space image. In non-limiting embodiments, the fMRI data after spatial normalization be with a FOV of 90×108×90 voxels, at a voxel size of 2×2×2 mm.

In certain embodiments, the disclosed system can further include a device for detecting EEG signals and/or fMRI data from a target subject. For example, the disclosed system can include an EEG cap with electrodes and/or an fMRI imaging device.

In certain embodiments, the disclosed system can be configured to generate a map (e.g., activation map or Z-statistic maps) based on the reconstructed EEG data and the fMRI data in the latent source space.

The disclosed processor that can be configured to receive a functional magnetic resonance imaging (fMRI) data and/or an extracranial electroencephalogram (EEG) data and reconstruct a high spatial-temporal resolution latent source space from the fMRI data and/or the EEG data by decoding the EEG data and/or the fMRI data to a latent source space. The processor can resolve fMRI deconvolution, EEG sourcing/source localization, fMRI hemodynamic response function (HRF) estimation, EEG forward/inverse head conductivity model(i.e. leadfield matrix) estimation in the process.

In certain embodiments, the disclosed subject matter provides a method for hierarchical deep transcoding. An example method can include receiving functional magnetic resonance imaging (fMRI) data and extracranial electroencephalogram (EEG) data and reconstructing the EEG data and the fMRI data in latent source space. The fMRI data and the EEG data can be simultaneously acquired.

In certain embodiments, the method can further include training a group-level model and a subject-level model that can reconstruct the EEG data and the fMRI data in the latent source space using the disclosed system. For example, the method can include training a group-level model with a plurality of EEG and fMRI signals obtained from at least two subjects to determine an intermediate resolution of the plurality of EEG and fMRI signals and performing linear interpolation on the plurality of EEG and fMRI signals based on the trained group-level model. In non-limiting embodiments, the interpolated EEG and fMRI signals can have the same intermediate resolution for training the group-level model.

In certain embodiments, the method can include training a subject-level model with the interpolated signals to determine a spatial/temporal resolution of the latent source space and determining the spatial/temporal resolution of the latent source space using the subject-level model. In non-limiting embodiments, the EEG data and the fMRI data can be in latent source space. For example, the EEG data and the fMRI data can be reconstructed in the latent source space based on the spatial/temporal resolution of the latent source space determined by the group-level model and the subject-level model.

In certain embodiments, the method can further include generating a map based on the reconstructed EEG data and the fMRI data in the latent source space. For example, when only fMRI or EEG data for a target subject is available, the disclosed subject matter can provide a complete transcoding model, which can be trained on other subjects. The disclosed model can generate EEG from fMRI or fMRI from EEG for the target subject. The generated data (e.g., EEG or fMRI) can be fed together with original data (e.g., fMRI or EEG) into the model again to generate the source space. The disclosed subject matter can allow building the source space map from one modality (e.g., fMRI or EEG). In non-limiting embodiments, the subject can receive a personalized treatment based on an analysis of the map.

Without any prior knowledge of either the hemodynamic response function or lead field matrix, the disclosed techniques can exploit the temporal and spatial relationships between the modalities (e.g., EEG and fMRI) and latent source spaces for learning these mappings. Using the EEG-fMRI data, the disclosed subject matter can transcode the modalities from one to another and/or reconstruct them in the latest source spaces. In addition to enabling symmetrical inferring of a latent source space, the disclosed techniques can provide low-cost computational neuroimaging (e.g., by generating an expensive fMRI BOLD image from the low-cost EEG data). The disclosed systems and methods can be used for brain-computer interfaces (BCI) to measure brain activity.

EXAMPLES

Example 1: Simultaneous Acquired EEG-fMRI Super-Resolution Latent Space Reconstruction Measuring brain dynamics at both high spatial and temporal resolution, e.g., at the scale of millimeters×milliseconds, can be important in clinical diagnostic procedures and can play a vital role in cognitive and behavioral research such as language decoding. It can be achieved by Electrocorticography (ECoG) or intracranial electroencephalography (iEEG), a type of electrophysiological monitoring that uses electrodes placed directly on the exposed surface of the brain to record electrical activity from the cerebral cortex. However, ECoG implant is relatively invasive, requiring an open skull surgery, comparing to noninvasive brain imaging modalities such as Magnetoencephalography(MEG), functional magnetic resonance imaging (fMRI) and extracranial electroencephalogram (EEG).

Due to its invasive nature, ECoG assessments face many difficulties recruiting subjects, as patients with ECoG implants are rare. Meanwhile, none of the noninvasive methods alone can replace ECoG in research and clinical applications adequately—EEG and MEG of milliseconds temporal resolution are not comparable to ECoG in spatial resolution, while fMRI covering millimeters spatial resolution has a lower temporal resolution relative to ECoG.

Simultaneously acquired EEG-fMRI can show a silver lining in solving this dilemma. However, the difficulty of fusing simultaneous EEG-fMRI data to achieve ECoG's spatial and temporal resolution lies in the vast differences between EEG and fMRI. EEG records local field potential (LFP) signal from several electrodes on the surface of the scalp, while fMRI records blood oxygenation level-dependent (BOLD) signal from the whole brain 3D volume through sophisticated location encoding. While both LFP and BOLD can be induced by the underlying brain activity, the relationship between LFP, BOLD and brain activity remains unclear in many ways. For instance, subject-wise differences are reported both in hemodynamic coupling—the relationship between BOLD and brain activity, and in the head conductivity model, which plays an important role in modeling the relationship between LFP and brain activity. As the aiming fused space can be a high spatial and temporal resolution, it can be sensitive to any model variance like subject-wise difference. Due to these difficulties, the analysis of simultaneous EEG-fMRI is still mostly separated, biased and/or primitive.

While simultaneously acquired EEG-fMRI shows great potential in behavior and cognitive tests, most simultaneous EEG-fMRI tests are limited to asymmetrical fusion methods biased towards one of the modalities. EEG-informed fMRI analysis extracts some features from EEG, such as P300 amplitude and latency features, EEG source dipole time series, global EEG synchronization in the alpha frequency band, or single-trial EEG correlates of task-related activity and uses these as an explanatory variable in fMRI analysis. While fMRI-informed EEG can simply use the activation map calculated from fMRI data to improve the source localization accuracy of EEG analysis, the bias towards one of the modalities can cause information loss in the other modality.

To eliminate the bias, symmetric latent feature space fusion methods are introduced. Latent features space fusion methods extract features from EEG and fMRI using Canonical Correlation Analysis (CCA), PCA, ICA, PLS, etc. and transform and unify them in a latent feature space. While bias is avoided with latent feature space fusion, during feature extracting and fusing, the only information shared by EEG and fMRI is presented in the latent space.

Figure 1B:
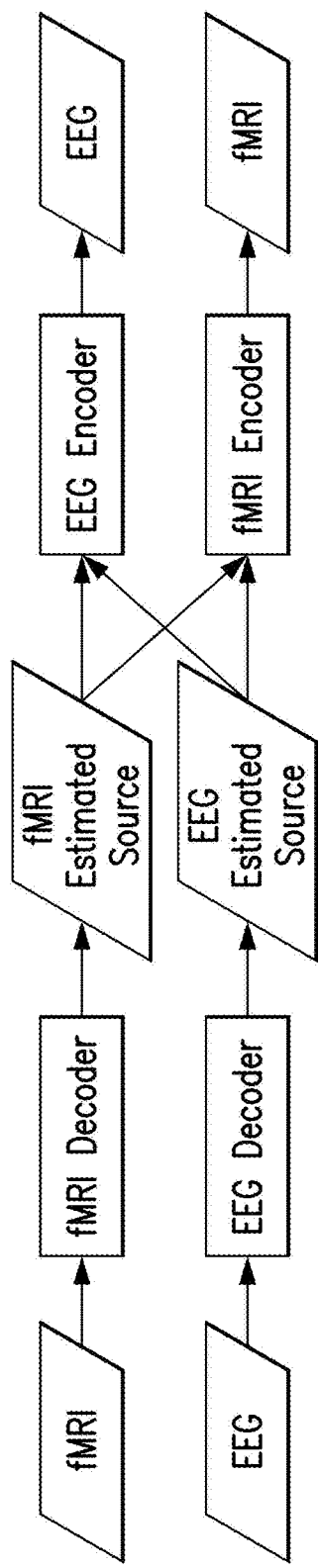
FIG. 1B provides a diagram showing a framework of a cyclic convolutional transcoder including an fMRI decoder, an EEG encoder, an EEG decoder and an fMRI encoder.
Figure 1C:
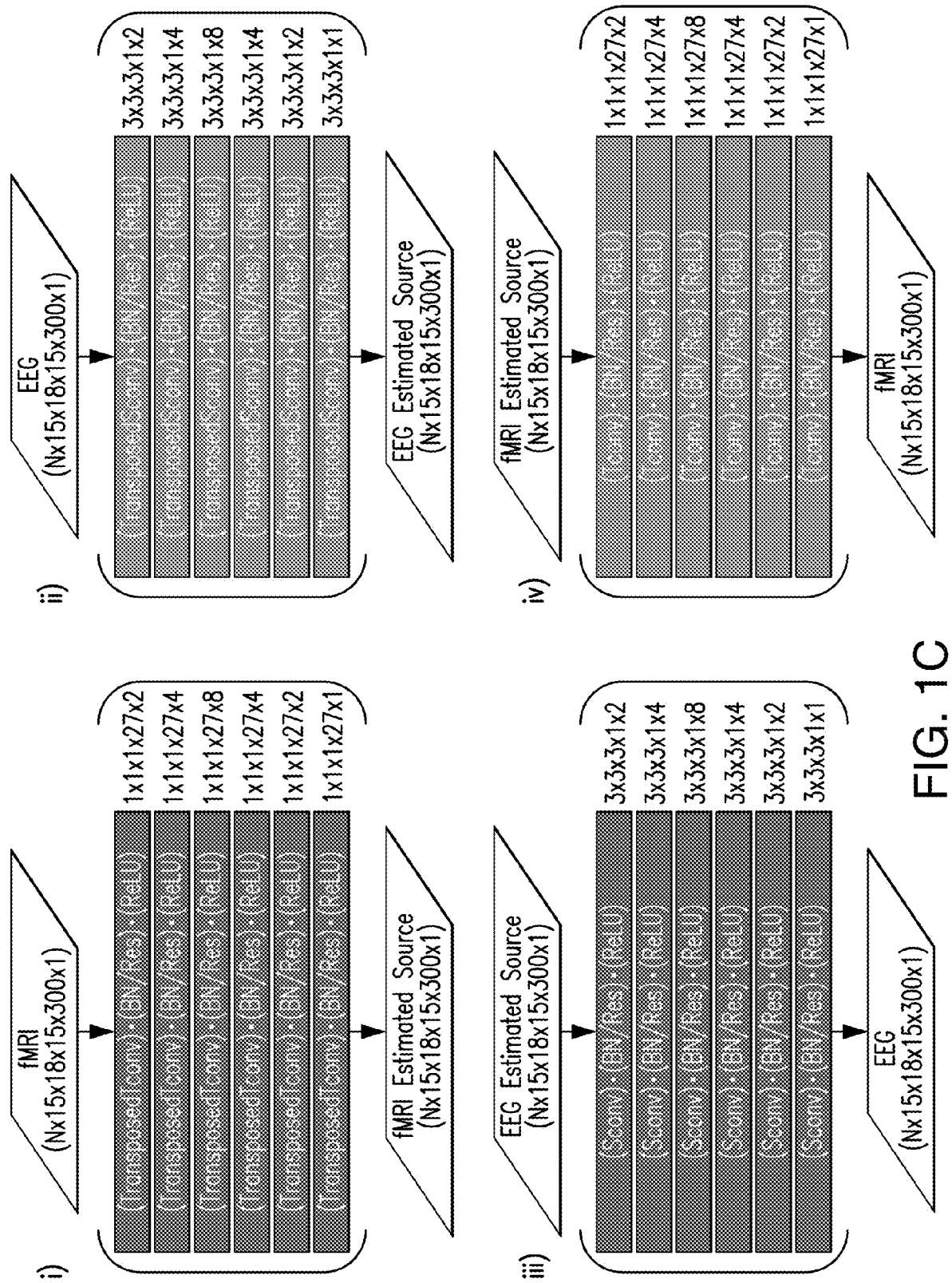
FIG. 1C provides diagrams showing a detailed structure of i) fMRI decoder, ii)EEG encoder, iii) EEG decoder, iv) fMRI encoder in accordance with the disclosed subject matter.
Figures 1, 5A:
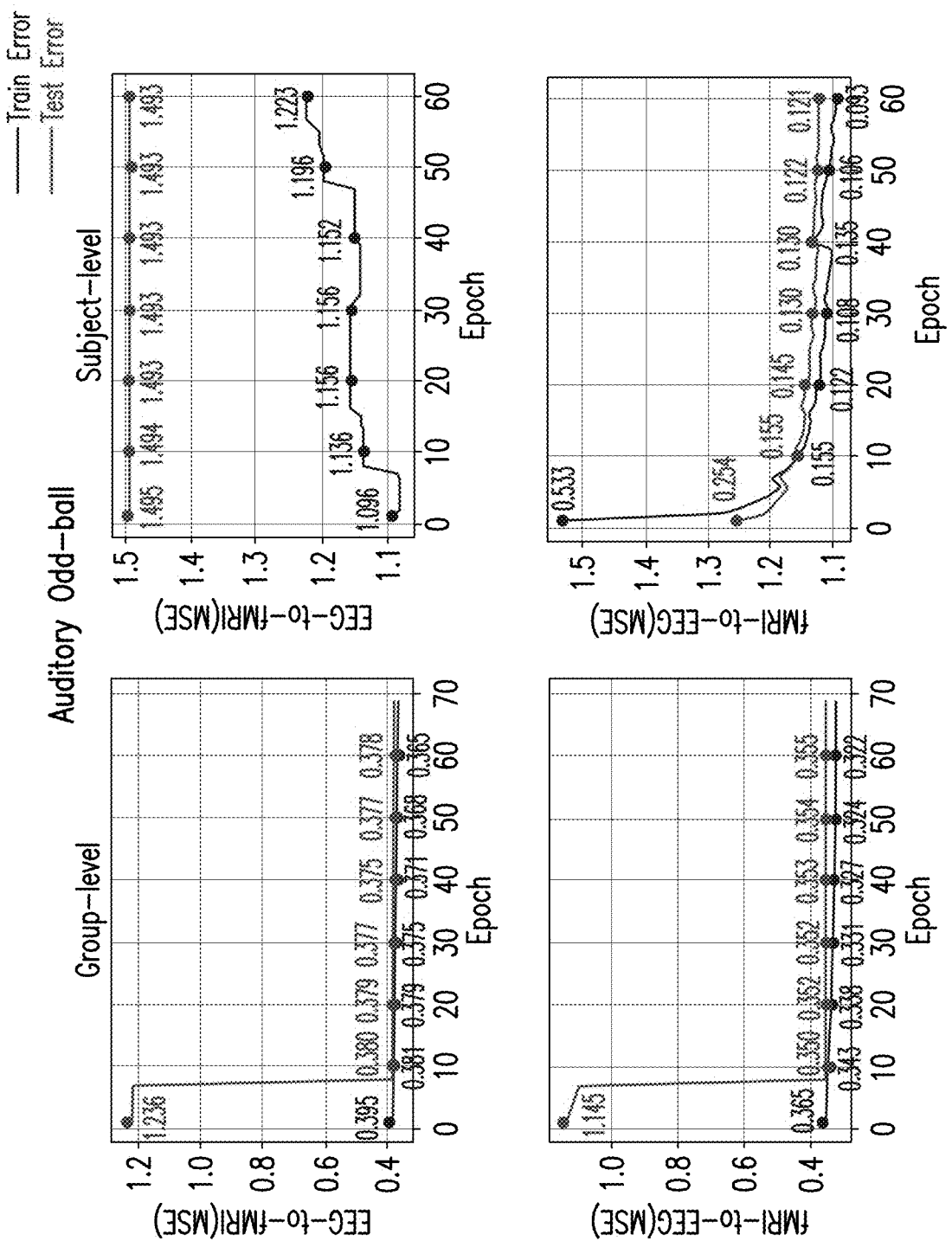
FIG. 5A provides graphs showing train and test errors of group-level and subject-level models.

The disclosed subject matter provides techniques for super-resolution latent source space reconstruction. The super-resolution latent source space with spatial and temporal resolution comparable to ECoG can be generated through a hierarchical deep transcoding process based on a Cyclic Convolutional Neural Network(CNN), as shown in FIG. 1. Both the group-level model and subject-level model are cyclic convolution transcoders, as shown in FIG. 1B. In froup level transcoders, batch-normalization layers can be used, while in subject-level transcoders, residual layers can be used instead. By transforming both EEG and fMRI and unifying them in this latent source space, a most comprehensible representation of the information can be achieved from simultaneously acquired EEG-fMRI without any knowledge of hemodynamic coupling or head conductivity model. The disclosed hierarchical deep transcoding framework can be designed for modality fusing problems of improved dimensionality and the limited number of samples. Moreover, instead of being a "black box," the disclosed model can provide improved interpretability. Certain features such as hemodynamic impulse response functions(HRF) can be extracted from the data.

Auditory Oddball Task Super-resolution Latent Source Space: In the auditory oddball paradigm, presentations of sequences of repetitive stimuli can be infrequently interrupted by a deviant stimulus. The subject is required to respond to the oddball stimuli by pressing a button. This particular experiment design was used because there are plenty of findings to cross-validate with many other techniques.

Figure 2B:
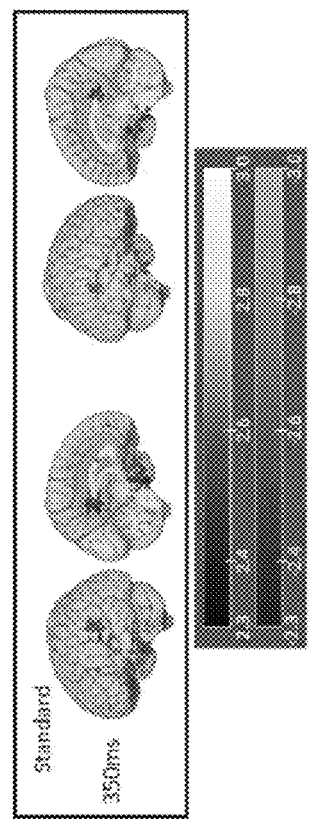
FIG. 2B provides images showing uncorrected Z-statistics of super-resolution latent source space reconstruction of brain dynamic during 0 to 450 ms after standard tone auditory stimuli onset in accordance with the disclosed subject matter.
Figure 2A:
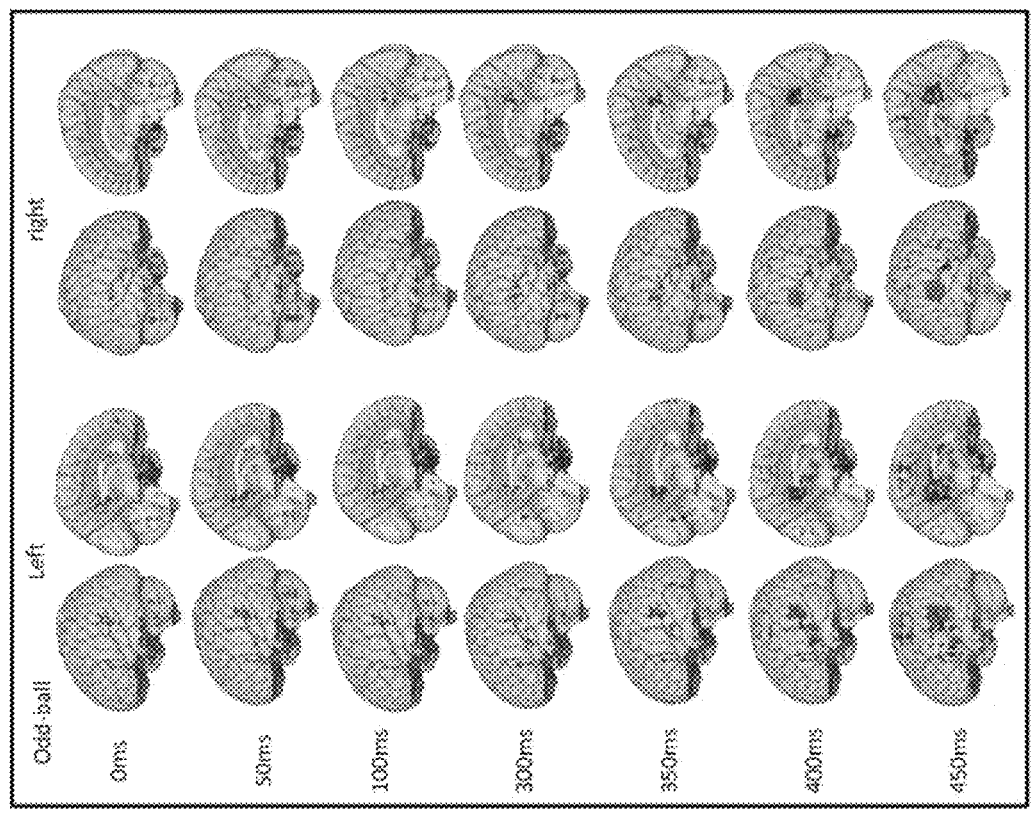
FIG. 2A provides images showing uncorrected Z-statistics of super-resolution latent source space reconstruction of brain dynamics during 0 to 450 ms after odd-ball.
Figure 3B:
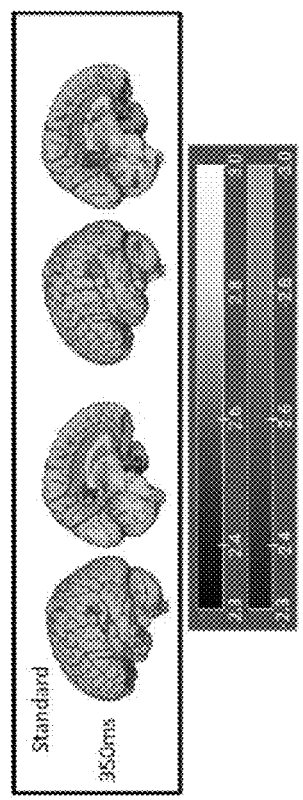
FIG. 3B provides images showing uncorrected Z-statistics of super-resolution latent source space reconstructed from EEG only (left) and fMRI only (right) of left-brain dynamic during 0 to 450 ms after standard tone auditory stimuli onset in accordance with the disclosed subject matter.
Figure 3A:
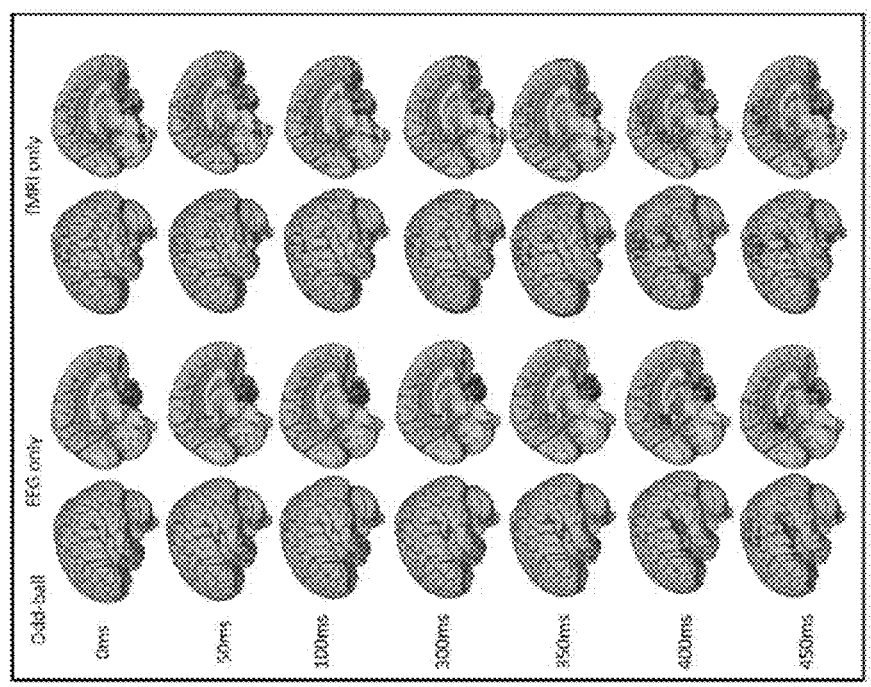
FIG. 3A provides images showing uncorrected Z-statistics of super-resolution latent source space reconstructed from EEG only (left) and fMRI only (right) of left-brain dynamic during 0 to 450 ms after Odd-ball.

The reconstructed super-resolution latent source space is of a spatial resolution of 2 mm and temporal resolution of 100 Hz. In FIG. 2a and FIG. 2B, some of the representative frames of the thresholded Z-statistics of super-resolution latent source space reconstruction of brain dynamic after auditory stimuli onset are shown for oddball and standard tones, respectively. Only one representative frame at 350 ms of the standard case is shown for comparison, as the activation map for standard stimuli only varies slightly in intensity.

In both cases, there is significantly prolonged deactivation shown by the blue-green color. The deactivation regions were spread across the prefrontal cortex, posterior cingulate cortex, temporal pole, etc. These regions form a network identified as the default mode network(DMN), which can be deactivated when participants perform external goal-directed tasks. Activation in the cerebellum was observed in both standard and odd-ball cases.

Both FIG. 2A and FIG. 2B shows prolong activation in the auditory cortex after the auditory stimulus, which agrees with ECoG findings. However, in FIG. 2A, there is a brief decline of the activation at the auditory cortex at around 100 ms after an odd-ball stimuli, which doesn't show in the standard case.

Moreover, around 400 ms after the onset of the odd-ball stimuli, significant activation was observed in the left primary motor cortex at regions corresponding to the right hand and index finger movement in FIG. 2A. Also, at around 450 ms, the activation starts to appear in the primary somatosensory cortex corresponding to the right hand and index finger sensory. Less significant activation also shows in the right primary motor cortex as bilateral activation is usually induced even with unilateral motions. These activations conform with the button pressing after the subjects hear an odd-ball stimuli with their right index finger, which are not observed in the standard tone activation map.

Figures 2, 5A:
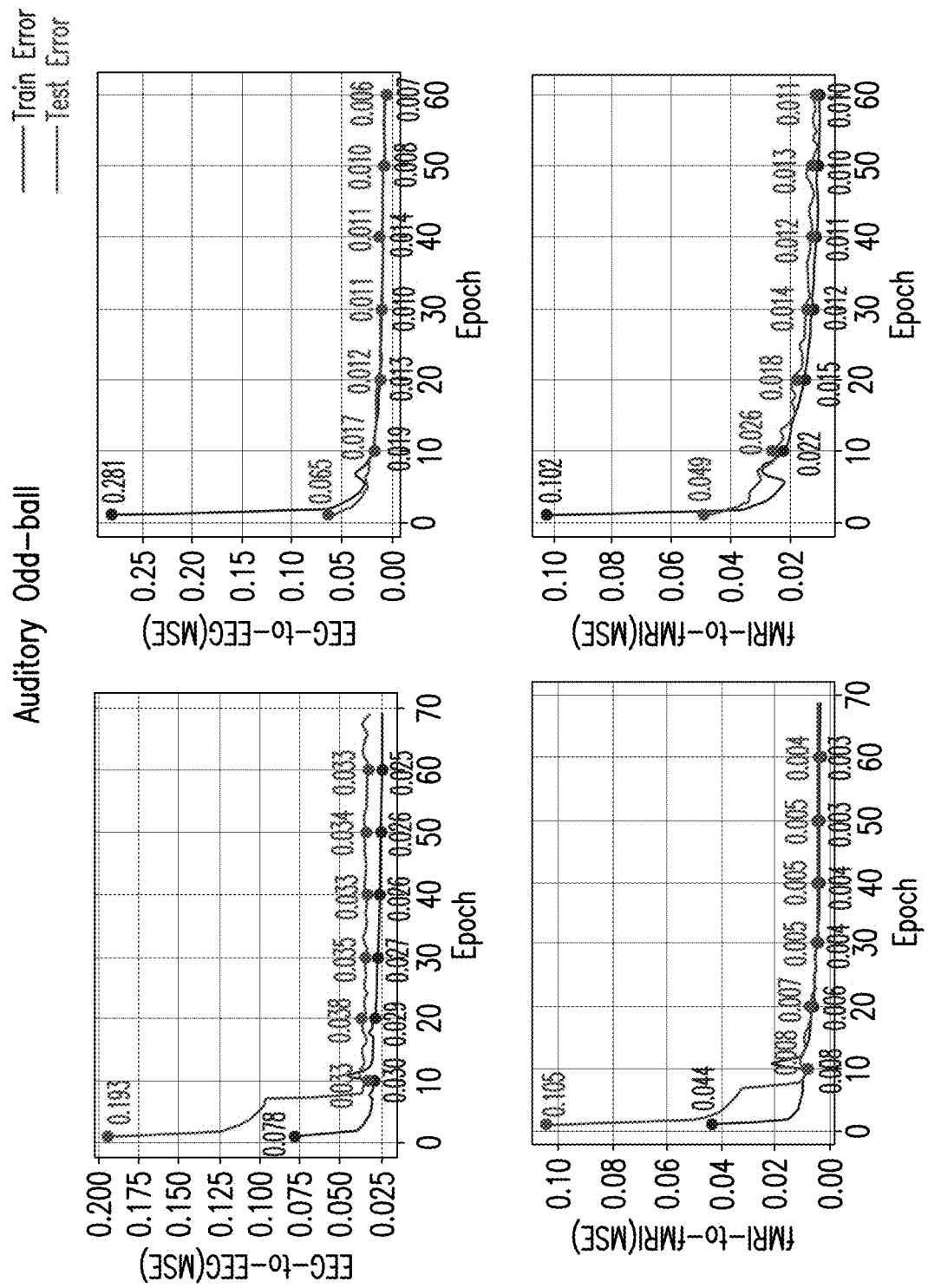
Figures 3, 5A:
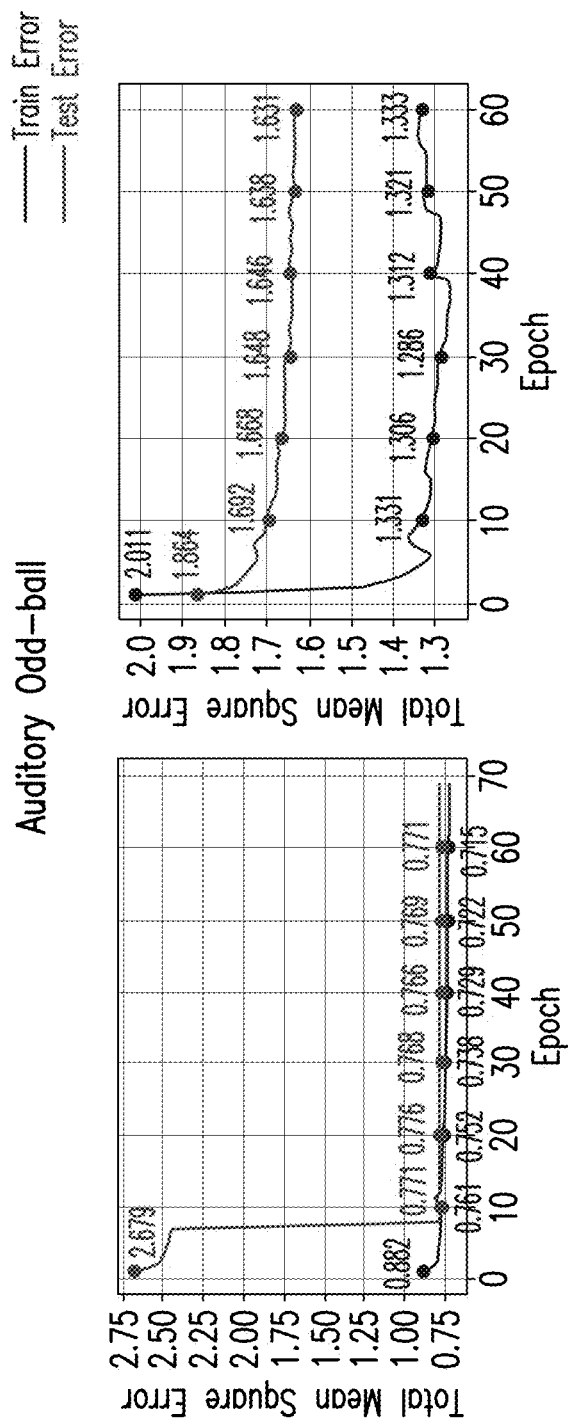

FIG. 3 shows the uncorrected Z-statistics of super-resolution latent source space reconstructed from only EEG(left) and only fMRI(right). The reconstruction from only EEG shows an advantage in temporal specificity while its source localization shows stronger stripe shape artifacts compared with the reconstruction generated from only fMRI.

Model Interpretation: one of the unique features of the disclosed system/model is its high interpretability, especially for the group-level model. Certain analyses (e.g., on auditory odd-ball dataset) were used to assess the characteristics of the disclosed model.

Figure 4A:
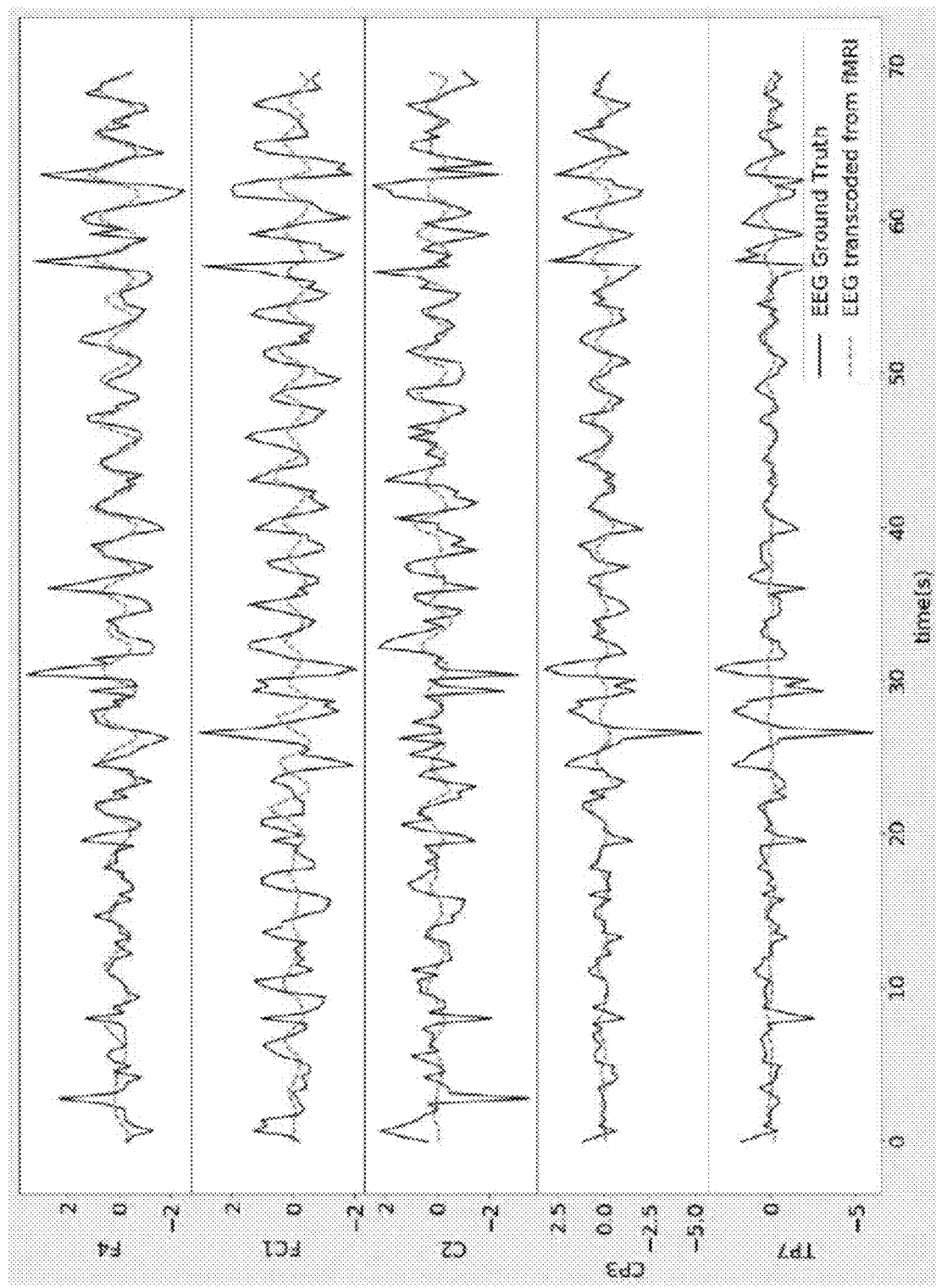
FIG. 4A provides a graph showing EEG signals transcoded from fMRI compared with the EEG ground truth.

The group-level cyclic convolutional transcoder forms EEG-to-fMRI and fMRI-to-EEG end-to-end structure. After training, the disclosed model was used to infer fMRI from EEG and EEG from fMRI, when only one modality is acquired. FIG. 4A shows some of the EEG channels inferred from the fMRI data of a subject that the model is not trained on and demonstrates that they resemble the real simultaneously acquired correspondent EEG channels despite the subject-wise difference. Leave-one-subject-out cross-validation was applied to the group-level model: out of a total of 87 runs from 19 subjects, 84 runs show significant correlations (mean correlation coefficient 0.133±0.082) at a significant level of alpha=0.05 (significance level determined with Bonferroni correction).

Figure 4B:
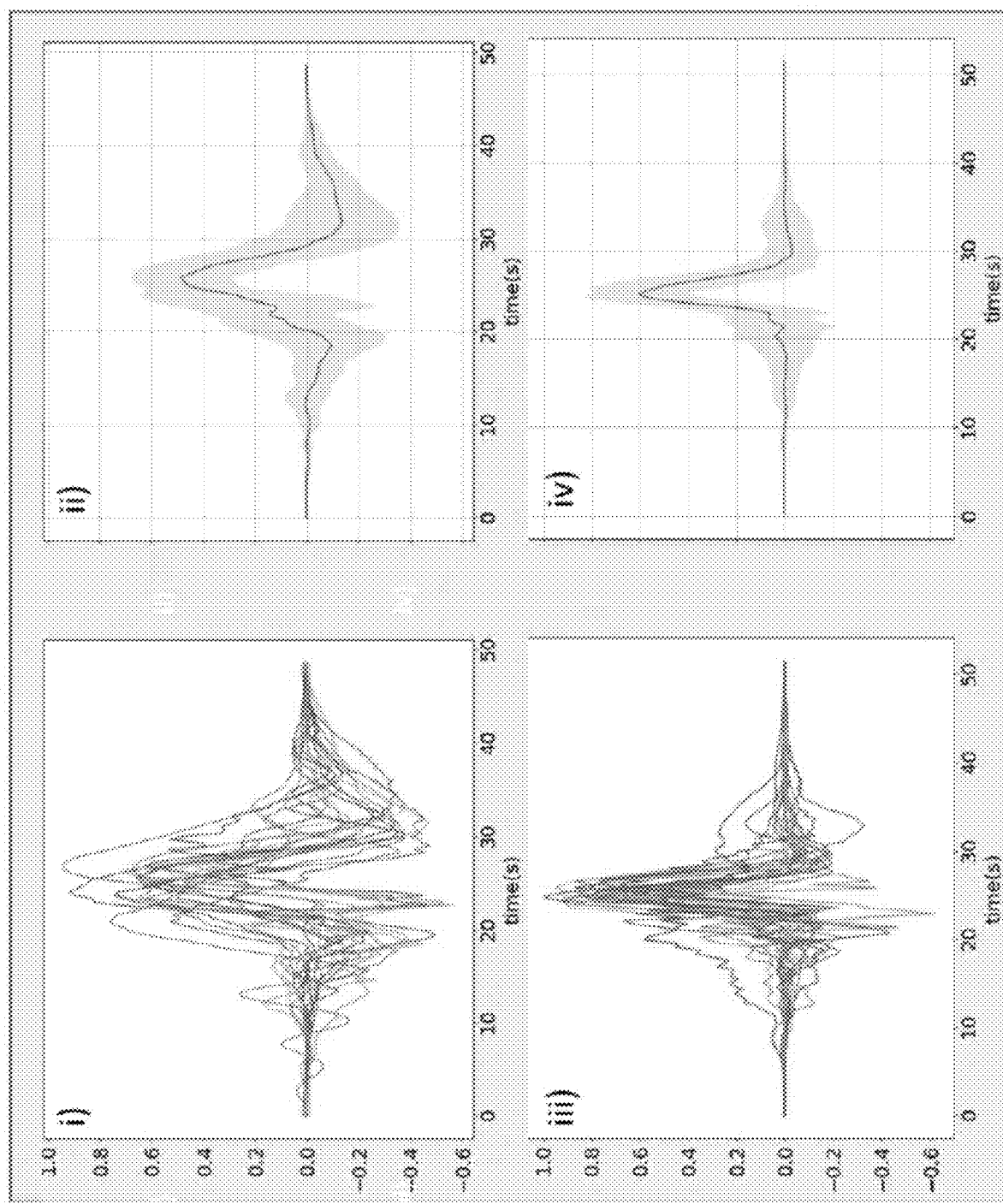
FIG. 4B provides graphs showing hemodynamic impulse response functions (HRFs) extracted from data by group-level fMRI encoder.
Figure 4C:
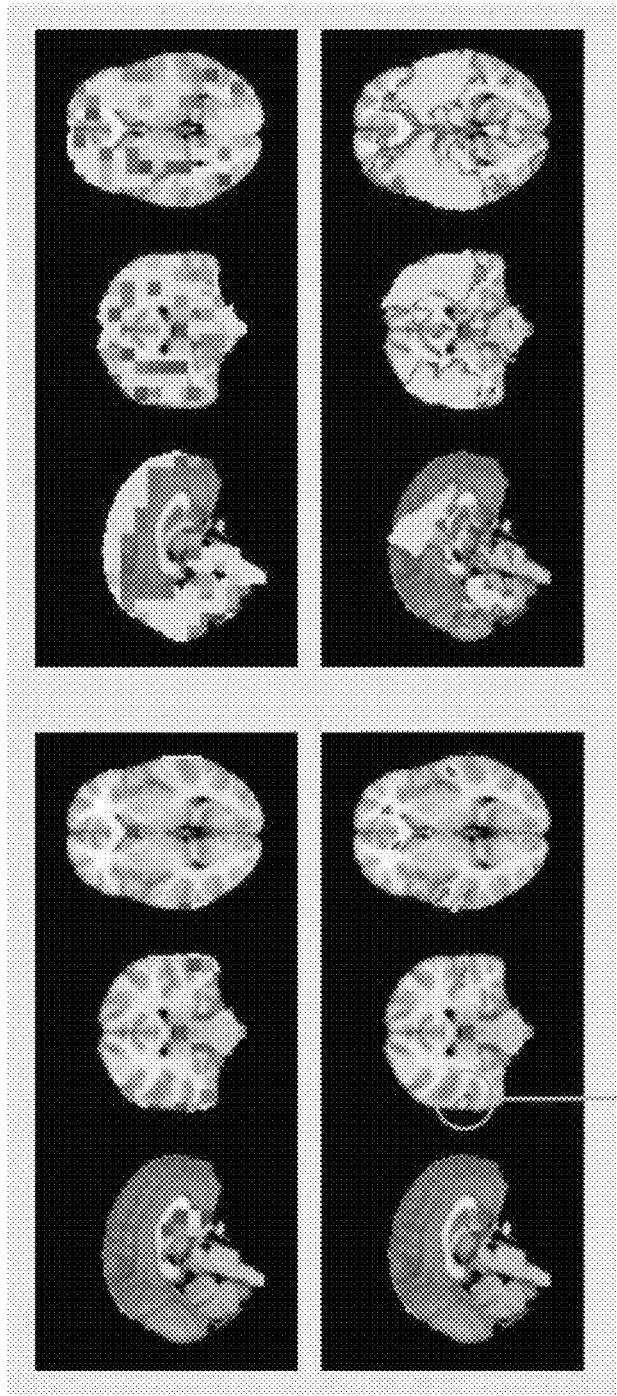
FIG. 4C provides images showing activation map generated from fMRI estimation generated from EEG for i) standard and ii) odd-ball stimulus compared with the correspondent iii) standard tone fMRI activation map and iv) odd-ball fMRI activation map ground truth.

(i) and (ii) of FIG. 4C show the group-level activation map generated from fMRI inferred from the EEG data of a subject that the model is not trained on. While it shows high similarity to the group-level activation map generated from real simultaneously acquired fMRI, the divergence indicates the existence of information that's captured by only one of the modalities but not both. The divergence suggests that the subject-wise difference plays an important role in the precision of the reconstructed super-resolution latent source space. The misalignment of the activation at the auditory cortex goes away in the final super-resolution latent source space reconstruction (FIG. 3) as the subject-level models correct the subject-level difference.

Example functions of each module in the group-level cyclic convolutional transcoder are listed:

fMRI decoder: Solve the fMRI blind deconvolution problem to decode the latent source space from fMRI.

EEG decoder: Solve the EEG blind signal separation problem to achieve source localization from channel-wise EEG recordings to 3D brain volume.

fMRI encoder: Convolve the latent source space with an HRF estimated from data to encode it to fMRI data.

EEG encoder: Mapping the latent source space signal from 3D brain volume to electrodes on the surface of the scalp through a forward head model(lead field matrix) estimated from the data to encode it to EEG data.

Figure 4D:
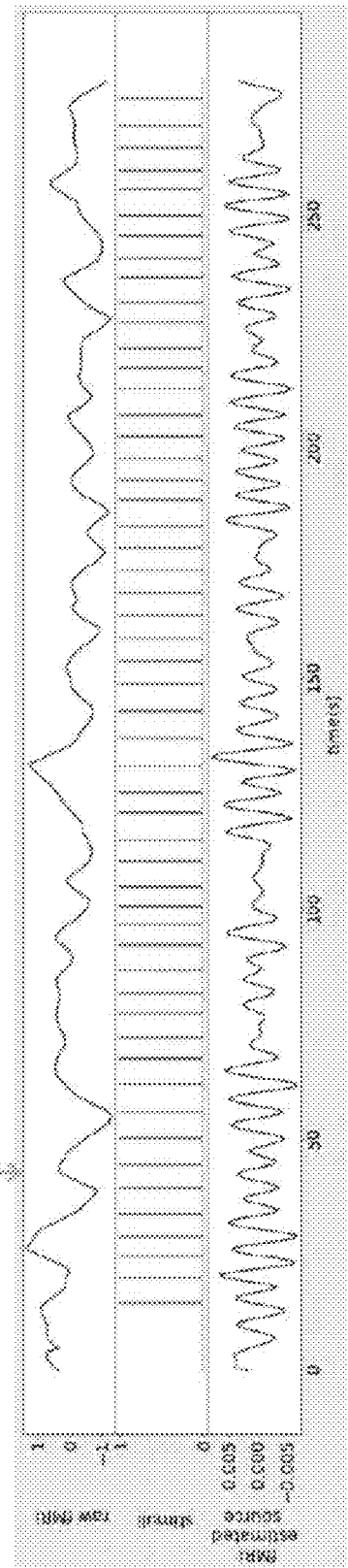
FIG. 4D provides a graph showing an fMRI estimated source generated by group-level fMRI decoder of one voxel in the auditory cortex.

The consistency of the disclosed system showed by the super-resolution latent source space in FIG. 2 and FIG. 3. In FIG. 4D, the BOLD signal was detected from one voxel in the auditory cortex (marked with green circle) of fMRI recording("raw fMRI") and deconvolve it with the group-level model's fMRI decoder. The resulted "fMRI estimated source" plotted with the stimuli shows peaks align with the auditory standard (in blue) and oddball (in orange) "stimuli," although no dependencies to "stimuli" are visible from the "raw fMRI."

Meanwhile, as fMRI encoder performs a convolution process to generate the fMRI estimation from the latent source space, the HRF was extracted from the fMRI encoder by inputting a unit impulse response to the fMRI encoder. FIG. 4B(i) shows the HRF extracted from 19 fMRI encoder of group-level models retrained with the leave-one-subject-out paradigm, while FIG. 4B(ii) is the mean of these HRFs plotted with 95% confidence interval. Although each retrains converges to a different local minimum, all of the HRFs shows a time scale of 20-30 seconds together with an initial dip and overshoot. The same experimental design was applied to the three-choice visual categorization dataset, and the result is shown in FIG. 4B (iii) and (iv).

Qualitative Evaluation: the training and testing mean square error of EEG-to-fMRI, fMRI-to-EEG transcoding and EEG-to-EEG and fMRI-to-fMRI cycle are shown in FIG. 5A. For reference, the normalized fMRI and EEG data used for training and testing are zero-mean and unit variance. To avoid overfitting, for both datasets, the early stop was performed during source reconstruction for the group-level model at 40 epochs and the subject-level model at 30 epochs. The test error of EEG-to-fMRI, fMRI-to-EEG transcoding reflects the disclosed model's ability to transcode from one modality to the other, while the high performance of EEG-to-EEG and fMRI-to-fMRI cycle indicates the consistency between EEG/fMRI estimated source space. To be noted is that, due to the low SNR nature of EEG/fMRI even after preprocessing, all of the training and testing errors shown are overestimation as the "ground truth" EEG/fMRI we are comparing with are noisy. Also, qualitative evaluation of real data super-resolution latent source space is not feasible due to the inaccessible nature of the ground truth latent source space.

A realistic simultaneous EEG-fMRI simulator was designed to evaluate the performance of the transcoder. The Vanilla transcoder can be made of EEG-to-fMRI and fMRI-to-EEG transcoder. Their performances are evaluated and shown in FIG. 5B(i) and FIG. 5B(ii), respectively. The performance was compared with the newly developed cyclic transcoder model. Performance improvement was detected in most cases. The performance of oscillating/sparse source reconstruction from fMRI/EEG is shown in FIG. 5B(iii) and FIG. 5B(iv), respectively. The performance of EEG source reconstruction (result of the new cyclic transcoder) is shown in FIG. 5B (v). The performance of the EEG source compared that with the classic L-2 norm EEG sourcing method. See FIG. 5B (vi). Since simulated data was used, the classic method has certain advantages, as it can provide the ground truth head conductivity model (leadfield matrix). However, the cyclic model still showed better EEG source reconstruction performance for both oscillating and sparse sources.

The disclosed techniques can extract an activation map every 10 ms, while considering fMRI of TR=2s, its activation map can be considered as 2s collapsed together and thus has a statistical power 200 times that of our method. Because of that, the super-resolution latent source space can fail to show some of the activation/deactivations that show in an fMRI activation map under the same threshold with the same number of trials. Also, it can show some of the activation/deactivation during the task that cancels out with each other due to the collapsing nature of fMRI.

FIG. 3 shows the potential of reconstructing the super-resolution latent source space from EEG/fMRI when only one of the modalities is available. It shows that with about 1-hour simultaneous EEG-fMRI data, the subject-level model can be trained to be applied to the same subject's other EEG/fMRI-only data to solve EEG source localization or fMRI deconvolution issues. This can be beneficial to cognitive/behavior assessments and clinical applications that require EEG source localization and fMRI deconvolution with only EEG/fMRI recordings. The disclosed system can also promote the development of technologies that require accurate EEG source localization or fMRI deconvolution, such as brain-computer interface(BCI).

As a proof of concept assessment, neither subject-wise difference nor meaningful task-related brain dynamics were incorporated in the realistic simultaneous EEG-fMRI simulation. As the subject-level transcoder aims to resolve subject-wise differences and requires data epoched by task onset, the group-level transcoder was assessed on the simulated data.

The disclosed system can provide simultaneously acquired EEG-fMRI modality fusing. The disclosed paradigm can be applied to other scenarios not only in medical imaging like simultaneously acquired EEG-fMRIs, but also in other fields like remote sensing and self-driving car in which multiple types of sensors simultaneously record signals of very different nature and spatial/temporal resolutions, even with high-dimensional and valuable data.

The relationship between EEG/fMRI and the latent source space can be described by the following models:

$$E = GX + N_E \qquad (1)$$

$$F = X \cdot b + N_F \qquad (2)$$

As shown in equation (1), EEG signal E can be considered as a linear mixing of the source X through a leadfield matrix G. NE is the noise term. On the other hand, in equation (2), fMRI signal F can be considered as the source X convolved with a hemodynamic response function (HRF) h. NF is the noise term.

Simultaneous EEG-fMRI source space fusion can be formatted as an optimization problem. However, the optimization problem can be solvable when a very accurate estimation of leadfield matrix G is provided, and hemodynamic response function h is available, which is difficult to fulfill.

When information of the leadfield matrix G is not available, estimating source X from EEG signal E according to the model shown in equation (1) can be considered as a blind signal separation (BSS) problem. When an accurate estimation of hemodynamic response function h is not available, based on the model shown in equation (2), estimating source X from fMRI can be a blind deconvolution problem with an unknown convolutional kernel. Although both BSS and blind deconvolution are difficult problems to solve, fortunately, deep learning as a fast-developing field shows the state-of-the-art performance for both problems.

Hierarchical deep transcoding for modality fusing: The disclosed subject matter provides the possibility of solving this modality fusing problem with deep learning. The disclosed subject matter can also address the following issues: First, valuable data: Simultaneous EEG-fMRI data is very valuable compared to ordinary deep learning applications.

With such a small dataset, a deep learning model can be vulnerable to overfitting. Secondly, high dimensionality: The dimensionalities of the data can be extremely high. A dimensionality of a 10 min fMRI episode can be 64×64×35×300. As the simultaneously acquired EEG can have a sampling rate of 1000 Hz. A sampling rate at least up to 60 Hz can be considered as a meaningful signal, if the information is kept up to 100 Hz, a dimensionality can be 64×60,000. To reach EEG's effective temporal resolution and fMRI's spatial resolution, the reconstructed source space can be 64×64×35×60, 000. This is a challenge to storage and computational resources for the deep learning method. Thirdly, large upsampling factor: as fMRI has low temporal resolution and EEG lacks spatial specificity, to reach EEG's effective temporal resolution and fMRI's spatial resolution, fMRI can be upsampled from about 0.5 Hz to 100 Hz. EEG can also be upsampled from about 64 channels to a 64×64×35 volume. These high upsampling factors can request a conventional super-resolution deep learning model to have a large receptive field and consequently more parameters, which can cause the overfitting issue due to limited data. Subject-wise difference: As mentioned in section 1, due to subject-wise difference, a group-level model is not necessarily accurate enough to resolve the source space to the spatial resolution of 2 mm and temporal resolution of 100 Hz. Meanwhile, training a deep learning model for each subject can be unrealistic as the data for each subject is even more limited.

Due to the difficulties listed above, the framework disclosed in FIG. 1 is designed to address the difficulties. FIG. 1A is the overall pipeline of the hierarchical deep transcoding model. The hierarchical deep transcoding model is made of two stages. In the first stage, a group-level model can be trained on all of the data from different subjects to reach an intermediate spatial/temporal resolution for EEG and fMRI, respectively. The group-level EEG estimated source can have a higher spatial resolution than the original EEG but lower spatial resolution than the desired super-resolution latent source space, namely, the spatial resolution of the original fMRI. The group-level fMRI estimated source can have a higher temporal resolution than the original fMRI, but lower temporal resolution than the desired super-resolution latent source space, that is, the temporal resolution of the original EEG. In the second stage, a subject-level model can be trained for each subject's data to finally reach the desirable spatial/temporal resolution of super-resolution latent source space.

In the group-level model, the simultaneous EEG and fMRI data after preprocessing first go through spatial/temporal linear interpolation to reach the intermediate spatial/temporal resolution. Then, the interpolated EEG/fMRI data can be temporally/spatially reduced respectively so both of them can have the same intermediate spatial/temporal resolution of around 12 mm/2.7 Hz (e.g., specific intermediate spatial/temporal resolution choices can be different considering fMRI's slice-timing setting) for training the group-level model. EEG's temporal resolution and fMRI's spatial resolution can be reduced to achieve a "middle ground" to train the group-level model. However, during inferring, the EEG/fMRI were no longer temporal/spatial block reduced. Instead, the model was applied to each time point/3D volume of EEG/fMRI, respectively. This allows maintaining all of EEG/fMRI's temporal/spatial information, respectively. The assembled group-level EEG estimated source included spatial/temporal resolution of 12 mm/100 Hz, and the assembled group-level fMRI estimated source included spatial/temporal resolution of 2 mm/2.7 Hz.

In the subject-level model, the group-level EEG/fMRI estimated source can be epoched according to task onsets to achieve 3D event-related potential(ERP) representations in 100 Hz after the group-level EEG estimated source is spatially linear interpolated to 2 mm. Epoching can be necessary, as the group-level fMRI estimated source of 2.7 Hz can otherwise become extremely information sparse if linearly interpolated to 100 Hz. By taking advantage of the jittering nature of the event onset of the experimental design, epoched group-level fMRI estimated source can have denser information. Also, it can improve the signal-to-noise ratio of group-level EEG/fMRI estimated source. Then, the epoched group-level EEG/fMRI estimated source can be both sliced in spatial and temporal direction for training a subject-level model for each single subject. During inferring, again the model can be applied to each time point/3D volume for EEG/fMRI, respectively. After assembling, both the subject-level EEG/fMRI estimated source can have the desired spatial and temporal resolution of super-resolution latent source space. The spatial and temporal resolution can be separately analyzed or simply by adding them together to achieve the super-resolution latent source space, as shown in FIG. 2.

The cyclic convolutional transcoder, as shown in FIG. 1B, can be the core of the hierarchical deep transcoding structure. Both the group-level model and the subject-level model take the shape of a cyclic convolutional transcoder. However, the subject-level model can be a non-fine-tune of the group-level model, as their inputs are data of different scales. So the subject-level model can require re-initialization of the parameter during training and be trained on top of the group-level model's parameter. The cyclic convolutional transcoder can include four modules (e.g., fMRI decoder, fMRI encoder, EEG decoder, and EEG encoder). Both EEG and fMRI can be considered as an encoding of the latent source space. So a decoder can decode the latent source space from an encoding(EEG/fMRI), while an encoder can encode the latent source space into an encoding(EEG/fMRI). The loss function is shown in equation (3).

$$loss_{total} = \sum_{i=1}^{4} loss_i \quad (3)$$

where $$\text{fMRI-to-EEG transcoding loss: } loss_1 = \sum_{i=1}^{n} (E_i - \hat{E}_i)^2$$

$$\text{EEG-to-fMRI transcoding loss: } loss_2 = \sum_{i=1}^{n} (F_i - \hat{F}_i)^2$$

$$\text{fMRI-to-fMRI cycle consistency loss: } loss_3 = \sum_{i=1}^{n} (F_i - \hat{F}'_i)^2$$

$$\text{EEG-to-EEG cycle consistency loss: } loss_4 = \sum_{i=1}^{n} (E_i - \hat{E}'_i)^2$$

The fMRI/EEG decoder can be made of only transpose temporal/spatial convolutional layers, while the fMRI/EEG encoder can be made of only temporal/spatial convolutional layers, respectively. This can ensure the fMRI encoder/decoder only applies the temporal transformation to the original fMRI data, and the EEG encoder/decoder only applies a temporal transformation to the original EEG data. The same rule can apply to group-level and subject-level models equally. This particular design can ensure that the temporal/spatial information of EEG/fMRI is well maintained by the model respectively, but also achieves an interpretable model.

Data Collection and Preprocess-Auditory Odd-ball Task Dataset: the disclosed method was evaluated using simultaneously acquired EEG-fMRI data from 19 subjects. The data were recorded while subjects performed an auditory oddball task, which included 80% standard and 20% oddball (target) stimuli. Standard stimuli were pure tones with a frequency of 350 Hz, while the oddball stimuli were broadband (laser gun) sounds. Stimuli lasted for 200 ms with an inter-trial interval (ITI) sampled from a uniform distribution between 2 s and 3 s. Subjects were instructed to ignore standard tones and respond to oddball sounds as quickly and as accurately as possible by pressing a button. Every subject was scheduled to complete five sessions in total (105 trials per session), with an average of 4.6 sessions per subject included in this study (range between 2 to 5, standard deviation of 0.98).

MR data were recorded inside a 3 T Siemens Prisma scanner, with a 64 channel head/neck coil, and EEG was recorded using a 64 channel BrainAmp MR Plus system. (1) Structural T1 images were acquired with an echo time (TE) of 3.95 ms, a repetition time (TR) of 2300 ms, and a flip angle of 9 degrees (FA). Images were acquired with a field of view (FOV) of 176×248 voxels, at a voxel size of 1×1×1 mm. (2) Functional Echo Planar Imaging (EPI) images were acquired with a TE of 25 ms, a TR of 2100 ms, and an FA of 77 degrees. Images were acquired with a FOV of 64×64 voxels, at a voxel size of 3×3×3 mm. (3) One single-volume high-resolution EPI image was acquired with a TE of 30 ms, a TR of 6000 ms, and an FA of 90 degrees. Images were acquired with a FOV of 96×96 voxels, at a voxel size of 2×2×3 mm.

For EEG data-processing, raw EEG data was imported with EEGLAB toolbox and low-pass filtered with a cutoff frequency of 70 Hz by a non-causal finite impulse response (FIR) filter. An fMRI Artifact Slice Template Removal algorithm (FASTR) was used for gradient artifact removal. EEG data were then resampled to 500 Hz. To reduce ballistocardiogram (BCG) artifacts, the FMRIB EEGLAB plugin was used. The 500 Hz EEG data was high-pass filtered at 0.25 Hz with another FIR filter to reduce electrode drift before QRS complex detection was performed on it. The generated QRS complex event times were used to remove the BCG effect of another copy of the 500 Hz EEG data (not high-pass filtered), with the FMRIB plugin's BCG suppression function set to Optimal Basis Set (OBS) mode with the number of bases set to four (the default). This can be a widely accepted standard pipeline for EEG data preprocessing when it's acquired simultaneously with fMRI data. Then the 63 channel EEG data are assigned to a 3D volume.

fMRI data were preprocessed using FEAT analysis from the FSL toolbox. Specifically, a brain/background threshold was set at 10%, and a high-pass filter with a cutoff at 60s was applied. Spatial smoothing and FSL's built-in interleave slice-timing correction was disabled. Spatial normalization was achieved by first registering the fMRI data to a high-resolution functional image which is then registered to the structural image (T1) and finally to a standard space image. The fMRI data after spatial normalization is with a FOV of 90×108×90 voxels, at a voxel size of 2×2×2 mm.

Three-choice (Face vs. Car vs. House) Visual Categorization Task Dataset: 21 subjects (12 male, 9 female; age range 20-35 years) participated in the study. The Columbia University Institutional Review Board (IRB) approved all experiments, and informed consent was obtained before the start of each experiment. All subjects had a normal or corrected-to-normal vision.

A set of 30 faces (from the Max Planck Institute face database), 30 cars, and 30 house (obtained from the web) grayscale images (image size 512×512 pixels, 8 bits/pixel) were used. They all had identical magnitude spectra (average magnitude spectrum of all images in the database), and their corresponding spectra were manipulated using the weighted mean phase (WMP) technique to generate a set of images characterized by their % phase coherence. The stimulus evidence (high or low) for each trial was systematically varied by modifying the salience of the image via randomization of image phase at either 35% (low) or 50% (high) coherence.

The stimuli were used in an event-related three choice reaction time task. On each trial, an image of either a face, car, or house was presented for 50 ms, and subjects were instructed to respond with the category of the image by pressing one of three buttons on an MR compatible button controller. Stimuli were presented to subjects using E-Prime software (Psychology Software Tools) and a VisuaStim Digital System (Resonance Technology) with a 600×800 goggle display. Images subtended 11o×8o of visual angle. Over four runs, a total of 720 trials were acquired (240 of each category with 120 high coherence trials) with a random inter-trial interval (ITI) sampled uniformly between 2-4s. Each run lasted for 560 seconds.

Blood-oxygenation-level-dependent (BOLD) T2-weighted functional images were acquired on a 3T Philips Achieva scanner using gradient-echo echo-planar imaging (EPI) pulse sequence with the following parameters: Repetition time (TR) 2000 ms, echo time (TE) 25 ms, flip angle 90, slice thickness 3 mm, interslice gap 1 mm, in-plane resolution 3×3 mm, 27 slices per volume, 280 volumes. For all of the participants, a standard T1-weighted structural MRI scan (SPGR, resolution 1x1x1mm) was acquired.

EEG was simultaneously and continuously recorded using a custom-built MR-compatible EEG system, with differential amplifiers and bipolar EEG montage. The caps were configured with 36 Ag/AgCl electrodes, including left and right mastoids, arranged as 43 bipolar pairs.

Image preprocessing was performed with FSL. Functional images were spatially realigned to the middle image in the times series (motion-correction), corrected for slice time acquisition, spatially smoothed with a 6 mm FWHM Gaussian kernel, and high pass filtered (100s). The structural images were segmented (into grey matter, white matter and cerebrospinal fluid), bias-corrected and spatially normalized to the MI template using FAST. Functional images were registered into MI space using boundary-based registration (BBR).

Standard EEG preprocessing offline was performed using MATLAB (Math-Works) with the following digital Butterworth filters: 0.5 Hz high pass to remove direct current drift, 60 and 120 Hz notches to remove electrical line noise and its first harmonic, and 100 Hz low pass to remove high-frequency artifacts not associated with neurophysiological processes. These filters were applied together in the form of a zero-phase finite impulse response filter to avoid distortions caused by phase delays. Stimulus-locked 1500 ms epochs (−500:1000) were extracted and subtracted the mean baseline (−200:0) from the rest of the epoch. Through visual inspection, trials containing motion and/or blink artifacts, evidenced by sudden high-amplitude deflections, were discarded.

Figure 7:
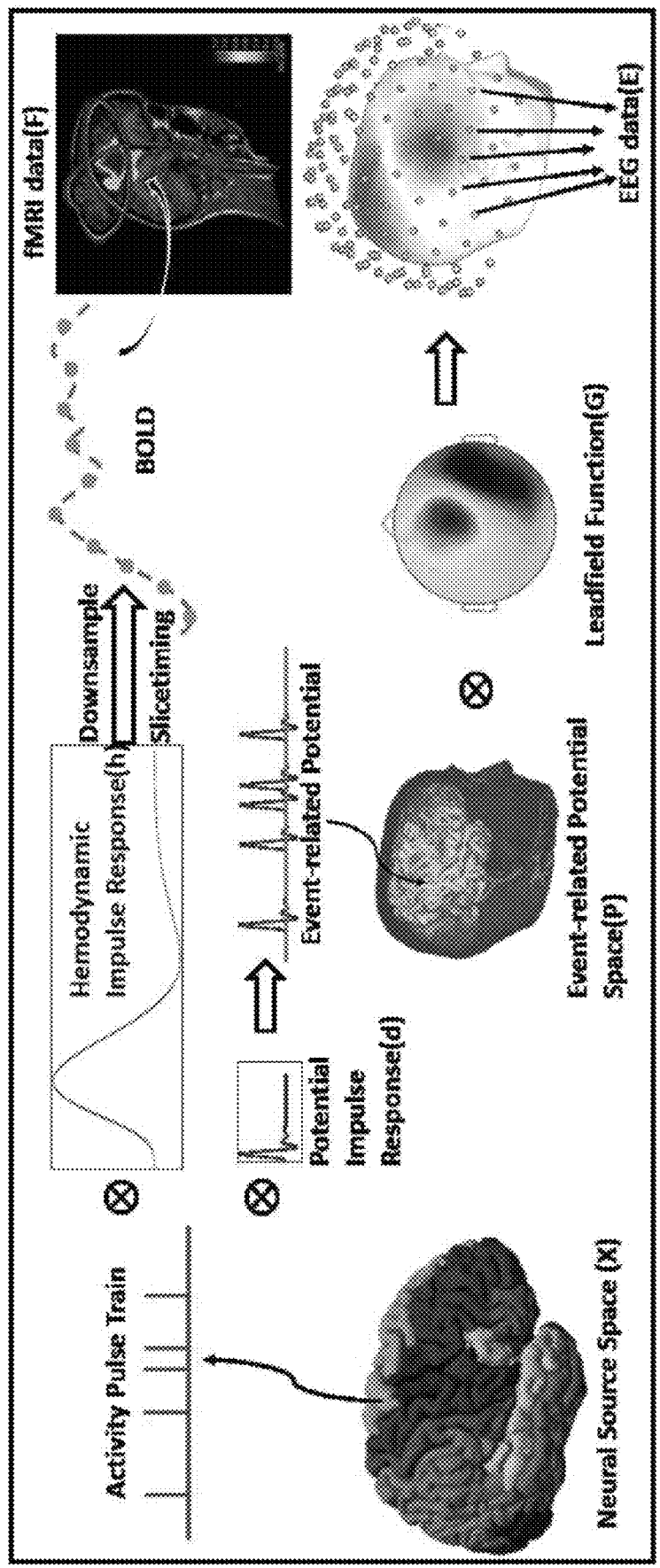
FIG. 7 provides a diagram showing an example framework for simulation of simultaneous EEG-fMRI data in accordance with the disclosed subject matter.
Figure 8:
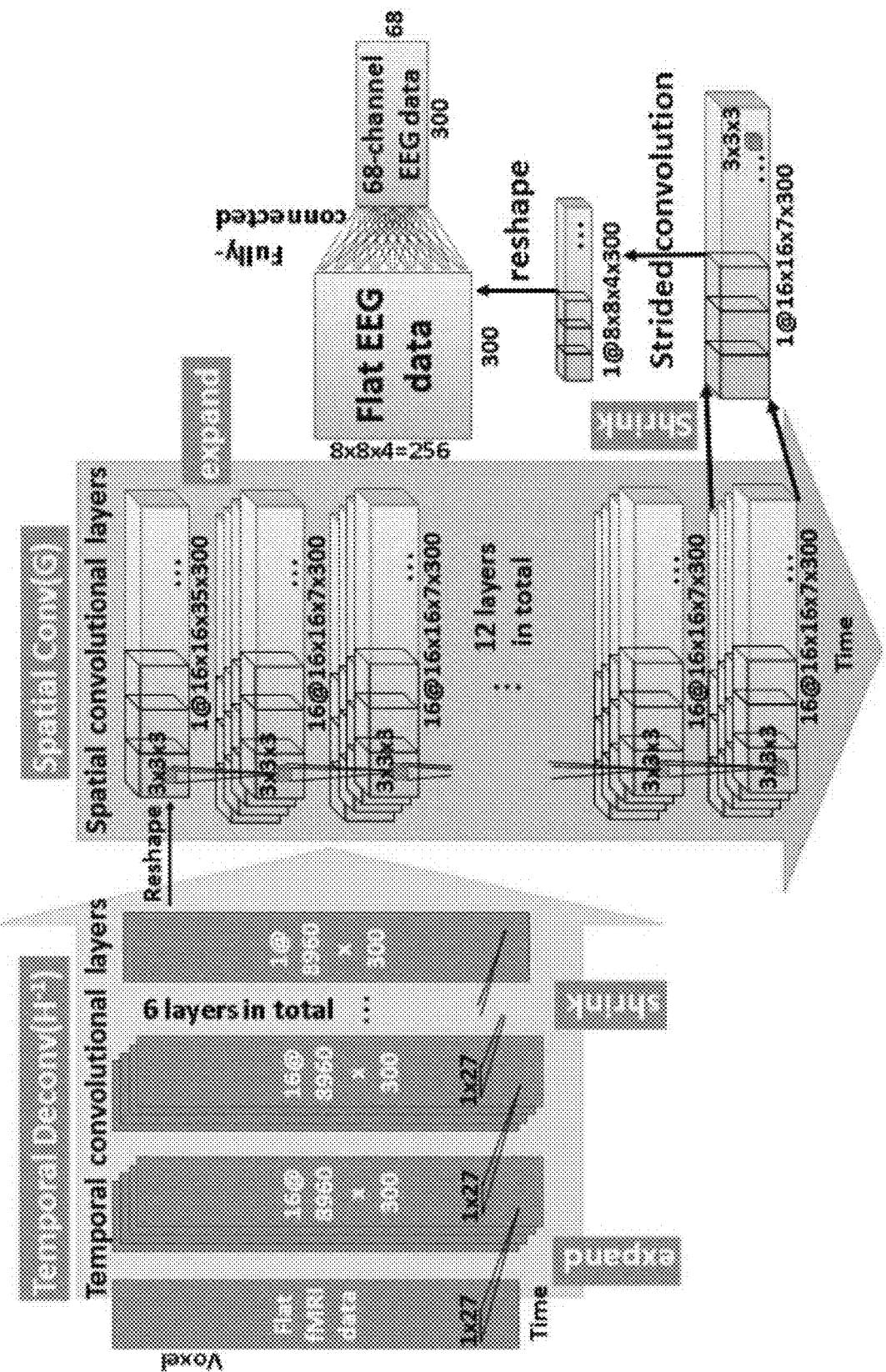
FIG. 8 provides a diagram showing an example fMRI-to-EEG transcoder in accordance with the disclosed subject matter.
Figure 9:
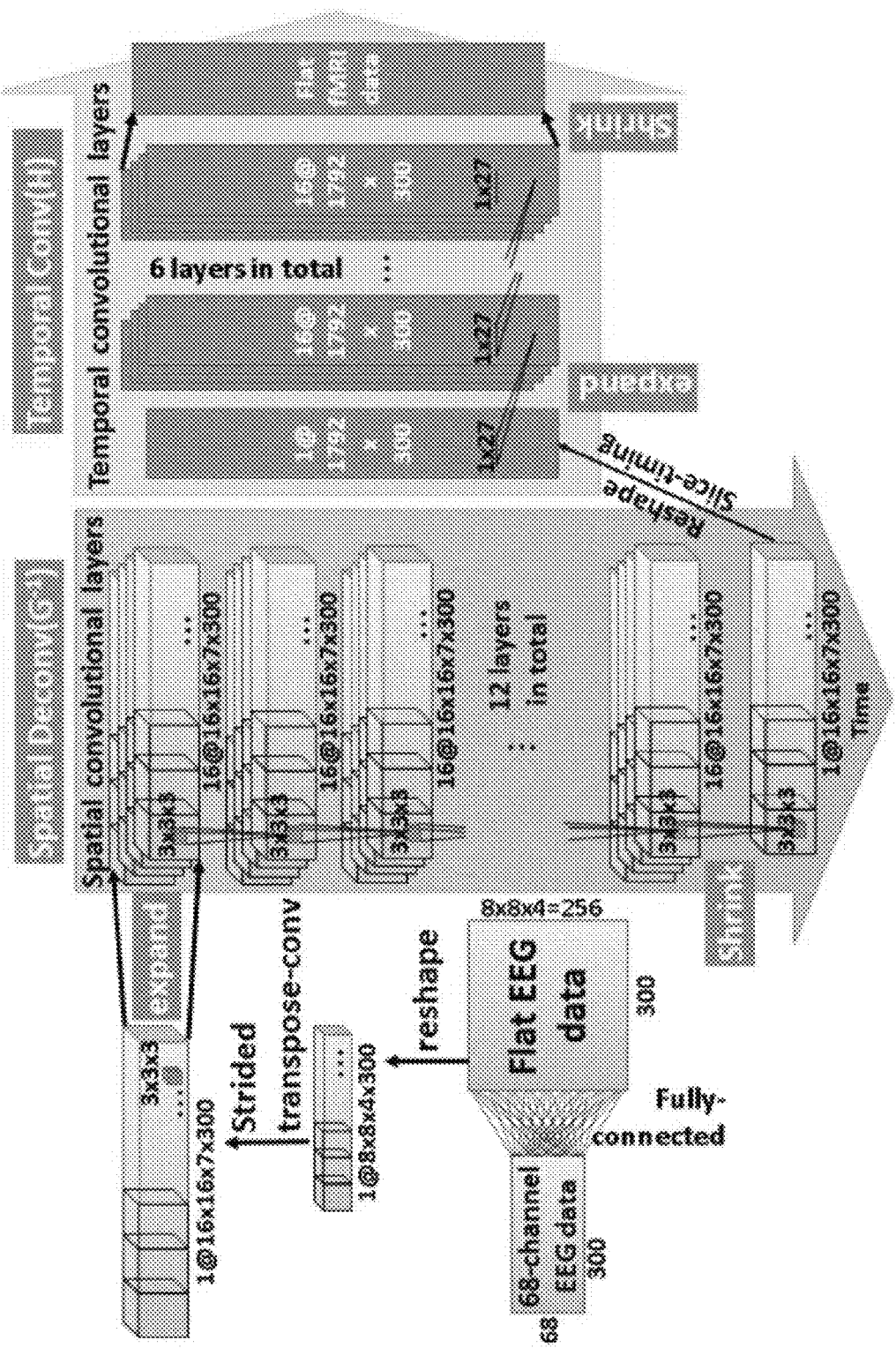
FIG. 9 provides a diagram showing an example EEG-to-fMRI transcoder in accordance with the disclosed subject matter.
Figure 10:
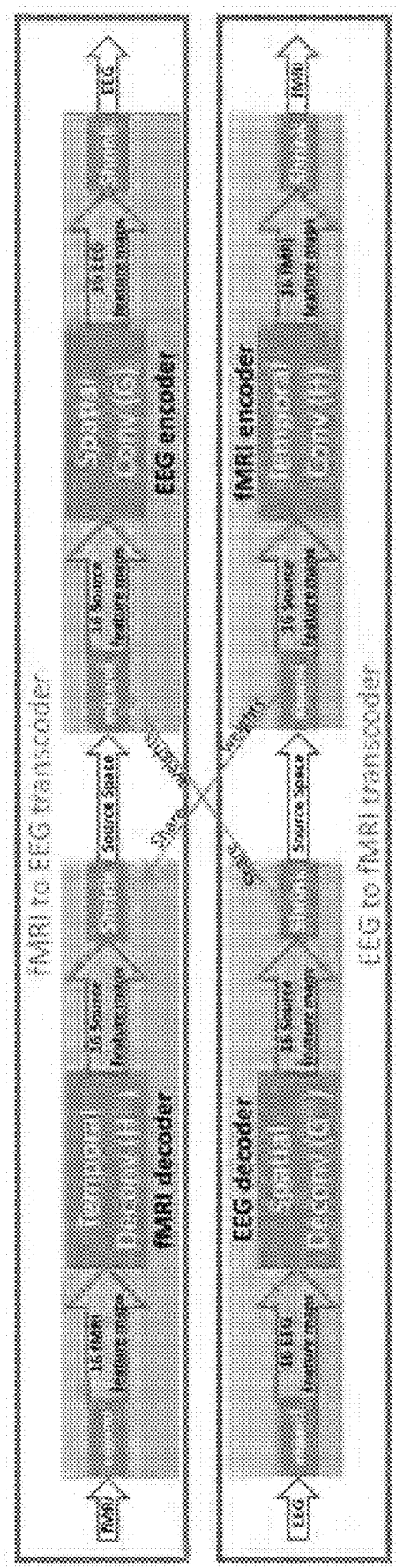
FIG. 10 provides a diagram showing an example framework of a bidirectional vanilla transcoder in accordance with the disclosed subject matter.
Figures 1, 11:
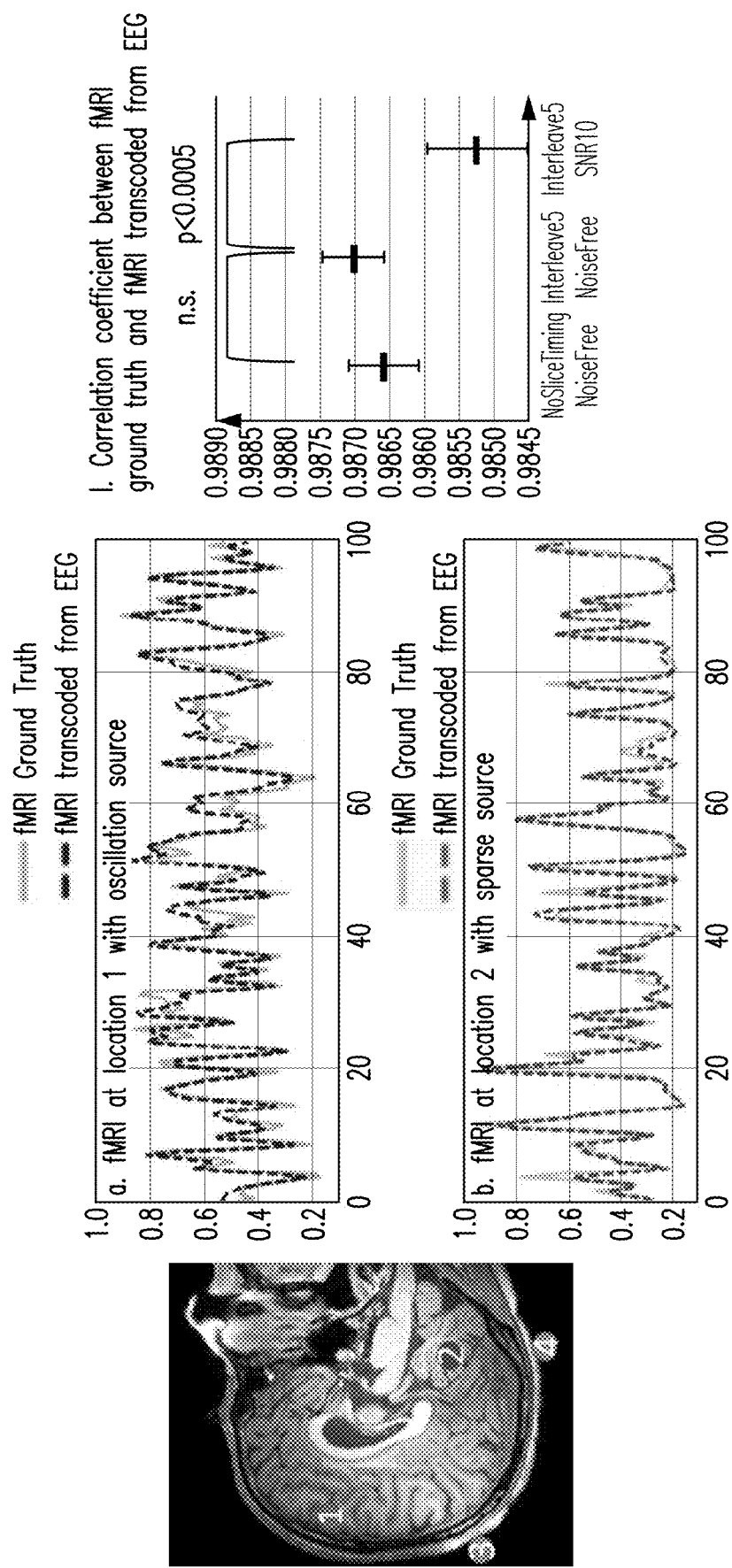
FIG. 11 provides graphs and images showing transcoder predictions relative to ground truth in accordance with the disclosed subject matter.
Figures 2, 11:
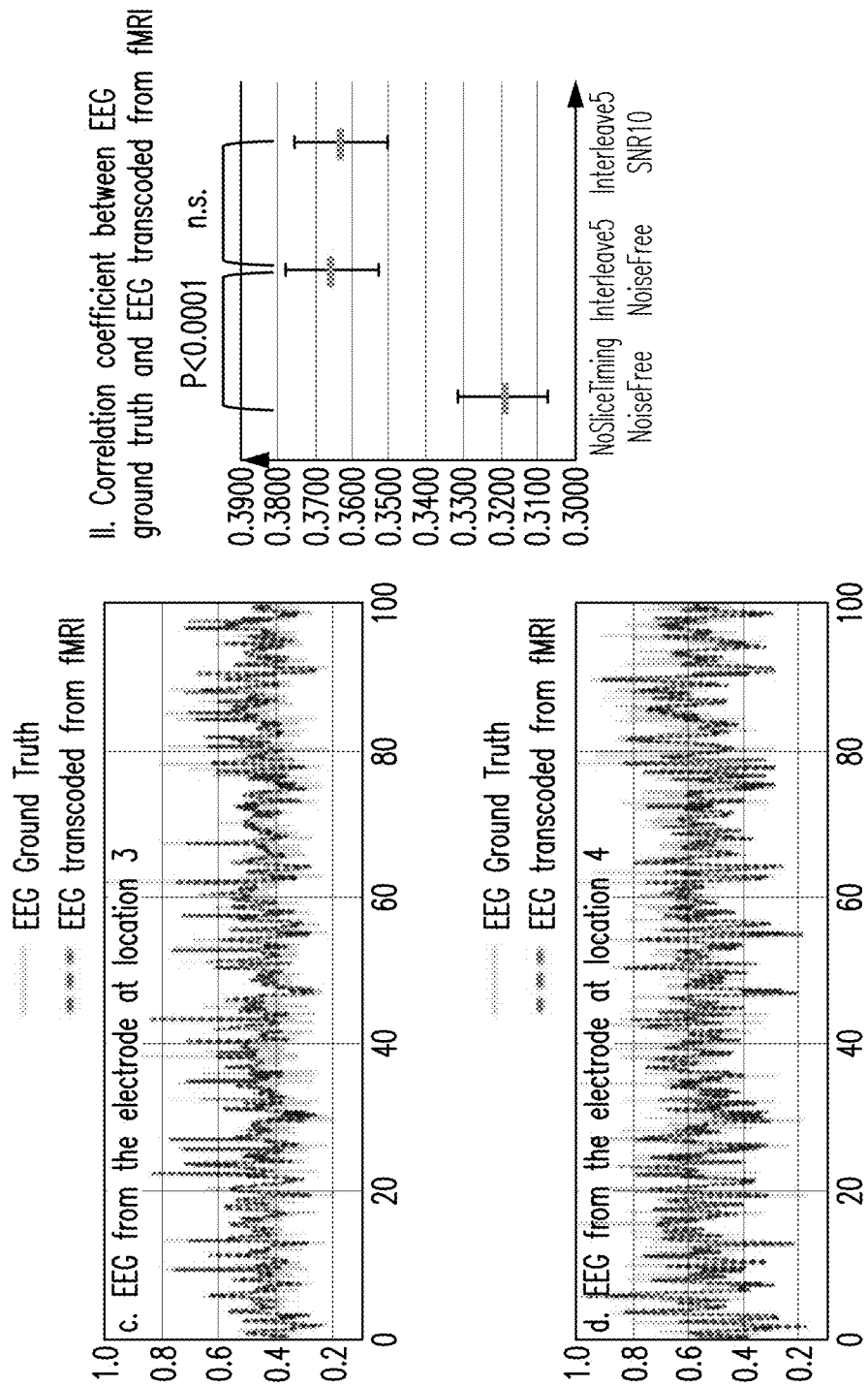
Figures 3, 11:
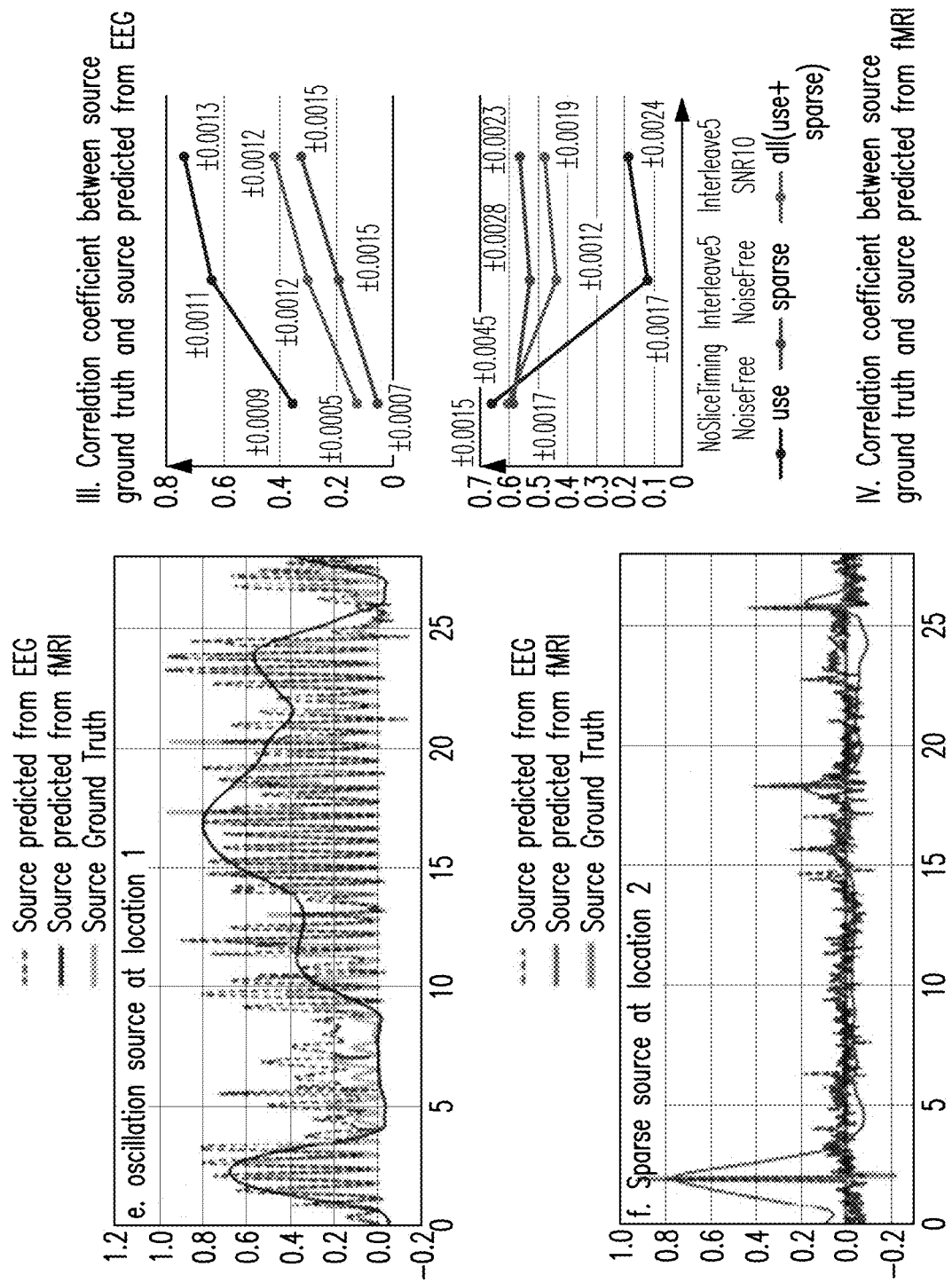

A simultaneous EEG-fMRI simulator: One of the challenges to develop a method for reconstructing the source from EEG and fMRI can be the absence of the latent source space ground truth of real simultaneous EEG-fMRI data, which makes it hard to evaluate any potential method on real data. To eliminate this potential obstacle, a simultaneous EEG-fMRI simulator was developed, as shown in FIG. 7.

The disclosed simulator can simulate the latent source space first and generate the EEG and fMRI data from the simulated latent source space. These simulations can allow access to ground-truth to determine the accuracy of the recovered source spaces. When there are neural sources X at specific spatial locations in the brain, the disclosed simulator can assign these neural sources to cortical and subcortical areas base on Freesurfer segmentation of a subject's structural image (T1) registered to his/her corresponding functional image (T2*) space. In the disclosed simulation, the activity of these sources was represented as a series of impulse signals, representing evoked responses. On top of those evoked responses, oscillatory activity was added, across various frequency ranges, to different areas of the brain (e.g., 0.5 Hz-3 Hz: gyrus rectus, 3 Hz-8 Hz: inferior temporal cortex and superior temporal cortex, 8 Hz-12 Hz: lateral occipital cortex, 12 Hz-38 Hz: superior parietal cortex, and 38 Hz-42 Hz: post central cortex).

The simulated source space data is of size 64×64×35 and sampled at a frequency of 105 Hz. The fMRI signal was estimated and simulated using equation (2). F is the hemodynamic response and is modeled as the activity of the sources X convolved with a hemodynamic impulse response function (HRF) h following the linear model. A canonical HRF lasting 30s and peaking at 5s was used. The hemodynamic response signal F was sampled as a volume every 2 seconds (i.e., TR=2) according to slicetiming settings. Data was simulated without slicetiming (all slices acquired at the same time) and interleave 5 slicetiming to explore the effect of slicetiming on the disclosed model. fMRI signals also have noise, which was modeled as $N_F$. Specifically, respiratory noise was simulated with a saw-tooth signal and background noise with zero-mean Gaussian noise across the brain. Cardiac noise was simulated with a sinusoidal signal and its energy varies according to mean T2* intensity, so that areas of blood vessels have stronger cardiac noise.

The simultaneously acquired event-related potential P can be modeled as a convolution between the source signals X and the "potential impulse response" d using equations (4) and (5):

$$P = X * d \qquad (4)$$

$$E = GP \qquad (5)$$

Relative to h used to generate the fMRI signal, d is a much faster impulse response of around 470 milliseconds. The EEG signals measured at the scalp, E, represent a transformation of P by a matrix G commonly referred to as the "leadfield." The leadfield captures the conductivity of the human head. The disclosed simulation used the FieldTrip toolbox to generate a realistic leadfield matrix using the Boundary Element Method (BEM). The linear generative model of the simulated, simultaneously acquired EEG-fMRI is summarized in FIG. 7.

Evaluate transcoding algorithms: 319 runs of 600 second simultaneous EEG-fMRI data were simulated. Data were cut into 30 second chunks with 50% overlap. 300 of 319 runs were used for training the model, the remaining 19 runs were used for testing the model. The simulated data were used in evaluating the transcoding algorithm.

Evaluate slice-timing correction algorithms: As the disclosed simulator can simulate different slice-timing settings of fMRI. The disclosed simulator was also used to test the performance of different slice-timing correction methods and shows "Optimal slice timing correction" resulted in higher t-statistics over all noise conditions, as well as low and medium motion conditions. Motion proved to be the largest source of contamination in the simulated data, and also greatly reduced the effectiveness of all STC techniques. The disclosed subject matter provides a realistic simultaneous EEG-fMRI simulator. The disclosed simulator can be used with other simulator (e.g., POSSUM) for realistic dynamic brain fMRI simulation with spin history artifacts. For example, based on Bloch equations, the temporal mean of the fMRI $S_{mean}$ and BOLD activity $S_{activity}$ can be modeled as following respectively:

$$S_{mean} = S_0 \exp\left(-\frac{T_E}{T^*_{2(mean)}}\right) \qquad (6)$$

$$S_{activity} = S_0 \exp\left(-\frac{T_E}{T^*_{2(activity)}}\right) \qquad (7)$$

From equations (7) and (8), equation (9) can be derived:

$$\Delta\left(\frac{1}{T^*_2}\right) = \frac{1}{T^*_{2(activity)}} - \frac{1}{T^*_{2(mean)}} = \frac{1}{T_E}\ln\left(\frac{S_{mean}}{S_{activity}}\right) \qquad (9)$$

The final output of POSSUM can be:

$$s_i(r_0, t) = p(j) \int \int \int_{V_r 0} |M_{xy}(t_0)| \exp\left(-\int_{t_0}^{i} \frac{1}{T^*_2(t)} dt\right) \qquad (10)$$
$$\times \exp\left(-i\gamma \int_{t_0}^{i} G(g) \cdot (R(t)r + T(t)) dt\right)$$
$$\times \exp\left(-i\gamma \int_{t_0}^{i} (\tilde{B}_p(r_0, t) + \tilde{G}^P(r_0 \cdot t) \cdot (r - r_0)) dt\right) dr$$

The only term relevant to BOLD activity and physiological noise is $1/(T_2^*(t))$, whose changes is modeled in equation (10) and is dependent on the ratio between $S_{mean}$ and $S_{activity}$. $S_{mean}$ is a real subject's data by temporally averaging all its volumes, $S_{activity}$ is the linear combination BOLD signal, Cardiac Noise, and Respiration noise. The C++ source code of POSSUM was modified so it takes $\Delta(1/T_2^*)$ instead of the original $\Delta T_2^*$ as input. The simulated data reflects the interaction between BOLD activity, physiological noise and the artifacts caused by MRI machine such as rigid-body motion effects, B0-field inhomogeneities, chemicalshift, and eddy currents.

Figure 6A:
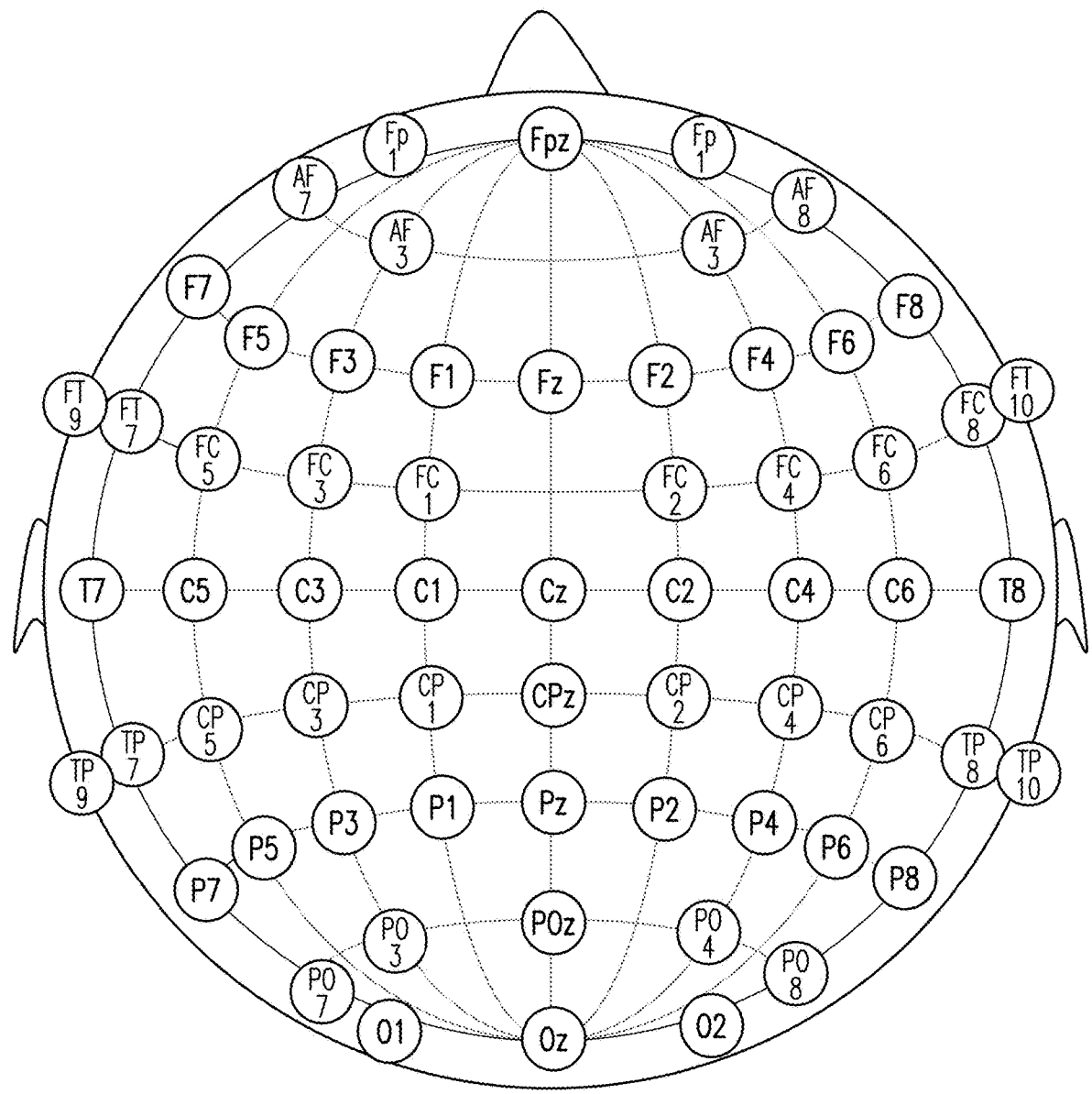
FIGS. 6A and 6B provide diagrams showing the assignment of the 63 EEG electrodes channel data to a 11×9×5 3D volume in accordance with the disclosed subject matter.
Figure 6B:
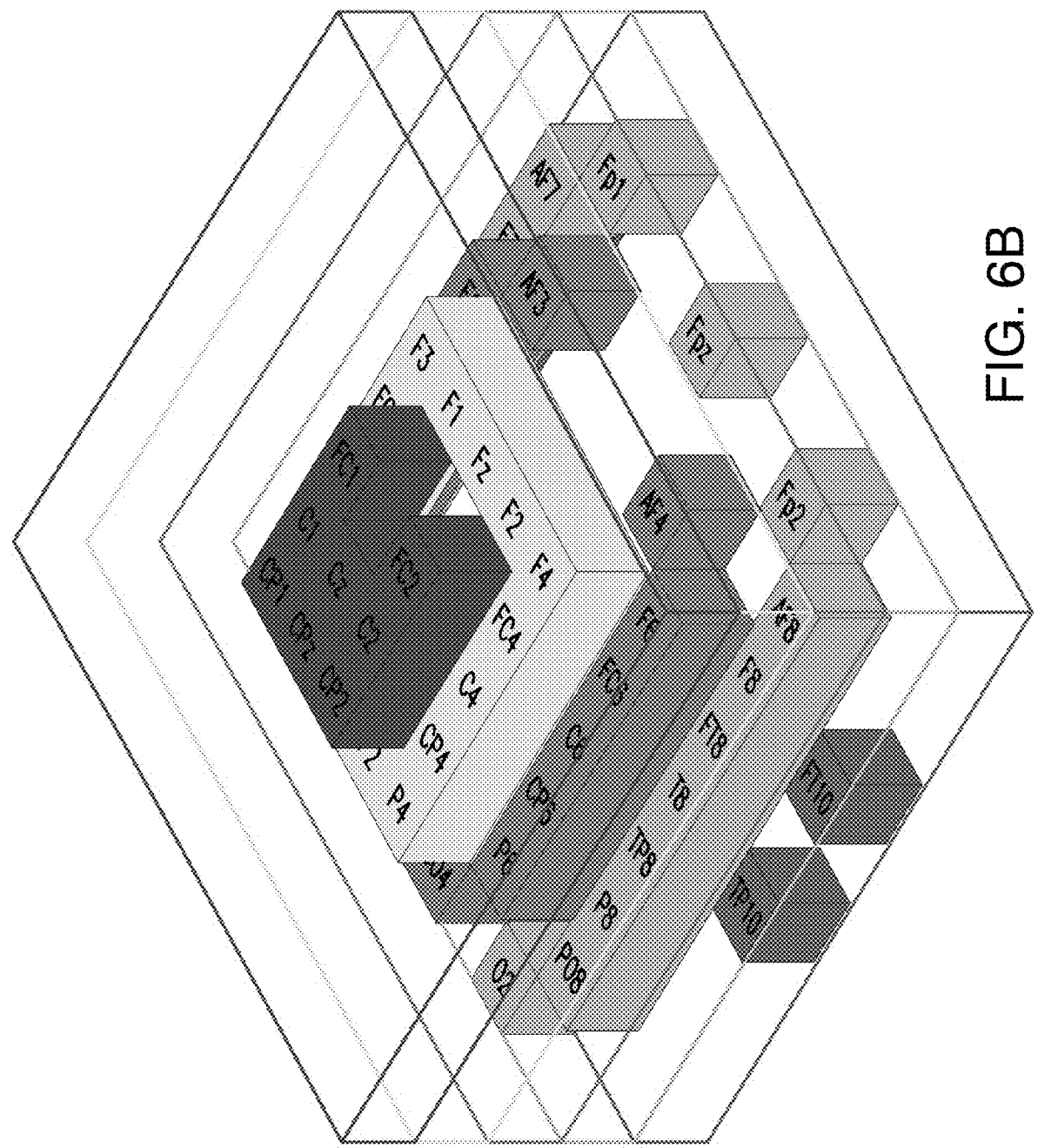

The layout of EEG cap and volume assignment: the layout of our MR compatible EEG cap is shown in FIG. 6A. The 63 electrodes were assigned on the surface of the scalp to a 3D volume of size 11×9×5. This assignment can compress the volume to the smallest meaningful size and ensures consistency in the localization of the electrodes. The outermost ring electrodes in FIG. 6A are in the lowest layer of the volume in FIG. 6B, and the electrodes in the center ring of FIG. 6A are in the top layer. Instead of using a fully connected layer, this technique can convert channel data to volume data through convolutional layers only and avoids potential overfitting problems. The disclosed volume assignment is not required to be very accurate but only needs to reflect the rough relative spatial relationship between electrodes. This is because the EEG decoder and EEG encoder of Cycle-CNN transcoder can learn any distortion of the leadfield regardless of the cause of such distortions (due to head anatomy or because of this coarse volume assignment).

Vanilla Transcoder: the vanilla transcoder model can include two transcoders: an fMRI-to-EEG transcoder and an EEG-to-fMRI transcoder, both are based on CNNs. fMRI-to-EEG Transcoder: the framework of the fMRI-to-EEG transcoder is shown in FIG. 2. The framework can include two main modules: a temporal deconvolution module and a spatial convolution module. 4D simulated fMRI data of size 16×16×35×60 (the last dimension is time) is bilinear interpolated to 16×16×35×300 and flattened to 2D (8960×300) before feeding to the temporal deconvolutional module made of 6 convolutional layers. In each layer, a convolution was applied to the data with 16 kernels of size 1×27 along the time dimension, resulting in feature maps generated by each layer of size 16@8960×300 (the digits before "@" stands for the number of channels and is equal to the number of kernels used for convolution). In the last convolutional layer of the temporal deconvolution module, the 16 channel data were collapsed to a single channel of source space data. This process is referred to as "shrink." The original 4 dimensions are recovered by reshaping the output of the temporal convolution module to 1@16×16×35×300 so that the 3D spatial convolution module can be applied to its first three dimensions. The spatial convolution module can include 12 layers in total, each layer applies 3D convolution of 16 kernels of size 3×3×3. The first layer of the spatial convolution module can downsample the z dimension to 7 to save memory. The last layer can join the 16 channels and generates a whole-brain EEG data prediction of size 1@16×16×7×300. A strided convolutional layer can be applied afterward to reduce the size of the data to 1@8×8×4×300 before it is flattened to 256×300. A fully connected layer can be used to map the dimension 256 to the simulated 68 channel EEG.

EEG-to-fMRI Transcoder: As shown in FIG. 3, the EEG-to-fMRI transcoder can be the reverse of the fMRI-to-EEG transcoder, with the exception that the temporal convolutional layers have feature maps of size 1792×300 instead of 8960×300.

Figures 4, 5A:
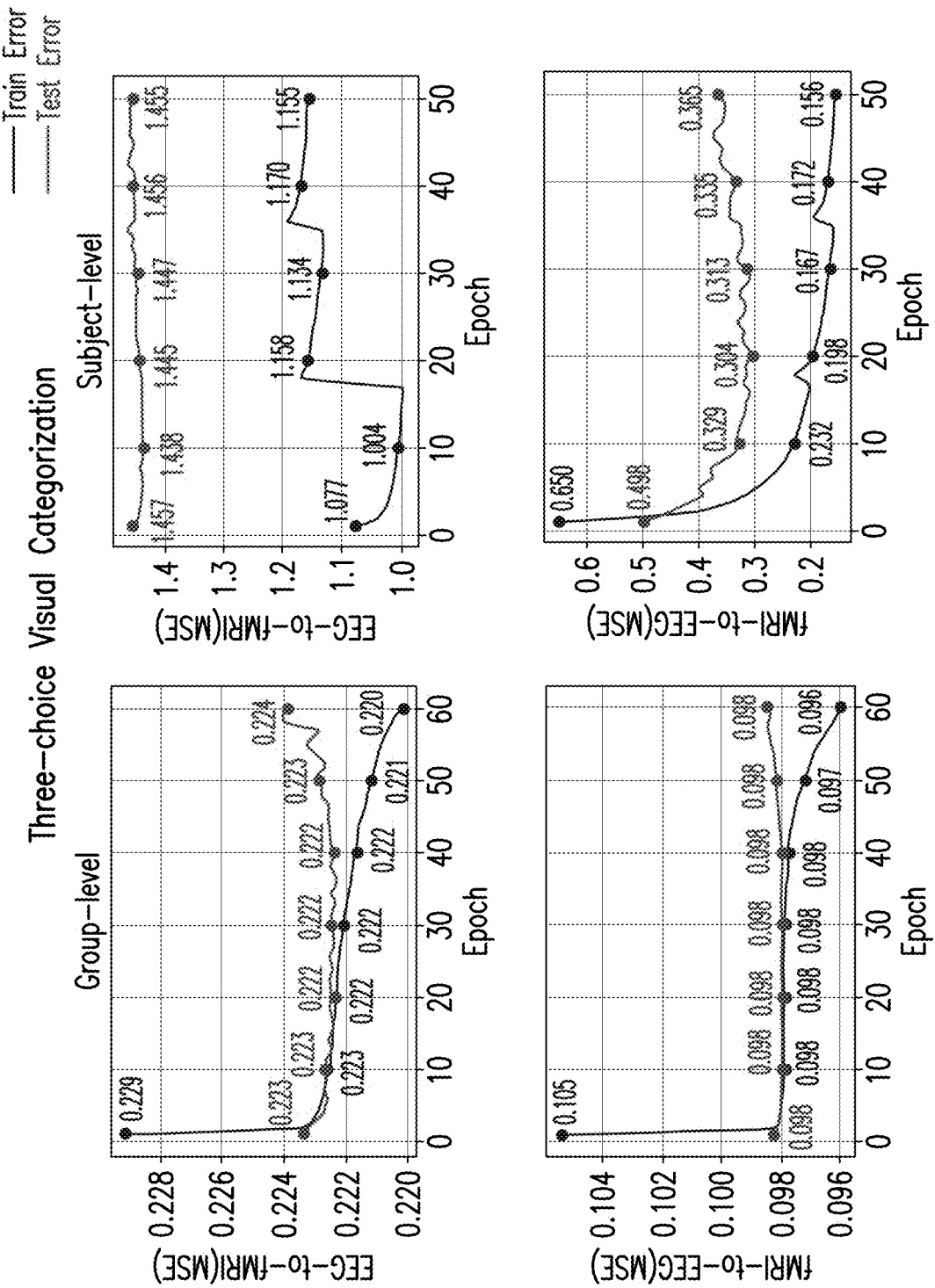

Bidirectional Coupled Transcoder: the complete model of bidirectional transcoding is shown in FIG. 4. This model can include the two transcoders and is coupled with shared weights of modules adjacent to the source space.

Evaluation: To test bidirectional transcoding performance, the fMRI-based source prediction $S^{fMRI}$ and EEG prediction E are acquired by feeding the fMRI-to-EEG transcoder with noise-free data of accordant slice timing settings. The EEG-based source prediction $S^{EEG}$ and fMRI prediction F are acquired by feeding the EEG-to-fMRI transcoder with noise-free data of accordant slice timing settings.

Figures 5, 5A:
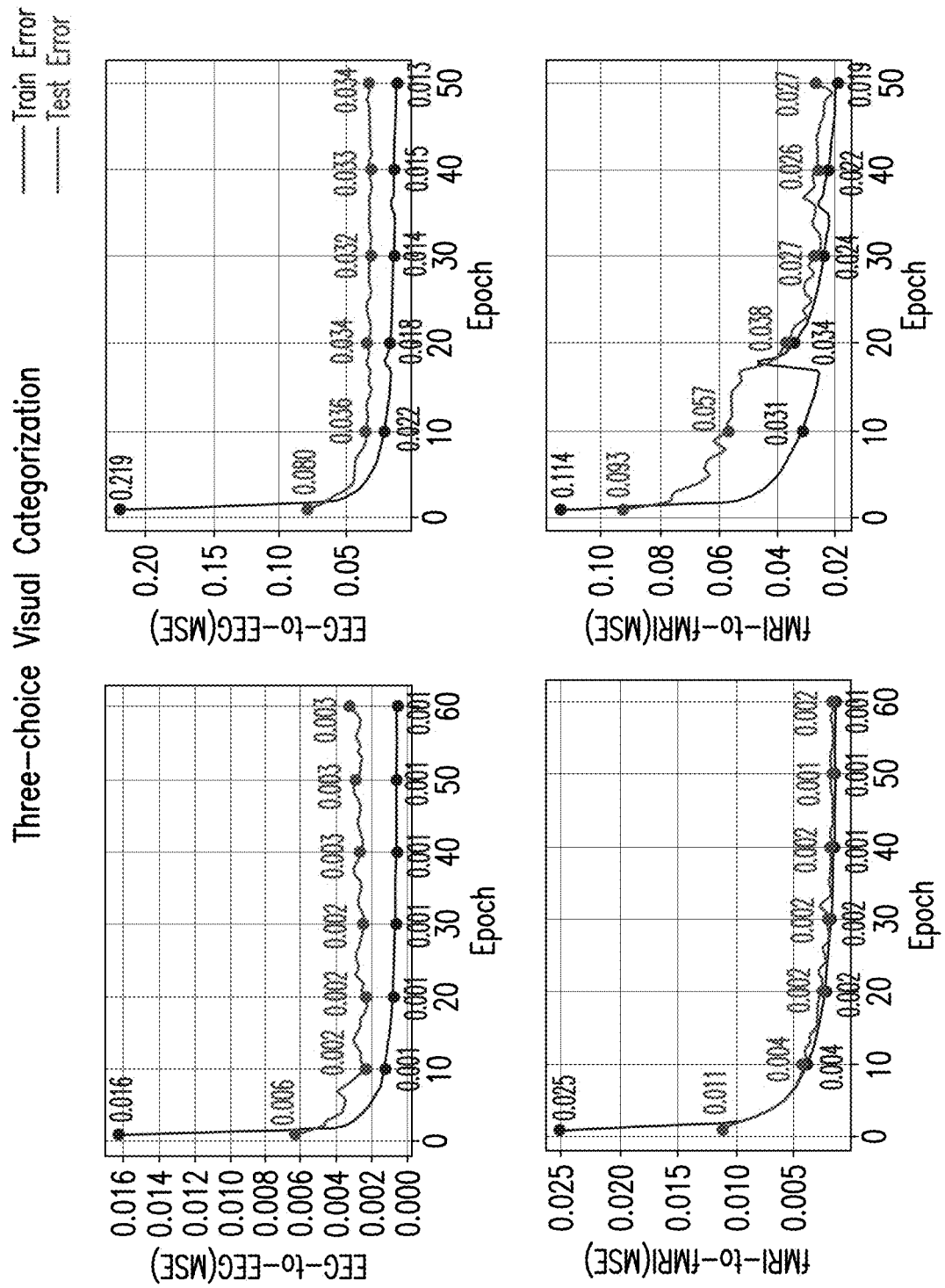
Figures 5, 5A, 6:
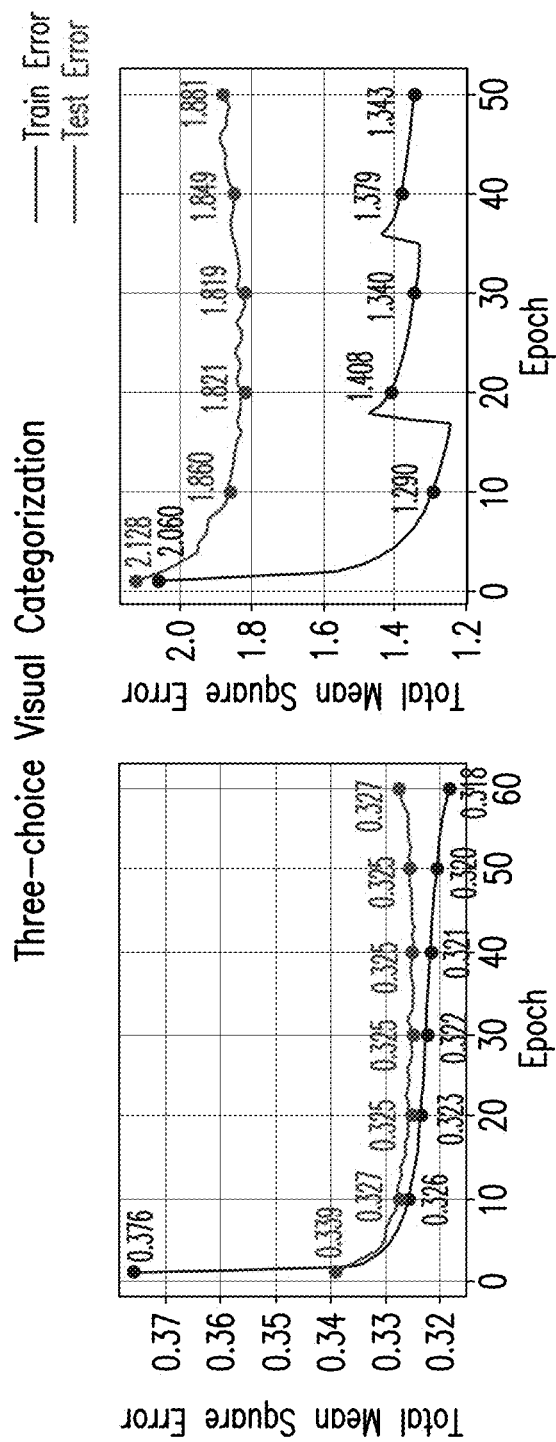

FIG. 5 shows the mean of the 19,600s runs test data's correlation coefficient between the prediction and the ground-truth. These are shown as a function of the three settings. FIG. 5I shows the correlation coefficients between $F^{\wedge}$ and fMRI ground-truth, F. FIG. 5I shows high correlations in all settings, indicating the fMRI predictions are accurate and seemingly robust to the simulated acquisition parameters and noise that we investigated. This is evident in FIG. 5A, showing $F^{\wedge}$ and fMRI ground-truth F for location 1, which is an oscillatory source and FIG. 5B for location 2 having a sparse source. The correlations coefficients between $E^{\wedge}$ and E, shown in FIG. 5I(V) are relatively low, though still highly significant. Examples of $^{\wedge}E$, relative to ground truth E, for two electrodes, located at 3 and 4, are shown in FIG. 5E and FIG. 5F.

For both fMRI-to-EEG and EEG-to-fMRI transcoding, when the training data is noise-free, the model is trained with no slice timing (left), and the model is trained by interleaved5 data (middle) yield significantly different correlations, with the interleaved5 data producing higher correlation with the ground-truth. This is because interleaved acquired data have different slices acquired at different times, allowing the model to access more variability of the training data. The effect can be similar to a widely used technique in the deep learning field called data augmentation. A substantial reduction in correlation between the estimate and ground-truth is seen between EEG-to-fMRI models trained with data having SNR=10 (right) and noise-free data (left and middle).

Transcoding from one modality to the other demonstrates the disclosed model's ability to capture the relationship between two modalities, mapping one to the other. Next, we show the model performance for resolving the source space from the two modalities using knowledge of the inter-modality relationship.

FIG. 5B (ii) and FIG. 5B (III) show the mean correlation coefficient of 304, 30s data epochs taken from the 19,600s runs, where these epochs were not part of the model training data. The correlation coefficient is calculated between the source space predictions and the ground truth source space simulation. The same three settings are discussed here. FIG. 5B (II) shows the correlation coefficients between the estimated EEG sources $S^{\wedge EEG}$ and the ground-truth S. FIG. 5B (iii) shows the correlation coefficients between the estimated fMRI sources $S^{\wedge fMRI}$ and ground-truth S. The mean correlation coefficients are shown separately for sources of oscillatory activity (marked as "osc") and impulse/evoked activity (marked as "sparse"). The mean correlation coefficients for all activity are marked as "all(osc+sparse)."

Interestingly, the effect of interleave5 slice timing on source recovery has an opposite effect when transcoding fMRI-to-EEG relative to EEG-to-fMRI. For fMRI-to-EEG transcoding (FIG. 5B (iii)), adding interleave5 slice timing significantly reduces the accuracy of source recovery. This is because inferring the source from the fMRI requires upsampling and deconvolution in the temporal dimension, both of which are sensitive to timing. The interleaved acquisition naturally adds uncertainty in the temporal dimension. The performance drop, in terms of source recovery accuracy, is more significant for oscillatory activity. For EEG-to-fMRI transcoding, shown in FIG. 5B(ii), adding interleave5 slice timing actually significantly improves source recovery. This can be because inferring sources from EEG requires only a spatial mapping where timing is not critical.

Another noteworthy finding is that the trends of the correlation of reconstruction for the signal space (EEG or fMRI) and source space do not necessarily agree. Take FIG. 5B(I) and FIG. 5B(II) as an example, where after adding noise, the correlation coefficient of fMRI reconstruction decreases (compare FIG. 5B(I) Interleave5 NoiseFree and Interleave5 SNR10), but the source space prediction correlation increases (compare FIG. 5B(II) Interleave5 NoiseFree and Interleave5 SNR10). This is because the source space reconstruction is only affected by the spatial deconvolutional module, while fMRI reconstruction is affected by both the spatial deconvolutional and temporal convolutional modules. The spatial deconvolutional layer is more prone to overfitting due to the fully connected layer, which makes the correlation coefficients respond differently to variations of noise levels in data.

Results of all inferred EEG channels of the subject can be found in FIGS. 14-28.

Figure 14:
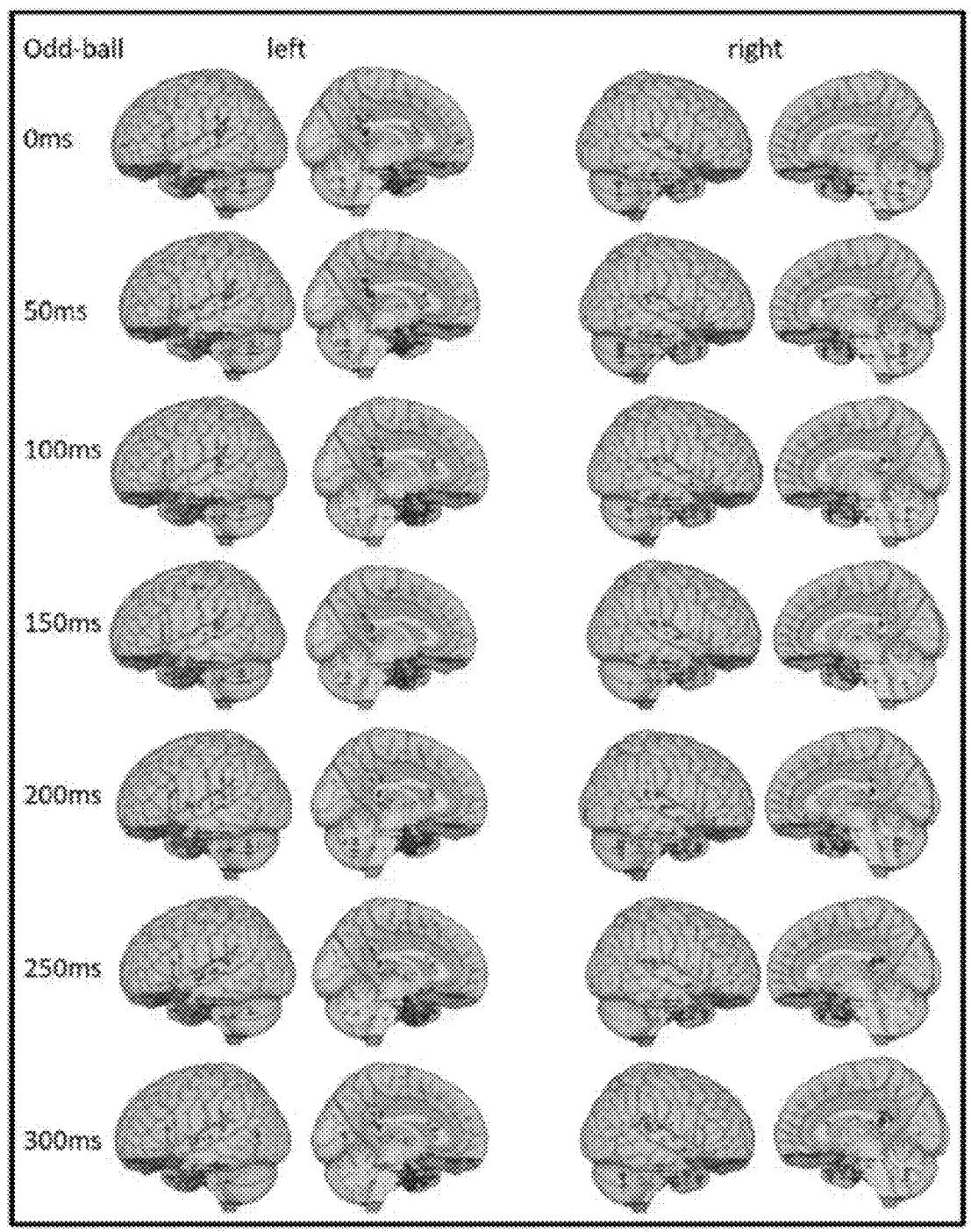
FIG. 14 provides images showing complete thresholded Z-statistics of super-resolution latent source space reconstruction of brain dynamic during 0 to 300 ms after Odd-ball tone auditory stimuli onset in accordance with the disclosed subject matter.

FIG. 14 shows complete thresholded Z-statistics of super-resolution latent source space reconstruction of brain dynamic during 0 to 300 ms after Odd-ball tone auditory stimuli onset in accordance with the disclosed subject matter.

Figure 15:
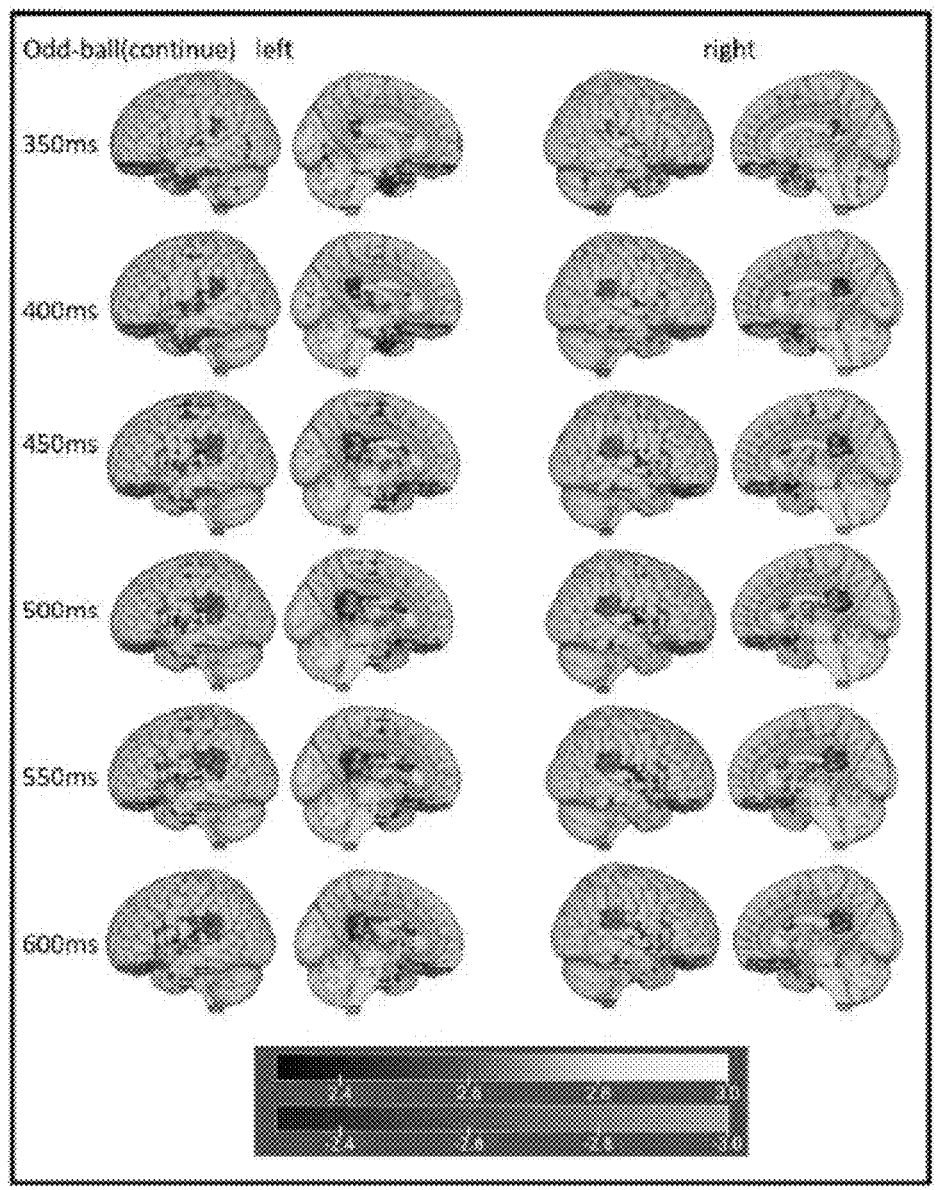
FIG. 15 provides images showing complete thresholded Z-statistics of super-resolution latent source space reconstruction of brain dynamic during 350 to 600 ms after Odd-ball tone auditory stimuli onset in accordance with the disclosed subject matter.

FIG. 15 shows complete thresholded Z-statistics of super-resolution latent source space reconstruction of brain dynamic during 350 to 600 ms after Odd-ball tone auditory stimuli onset in accordance with the disclosed subject matter.

Figure 16:
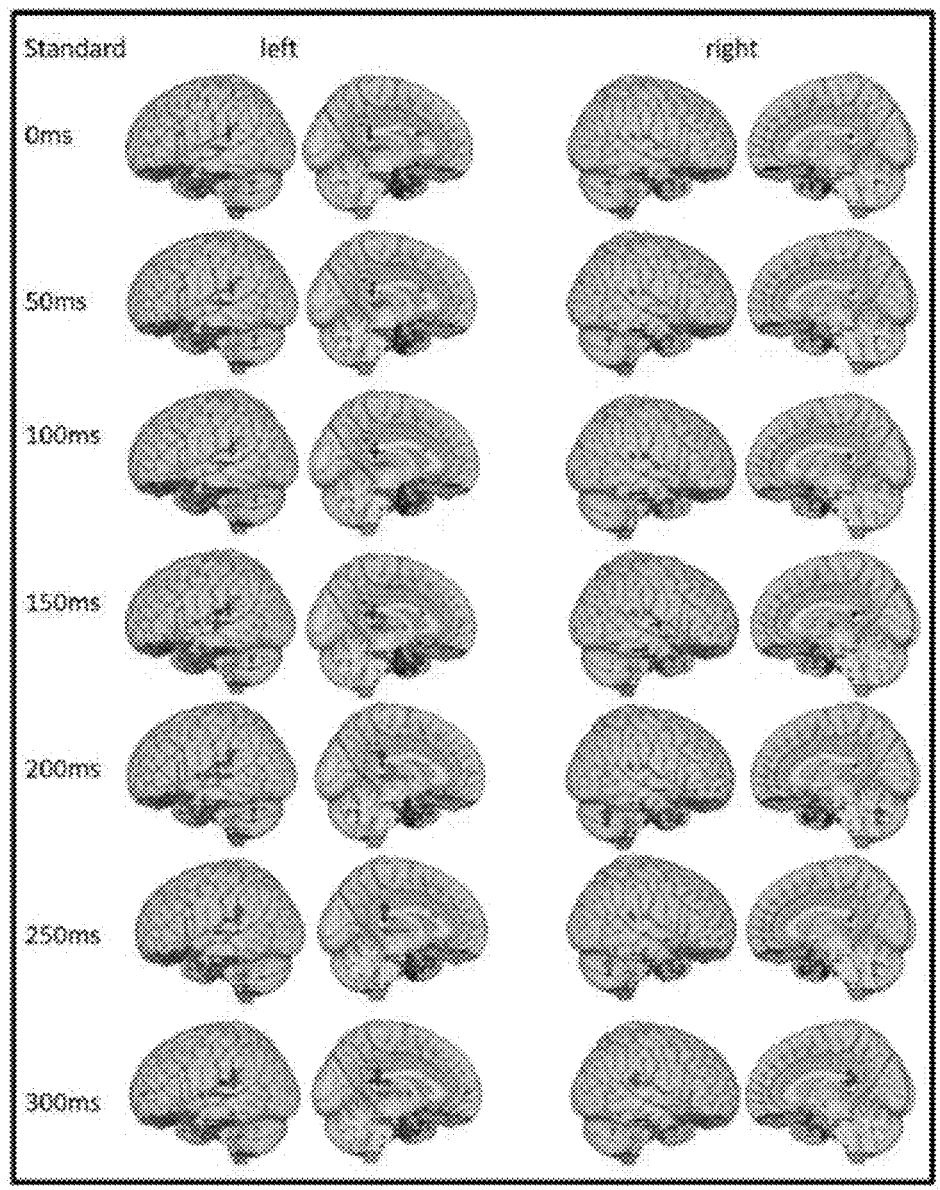
FIG. 16 provides images showing complete thresholded Z-statistics of super-resolution latent source space reconstruction of brain dynamic during 0 to 300 ms after standard tone auditory stimuli onset in accordance with the disclosed subject matter.

FIG. 16 shows complete thresholded Z-statistics of super-resolution latent source space reconstruction of brain dynamic during 0 to 300 ms after standard tone auditory stimuli onset in accordance with the disclosed subject matter.

Figure 17:
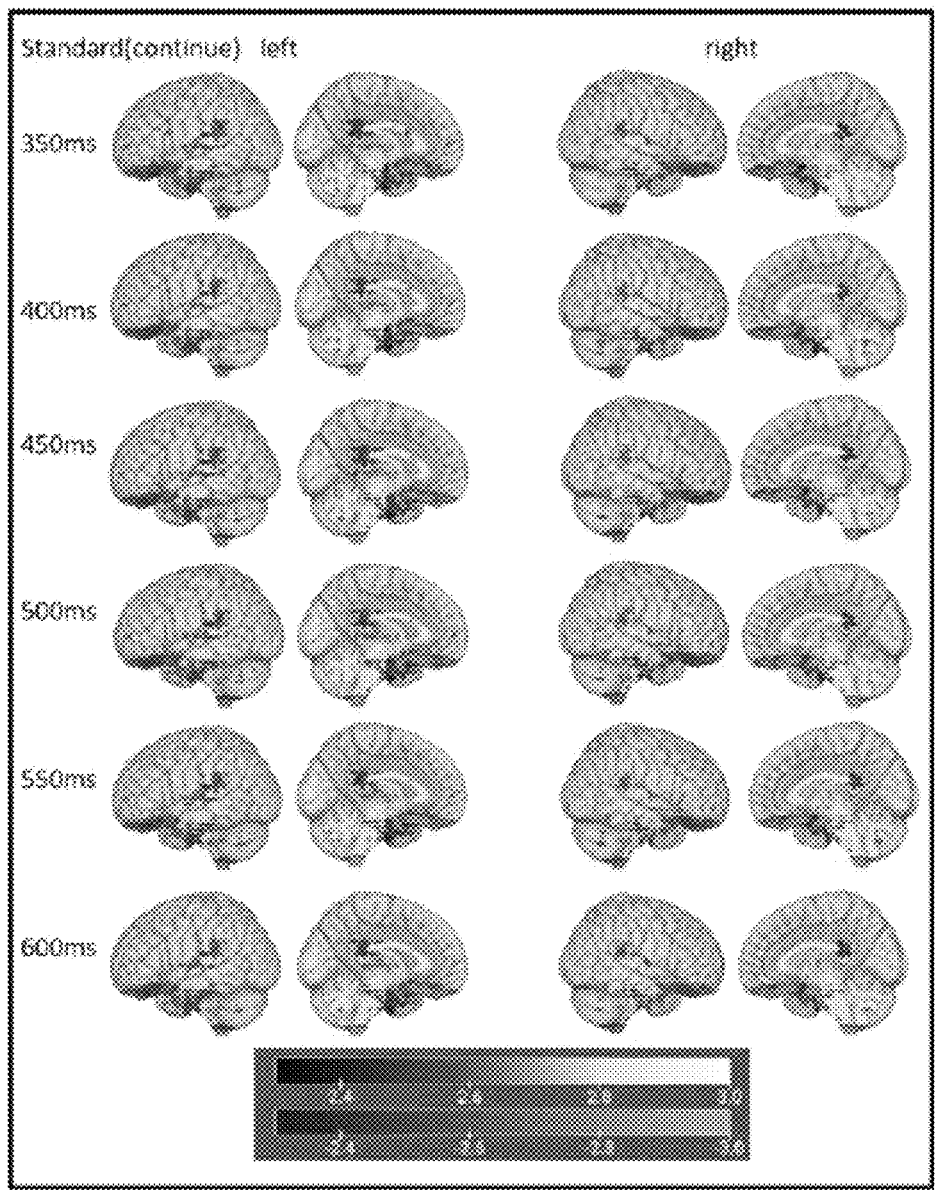
FIG. 17 provides images showing complete thresholded Z-statistics of super-resolution latent source space reconstruction of brain dynamic during 350 to 600 ms after standard tone auditory stimuli onset in accordance with the disclosed subject matter.

FIG. 17 shows complete thresholded Z-statistics of super-resolution latent source space reconstruction of brain dynamic during 350 to 600 ms after standard tone auditory stimuli onset in accordance with the disclosed subject matter.

Figure 18:
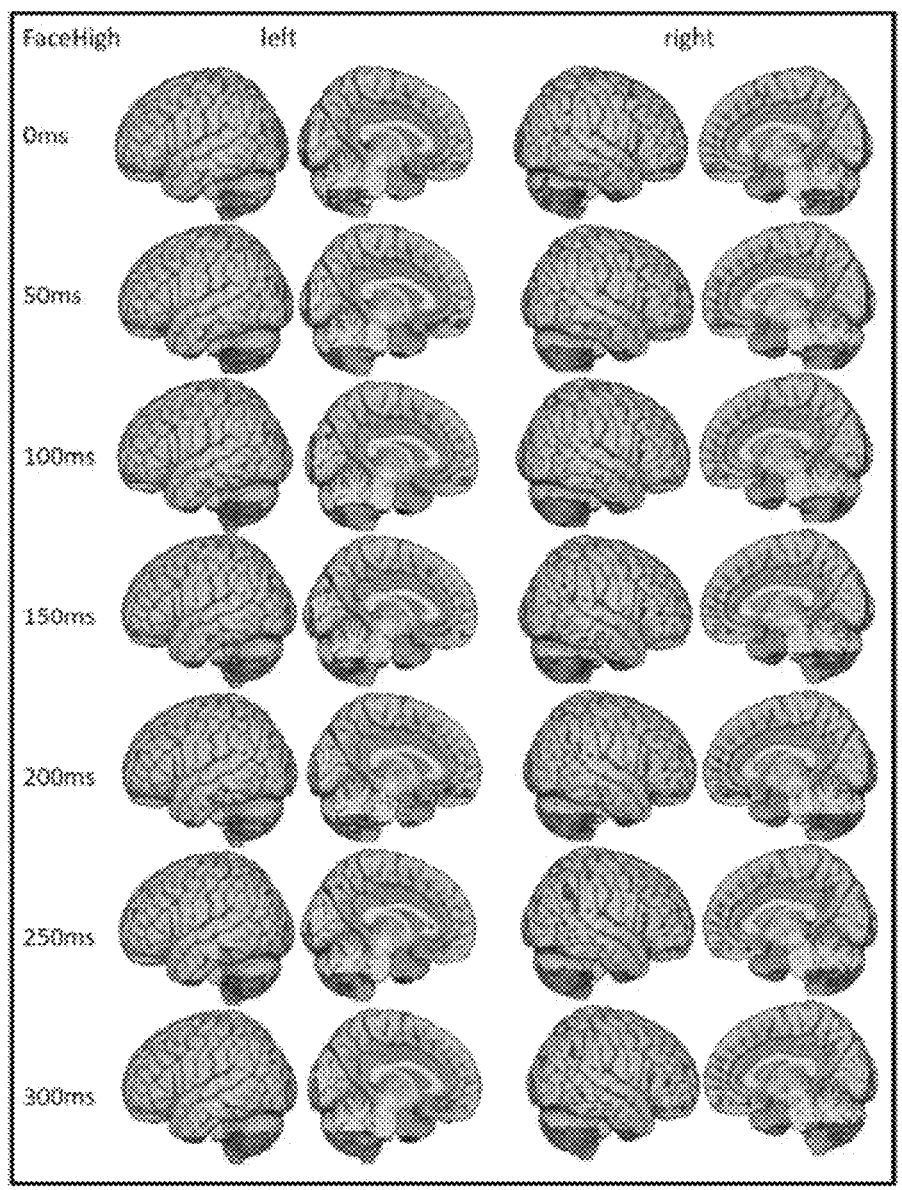
FIG. 18 provides images showing complete thresholded Z-statistics of super-resolution latent source space reconstruction of brain dynamic during 0 to 300 ms after high contrast face visual stimuli onset in accordance with the disclosed subject matter.

FIG. 18 shows complete thresholded Z-statistics of super-resolution latent source space reconstruction of brain dynamic during 0 to 300 ms after high contrast faces visual stimuli onset in accordance with the disclosed subject matter.

Figure 19:
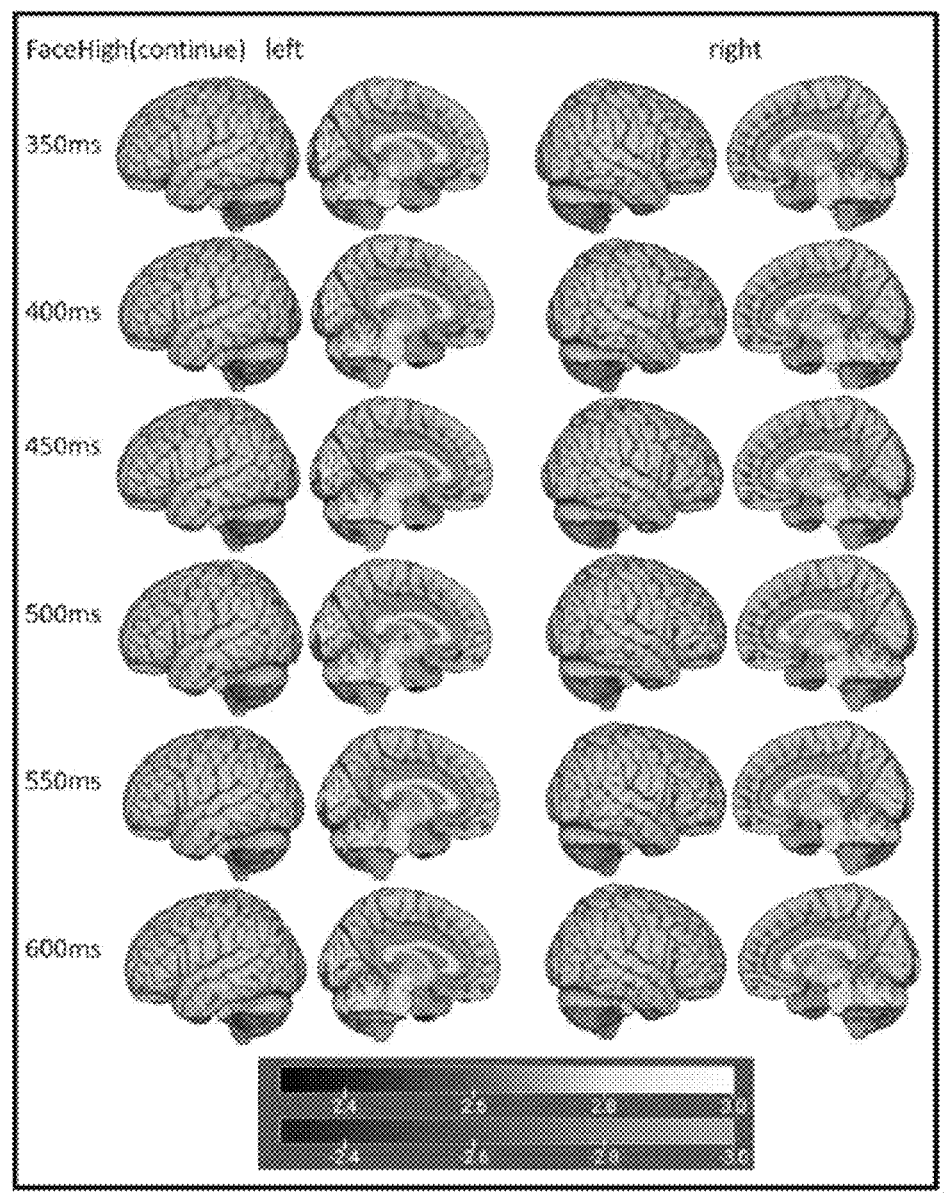
FIG. 19 provides images showing complete thresholded Z-statistics of super-resolution latent source space reconstruction of brain dynamic during 350 to 600 mss after high contrast face visual stimuli onset in accordance with the disclosed subject matter.

FIG. 19 shows complete thresholded Z-statistics of super-resolution latent source space reconstruction of brain dynamic during 350 to 600 mss after high contrast faces visual stimuli onset in accordance with the disclosed subject matter.

Figure 20:
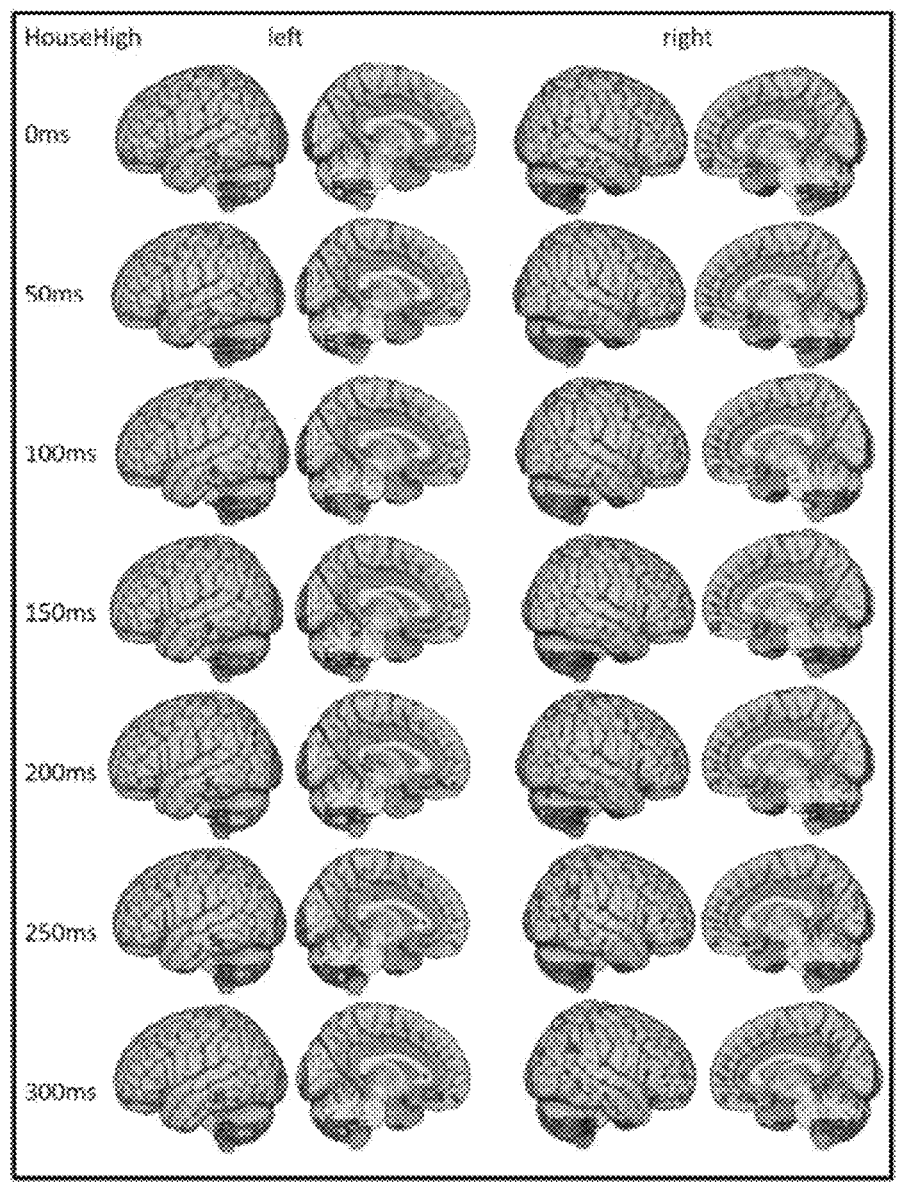
FIG. 20 provides images showing complete thresholded Z-statistics of super-resolution latent source space reconstruction of brain dynamic during 0 to 300 ms after high contrast face visual stimuli onset in accordance with the disclosed subject matter.

FIG. 20 shows complete thresholded Z-statistics of super-resolution latent source space reconstruction of brain dynamic during 0 to 300 ms after high contrast faces visual stimuli onset in accordance with the disclosed subject matter.

Figure 21:
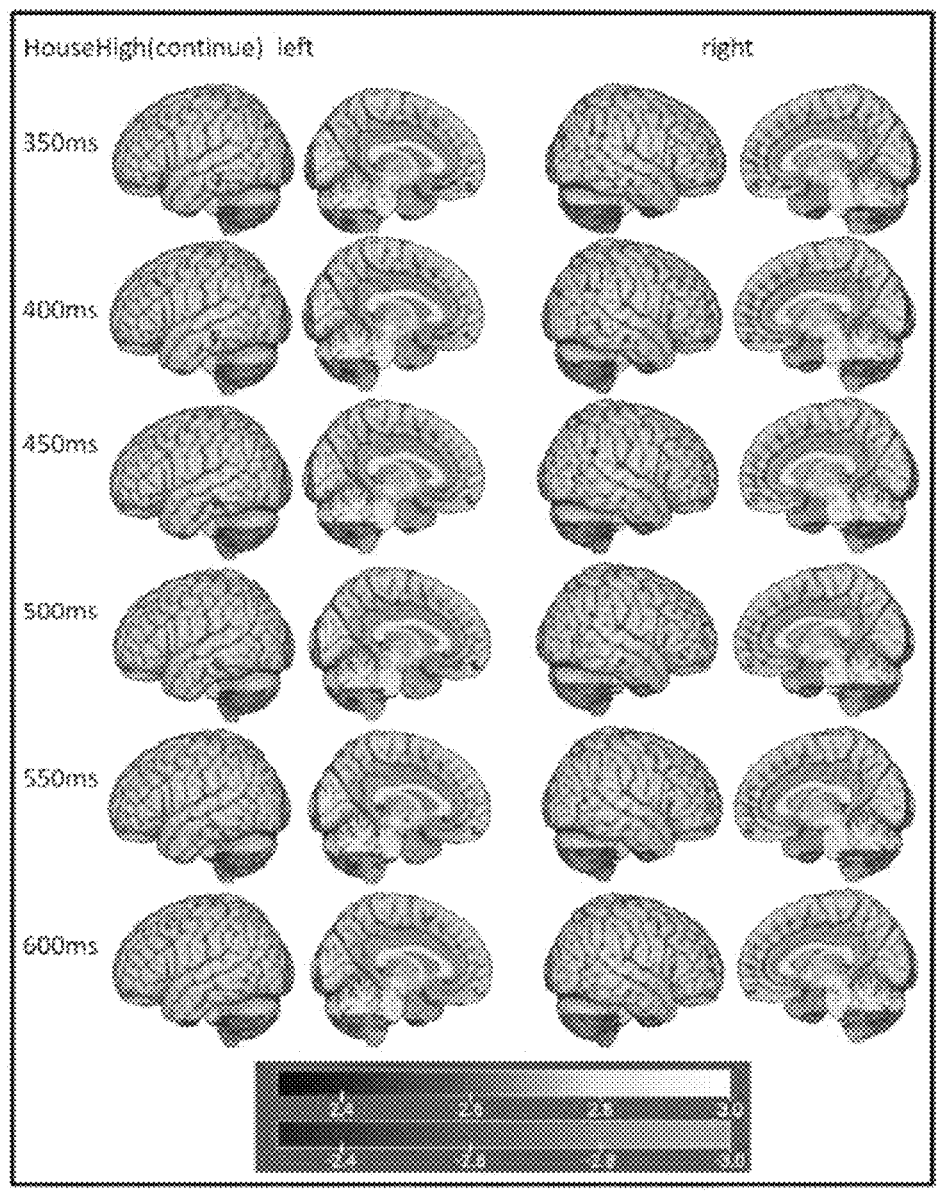
FIG. 21 provides images showing complete thresholded Z-statistics of super-resolution latent source space reconstruction of brain dynamic during 350 to 600 mss after high contrast face visual stimuli onset in accordance with the disclosed subject matter.

FIG. 21 shows complete thresholded Z-statistics of super-resolution latent source space reconstruction of brain dynamic during 350 to 600 mss after high contrast faces visual stimuli onset in accordance with the disclosed subject matter.

Figure 22:
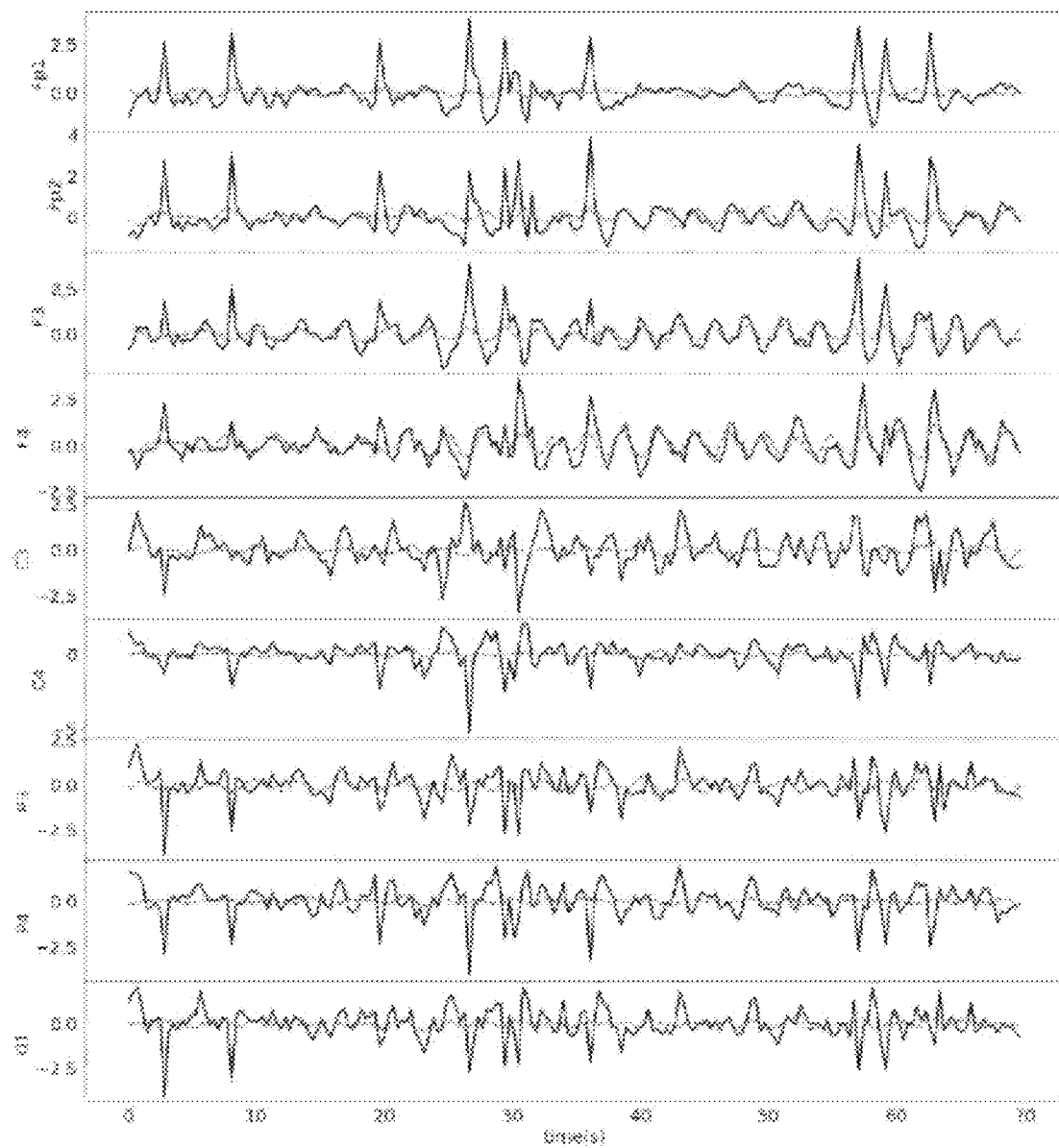
FIG. 22 provides graphs showing auditory oddball task fMRI-to-EEG transcoding: EEG transcoded from fMRI V.S. EEG ground truth (part 1) in accordance with the disclosed subject matter.

FIG. 22 shows auditory oddball task fMRI-to-EEG transcoding: EEG transcoded from fMRI V.S. EEG ground truth (part 1) in accordance with the disclosed subject matter.

Figure 23:
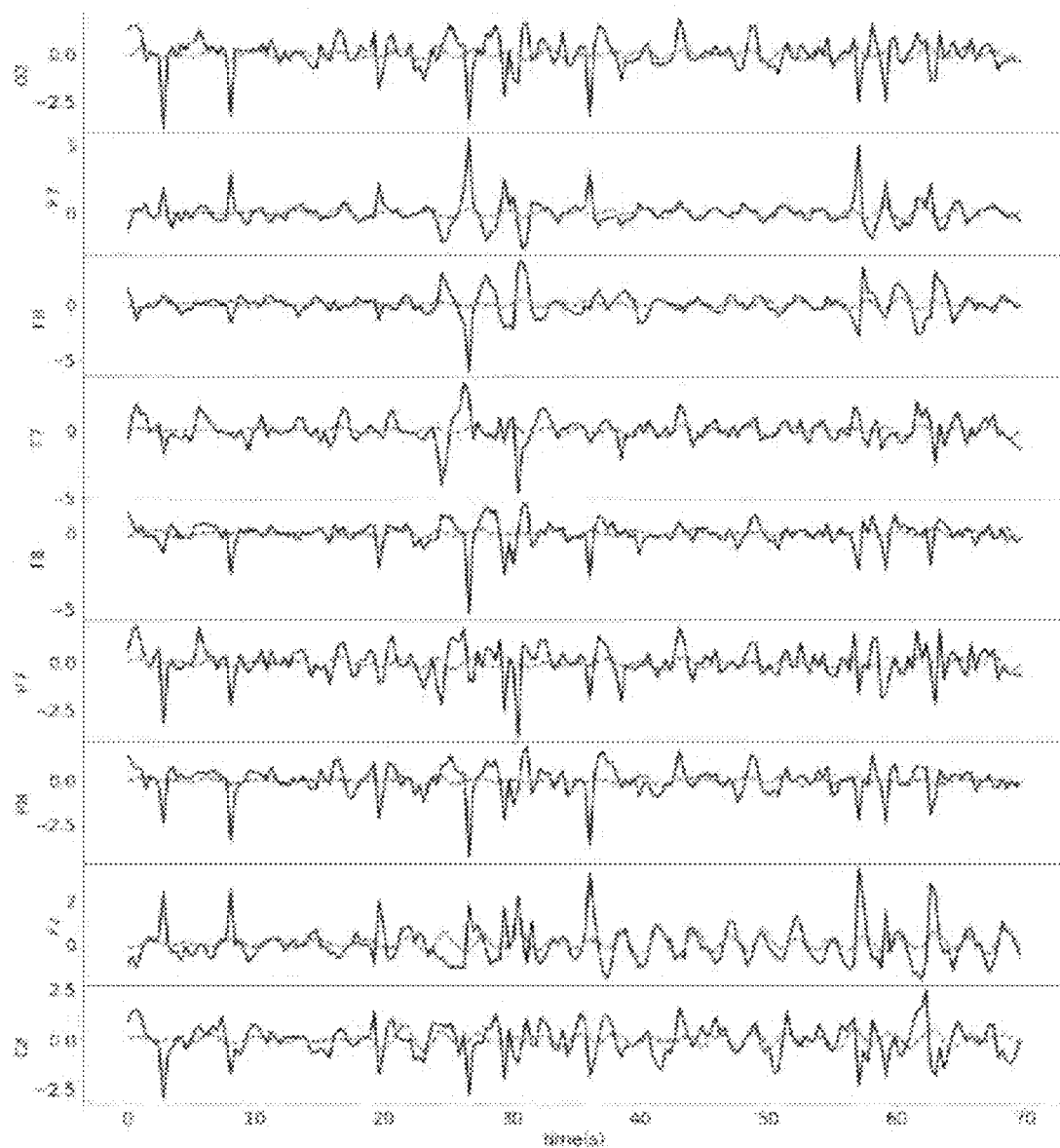
FIG. 23 provides graphs showing auditory oddball task fMRI-to-EEG transcoding: EEG transcoded from fMRI V.S. EEG ground truth (part 2) in accordance with the disclosed subject matter.

FIG. 23 shows auditory oddball task fMRI-to-EEG transcoding: EEG transcoded from fMRI V.S. EEG ground truth (part 2) in accordance with the disclosed subject matter.

Figure 24:
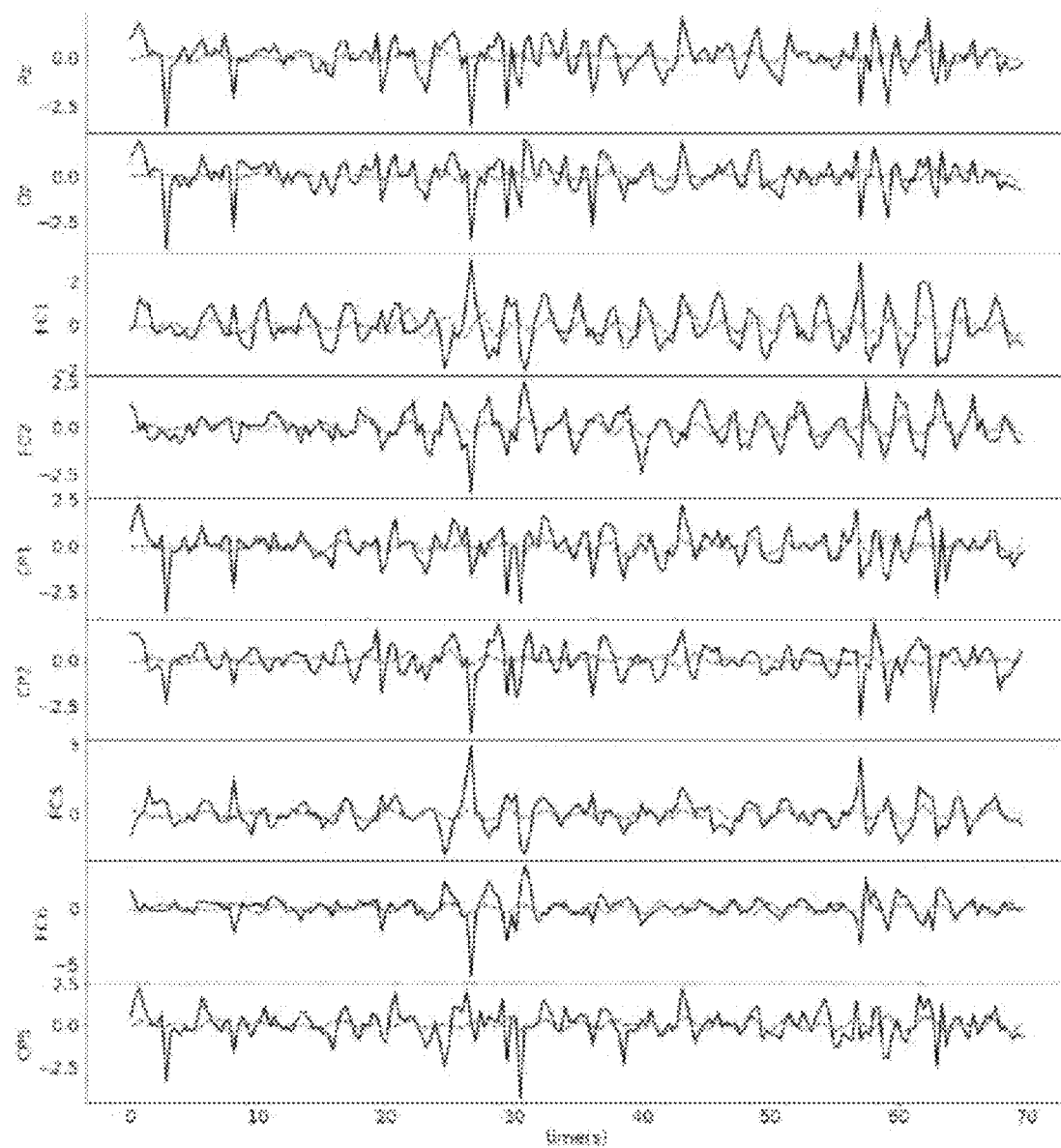
FIG. 24 provides graphs showing auditory oddball task fMRI-to-EEG transcoding: EEG transcoded from fMRI V.S. EEG ground truth (part 3) in accordance with the disclosed subject matter.

FIG. 24 shows auditory oddball task fMRI-to-EEG transcoding: EEG transcoded from fMRI V.S. EEG ground truth (part 3) in accordance with the disclosed subject matter.

Figure 25:
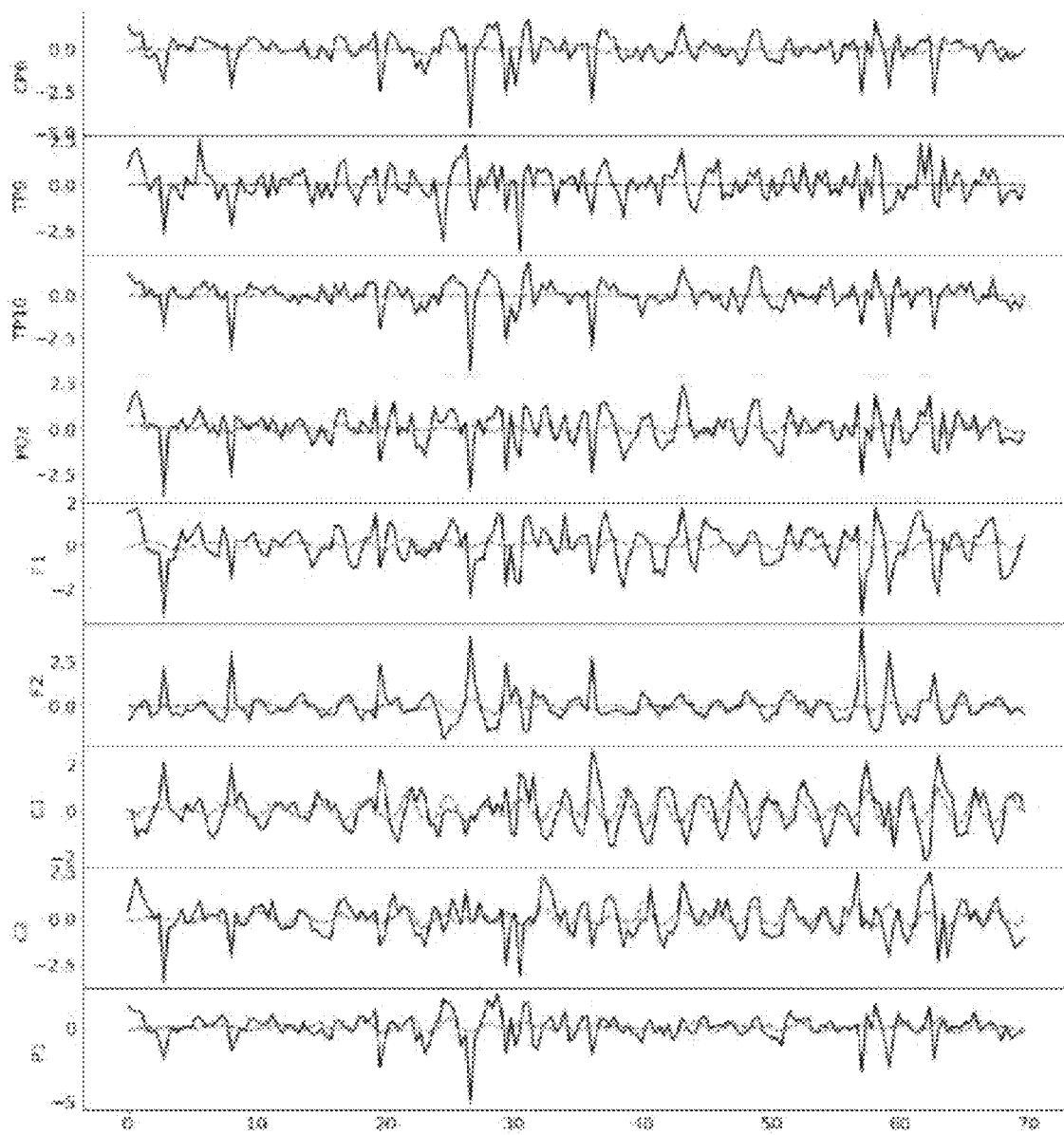
FIG. 25 provides graphs showing auditory oddball task fMRI-to-EEG transcoding: EEG transcoded from fMRI V.S. EEG ground truth (part 4) in accordance with the disclosed subject matter.

FIG. 25 shows auditory oddball task fMRI-to-EEG transcoding: EEG transcoded from fMRI V.S. EEG ground truth (part 4) in accordance with the disclosed subject matter.

Figure 26:
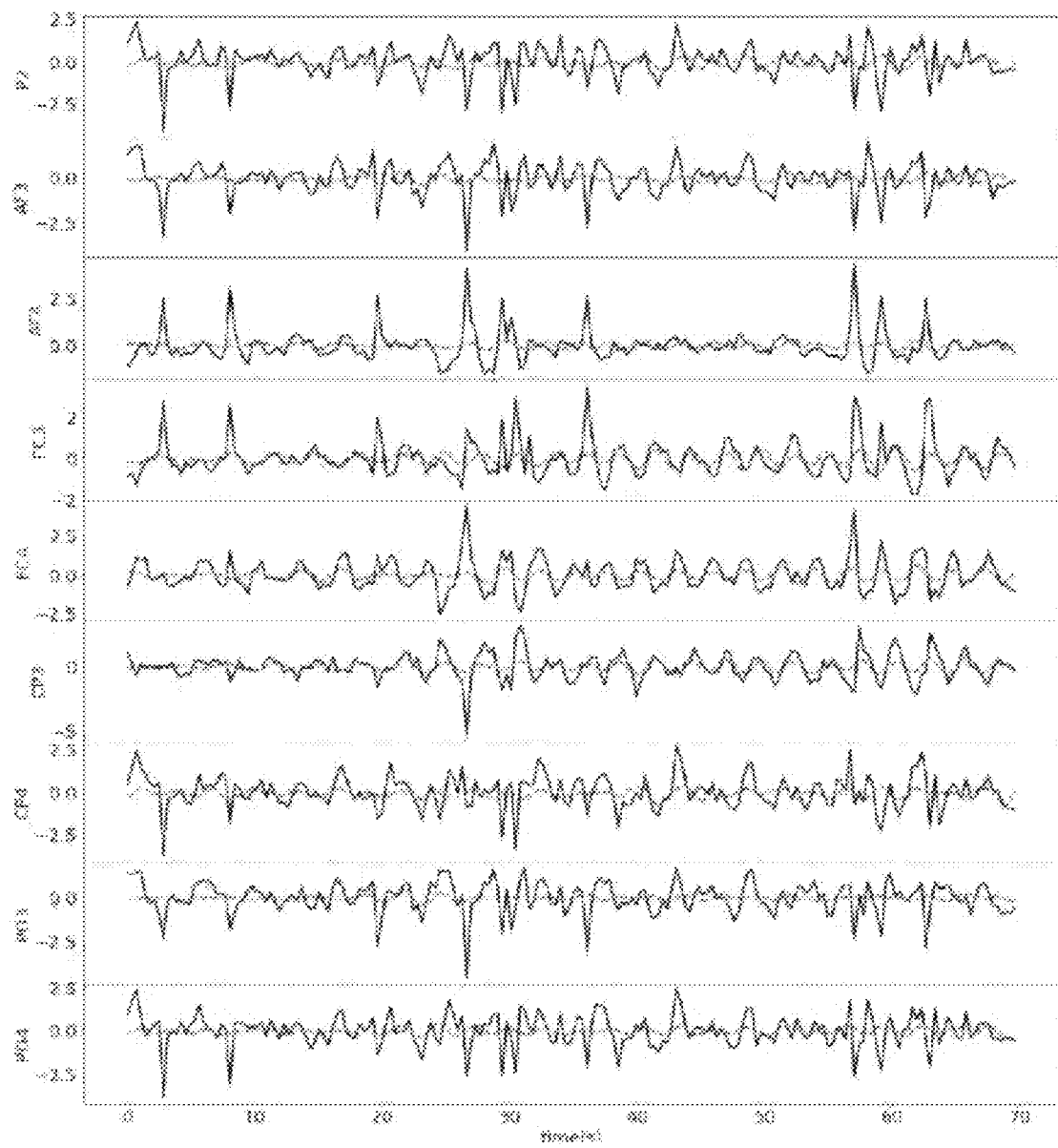
FIG. 26 provides graphs showing auditory oddball task fMRI-to-EEG transcoding: EEG transcoded from fMRI V.S. EEG ground truth (part 5) in accordance with the disclosed subject matter.

FIG. 26 shows auditory oddball task fMRI-to-EEG transcoding: EEG transcoded from fMRI V.S. EEG ground truth (part 5) in accordance with the disclosed subject matter.

Figure 27:
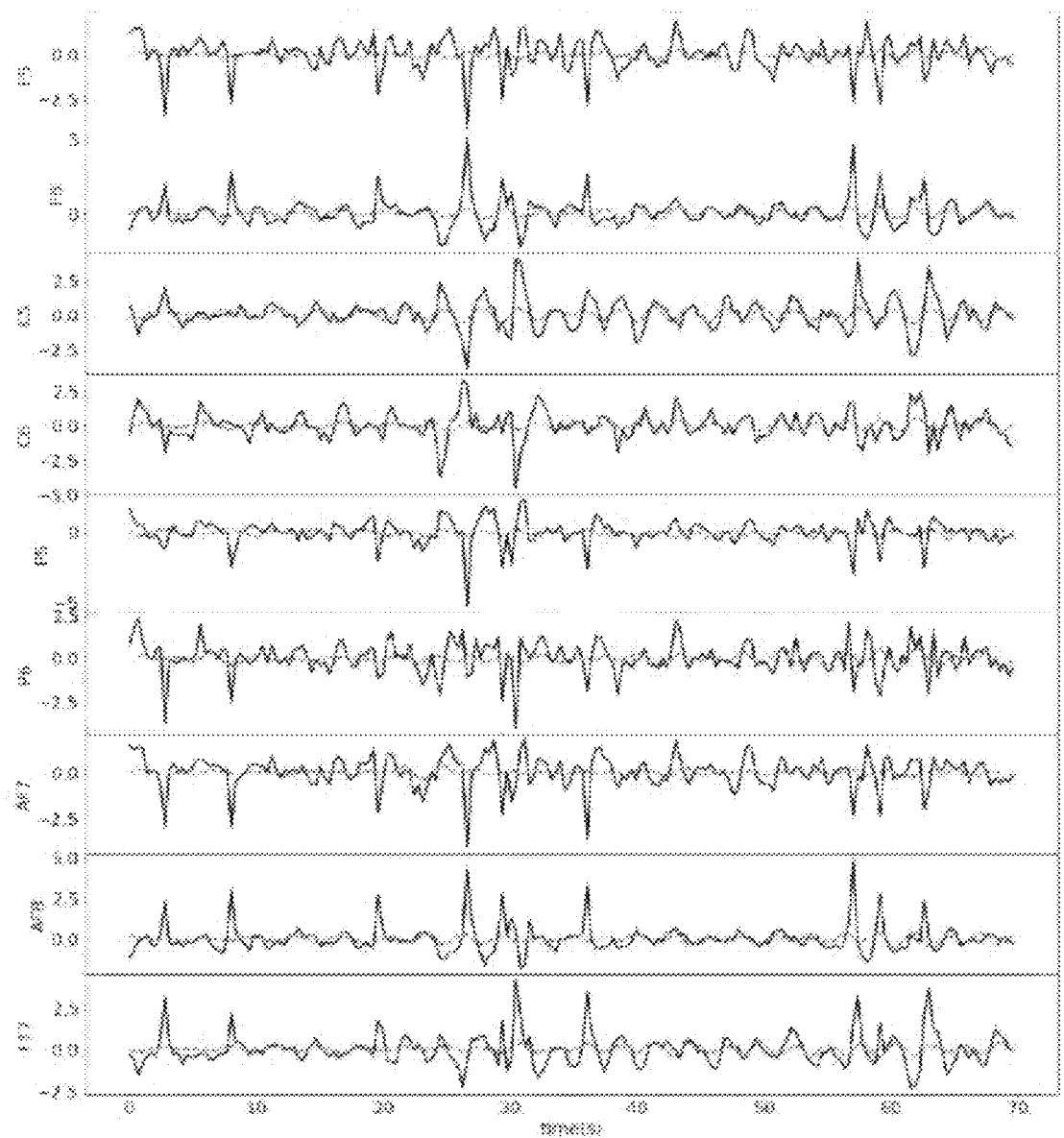
FIG. 27 provides graphs showing auditory oddball task fMRI-to-EEG transcoding: EEG transcoded from fMRI V.S. EEG ground truth (part 6) in accordance with the disclosed subject matter.

FIG. 27 shows auditory oddball task fMRI-to-EEG transcoding: EEG transcoded from fMRI V.S. EEG ground truth (part 6) in accordance with the disclosed subject matter.

Figure 28:
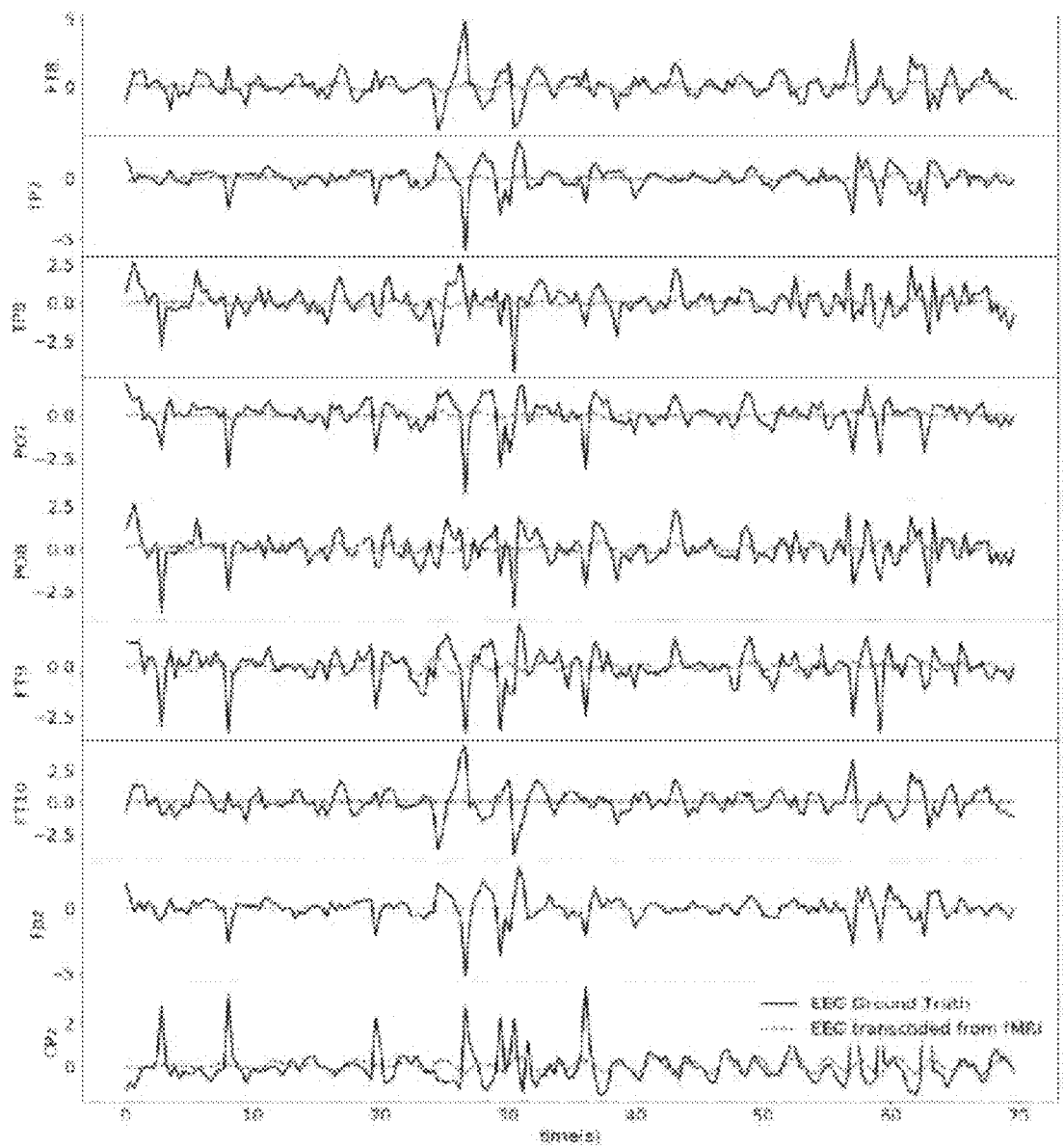
FIG. 28 provides graphs showing auditory oddball task fMRI-to-EEG transcoding: EEG transcoded from fMRI V.S. EEG ground truth (part 7) in accordance with the disclosed subject matter.

FIG. 28 shows auditory oddball task fMRI-to-EEG transcoding: EEG transcoded from fMRI V.S. EEG ground truth (part 7) in accordance with the disclosed subject matter.

Example 2: Unsupervised Backprojection Via Convolutional and Spatial Transformer Networks and its Application on Sparse-View CT After transcoding EEG and fMRI to source space respectively with CNN, the transcoded signals can be electrical signals. fMRI can be upsampled in the time dimension and EEG can be mapped from a dozen channels to a small 3D volume. However, fMRI can be upsampled 5 to 6 times, as its original TR=2s, the sampling rate after transcoding can still be only around 2.5 Hz or 3 Hzm, which are different from the temporal resolution 500 Hz to 1000 Hz of EEG. Meanwhile, after transcoding, comparing to the typical volume size 64×64×35 of fMRI whose spatial resolution is 2 mm×2 mm×3 mm, the volume size of transcoded EEG is 16×16×7 corresponds to a spatial resolution of only 8 mm×8 mm×10 mm. This is still quite far from the desired goal of decoding the source space of EEG's temporal resolution and fMRI's spatial resolution.

The source space can be 4D with three spatial dimensions x, y, z and one temporal dimension t. The spatial dimensions x, y, z can have the volume size of 64×64×35 with a spatial resolution of 2 mm×2 mm×3 mm as fMRI. The temporal dimension t can have the same temporal resolution of 500 Hz to 1000 Hz as EEG. Since the transcoding can apply a temporal transformation to fMRI data but reserves its spatial information, only spatial transformation is applied to EEG and its temporal information reserved. The EEG predicted source space can have the desired temporal resolution while the spatial resolution can be lower than what is desired, the fMRI predicted source space is with the desired spatial resolution, and/or its temporal resolution is still not high enough. As both of them can origin from the same source space, EEG predicted source space can be considered as a projection of the source space in the x, y, z direction, while the fMRI predicted source space can be considered as a projection of the source space in t direction. This yields the reconstruction of the source space from EEG predicted source space and fMRI predicted source space to be a back-projection problem with 2 projections available.

The backprojection problem refers to a multidimensional inverse problem given a finite number of projections, certain imaging technologies such as computed tomography (CT) rely on solving backprojection problems to reconstruct the image. The reconstruction methods can be backprojection and the Fourier-domain reconstruction algorithm. These two methods are tightly related and it has been shown for example, that applying a filter in the Fourier-domain can yield similar results to filtered backprojection. Thus, these two classes of reconstruction methods can be referred as "backprojection algorithms." Backprojection algorithms can normally be trust worth when there is a lot of angles of projections. However, they can result in poor image reconstructions when the projection angles are sparse and/or if the sensors characteristics are not uniform. The issue can fall in the hard category for classic backprojection algorithms, as 2 projections are available. Furthermore, because of the very different nature of the two modalities, the "sensors" for the 2 projections can be different. Several deep learning based algorithms have been developed to backprojection the problem and reconstruct the image using a limited number of projections. However, these algorithms require examples of the ground-truth (i.e., examples of reconstructed images) to yield good performance. Because the ground truth of the source space is not accessible in the disclosed system, normal deep learning based algorithms are not suitable. Because of these reasons, the disclosed subject matter provides a new method that can handle unsupervised sparse-view backprojection problem.

Figure 29:
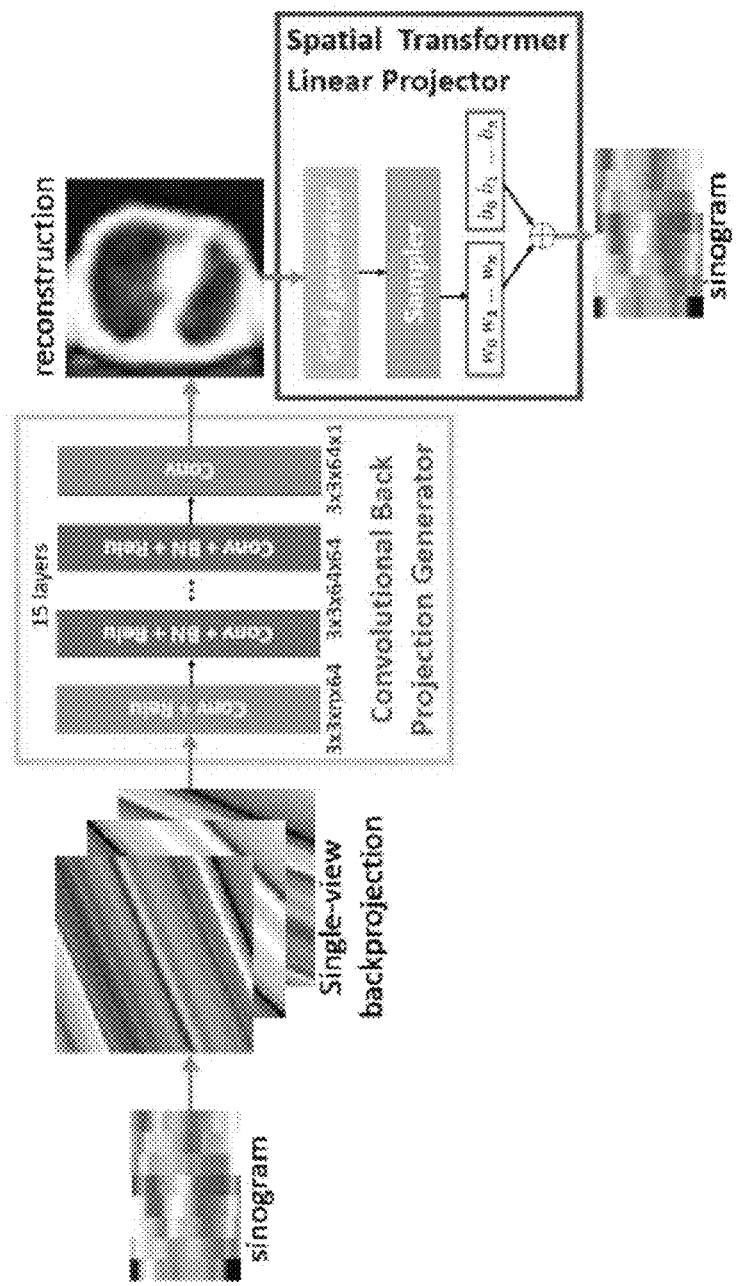
FIG. 29 provides a diagram showing an example framework of unsupervised sparse-view backprojection in accordance with the disclosed subject matter.

FIG. 29 shows an overview of our framework. Sinograms can be converted to single-view backprojections before feeding into a multi-layer CNN generator. The generator can predict the reconstruction from the sparsely measured sinograms, while the projector maps the reconstruction back to the original sinograms. The input and output of the network are both sparse-view sinograms. A sinogram is converted to single-view backprojections, which serve as input to the convolutional backprojection generator. The generator outputs the backprojection reconstruction. The spatial transformer linear projector takes the reconstruction and transformation angle as inputs and generates a sinogram. The projector also adjusts to sensor non-uniformity with trainable weights and biases.

Dataset and Framework: to assess the performance of the disclosed algorithm, a dataset with ground truth of reconstruction was required. So instead of using the disclosed simultaneous EEG-fMRI data, the disclosed algorithm was assessed using 43 human chest CT scans. The reason for using a CT dataset lies in that CT image reconstruction is a well known backprojection problem that has been explored for decades, so it's convenient to compare to widely used methods on CT data and easy to judge the performance.

The dataset was part of the Cancer Imaging Archive (TCIA). 2/4/8/16-angle sinograms were generated by applying the corresponding Radon transformation to each slice of the CT data with and without sensor non-uniformity respectively. Sensor non-uniformity was introduced by multiplying each projection pi with a weight wi and adding a bias bi. Both wi and bi are random numbers with a standard normal distribution. wi and bi are constants for different slices of the same scan. Assessing the disclosed algorithm on CT data can allow the expanded application of this algorithm to other backprojection applications.

Single-view Backprojections: the relationship between the data space S and its set of projections is defined as the Radon transformation:

$$\text{Radon}(S,\theta) = R_S(l(0),\theta) = \int_{-\infty}^{\infty}\int_{-\infty}^{\infty} S(x,y)\delta(l(\theta)-x\cos\theta - y\sin\theta)dxdy \text{ where } \delta(\cdot) \text{ is the Dirac delta function and } l(\theta) = x\cos\theta + y\sin\theta. \quad (11)$$

One projection pi as an integration of the data space S along a particular direction Oi, can be represented with Radon transform as $$\rho_i = \text{Radon}(S,\theta) \quad (12)$$

A sinogram, a standard data structure to store projections, can be defined as the m×n matrix made of n projections (p1, p2, p3, ..., pn) from different angles ($\theta_1, \theta_2, \theta_3, \ldots, \theta_n$). Backprojection tries to solve the inverse problem, namely to reconstruct the data S from the sinograms generated from its limited numbers of projections (p1, p2, p3, ..., pn).

Figure 30:
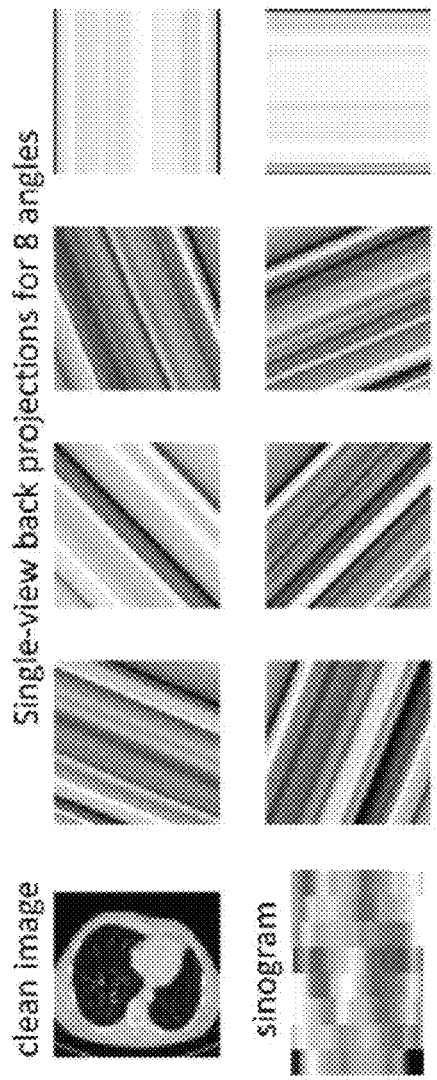
FIG. 30 provides images showing example high resolution CT images (upper left), its 8-angle projection sinogram (lower left), and its single-view backprojections (right) in accordance with the disclosed subject matter.

Instead of using sinograms directly as input to a CNN, single-view backprojections were constructed by performing single projection backprojection and stacking the backprojection results. An example of 8 angle single-view backprojections is shown in FIG. 30.

Convolutional Backprojection Generator: the stacked n (where n is the number of projections) single-view backprojections serve as the n-channel input to the convolutional backprojection generator.

The convolutional backprojection generator was composed of 17 convolution layers. Batch normalization was applied to all layers except for the first and last layers. ReLU activation functions were applied to all layers except the last layer. Each of the layers except the last uses 64 convolution kernels of size 3×3. The last layer has 1 kernel of size 3×3 to construct the backprojection prediction from all inputs.

Spatial Transformer Linear Projector: the backprojection reconstruction serves as input to an STN inspired linear projector to generate predicted sinograms. The projector applies the Radon transform of correspondent angles ($\theta_1, \theta_2, \theta_3, \ldots, \theta_n$) to the backprojection reconstruction to regenerate the sinogram prediction as in equation 13. To implement a differentiable Radon transformation that allows gradient-based back propagation, the spatial transformers was used. The grid generator transform the original regular spatial grid of the reconstruction to a sampling grid. The sampler produces the sampled transformed data from the reconstruction at the grid points. Then a trainable linear mapping, as in equation 14, is applied to each pi with different wi and bi, which compensates for possible sensor non-uniformity.

$$\hat{p}_i = \text{Radon}(\hat{S},\theta_i) \quad (13)$$

$$\hat{p}_i' = w_i\hat{p}_i + b_i \quad (14)$$

The objective function is given in equation (15). The mean squared error between the generated sinogram $\hat{p}' = (\hat{p}_1', \ldots, \hat{p}_n')$ and the sinogram ground-truth $P = (p_1, \ldots, p_n)$ were minimized. This ground-truth is different from the ground-truth, as the ground-truth is the sparse projections. We also include an l1-norm of predicted backprojection reconstruction S to impose a sparse reconstruction.

$$l(k,w,b) = \frac{1}{n}\sum_{k=1}^{n}\|p_i - \hat{p}_i'\|_2^2 + \alpha\|\hat{S}\|_1 \quad (15)$$

Result: to assess the performance of our unsupervised algorithm on the limited data, each model was trained and tested on the same subject's scan. The mean number of slices for each scan is 80.70±21.16. The performance of the disclosed algorithm was compared, and backprojection was filtered on 2/4/8/16-angle sinograms reconstruction with and without sensor non-uniformity. When testing without sensor non-uniformity, the weights wi=1 and bias bi=0 were fixed for the STN inspired projector.

Figure 31:
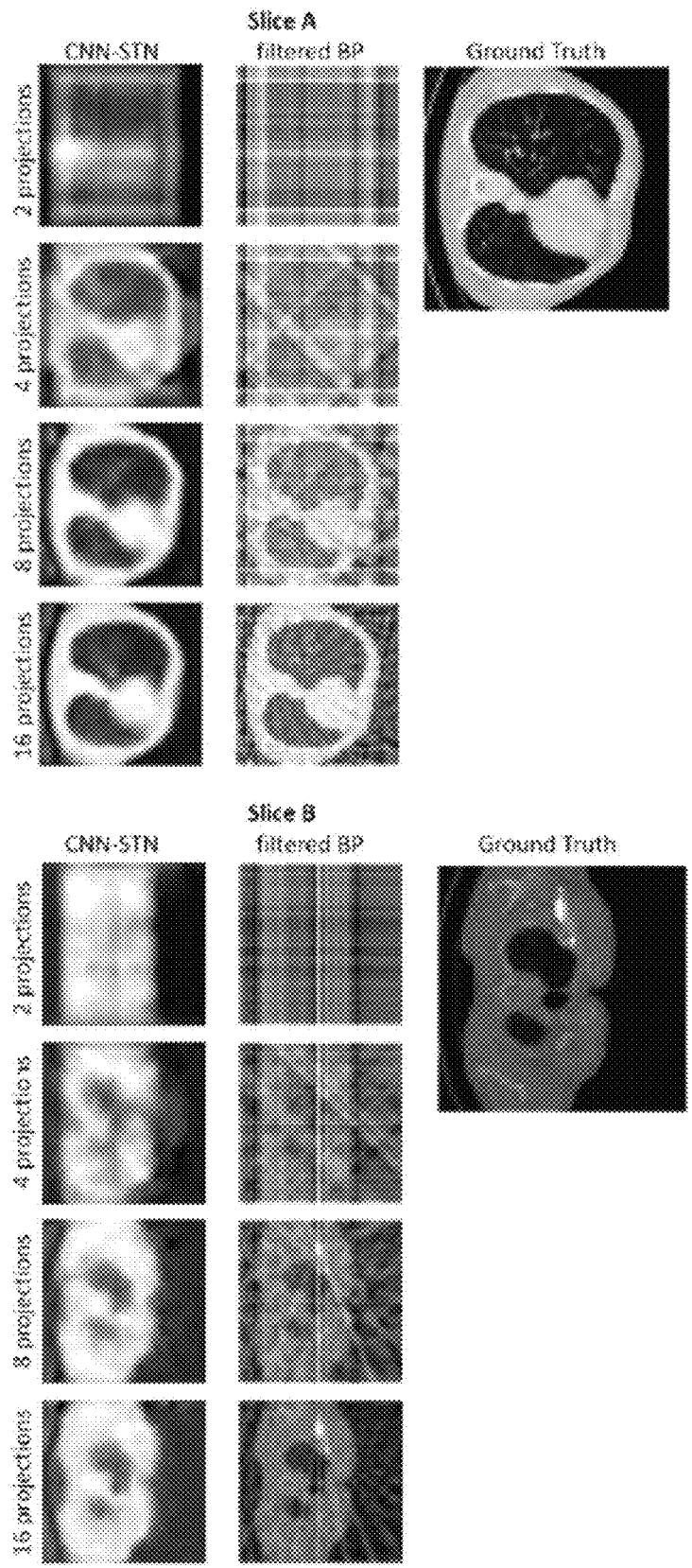
FIG. 31 provides images showing reconstruction results for the case of uniform sensors in accordance with the disclosed subject matter.

FIG. 31 shows results for two different slices given 2/4/8/16-angle projection reconstructions. Slices A and B are two example slices of a reconstructed chest CT scan. For each example slice, the left most column is the reconstruction result using the disclosed algorithm, the middle column is the reconstruction result using filtered backprojection and the right image is the ground truth. The disclosed algorithm was compared to filtered backprojection assuming sensor uniformity (i.e., fixed wi=1 and bi=0). In all cases, the disclosed algorithm performed better than filtered backprojection. The improved performance was especially apparent in sparse cases –2/4-angle projection reconstructions of filtered backprojection barely show any useful information while the disclosed algorithm can still provide meaningful results. To compare the performance in an objective way, the mean square error (MSE) of the reconstruction was calculated using the equation (16), where S stands for the ground truth image and S^ is the reconstruction. Reconstruction peak signal-to-noise ratio (PSNR) on top of MSE(shown in equation (17)) was calculated. The MAXs stand for the maximum possible pixel value of ground truth S.

$$MSE = \frac{1}{mn}\sum_{i=0}^{m-1}\sum_{j=0}^{n-1}\left[S(i,j)-\hat{S}(i,j)\right]^2 \quad (16)$$

$$PSNR = 20\log_{10}\left(\frac{MAX_S}{\sqrt{MSE}}\right) \quad (17)$$

For 2/4/8/16 angles of projections, the disclosed algorithm showed improved PSNR than filtered backprojection.

Figure 32:
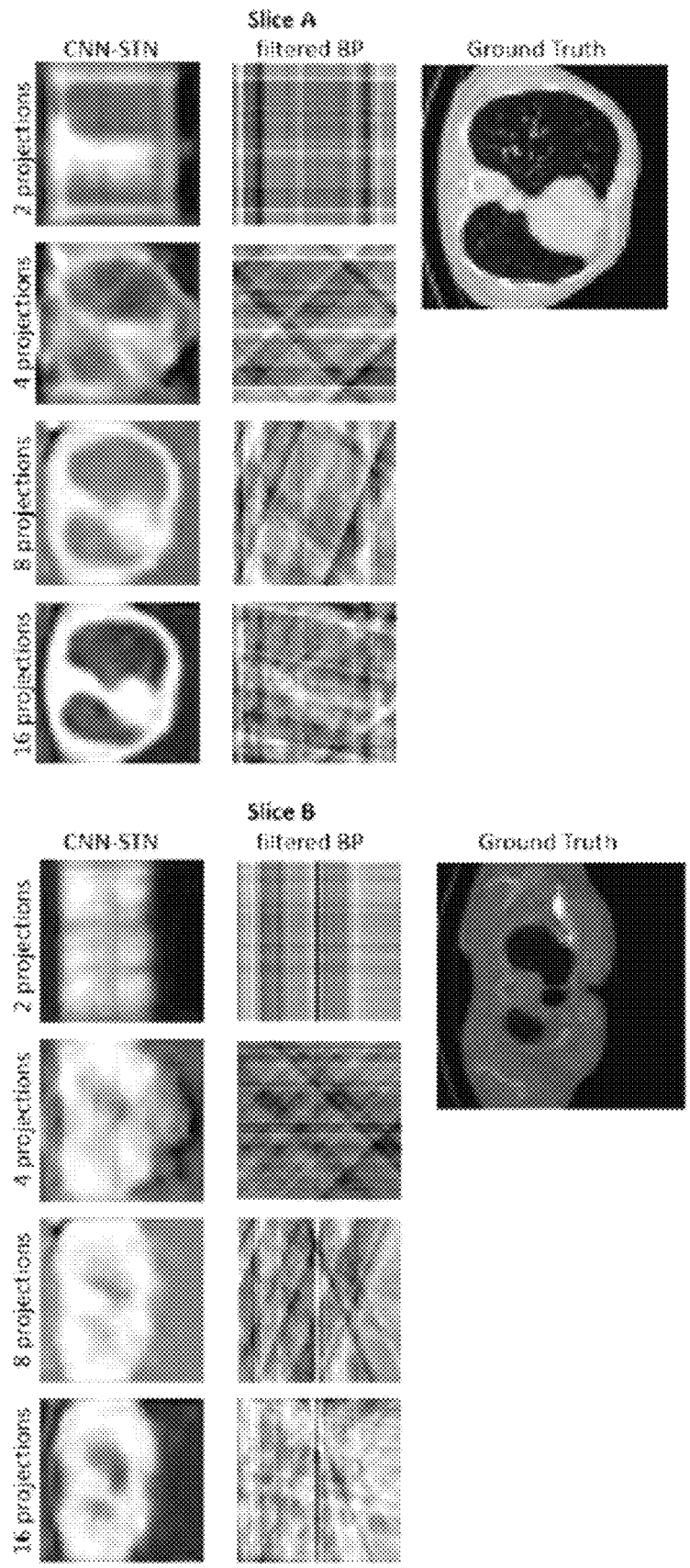
FIG. 32 provides images showing reconstruction results for the case of non-uniform sensors in accordance with the disclosed subject matter.
Figure 33B:
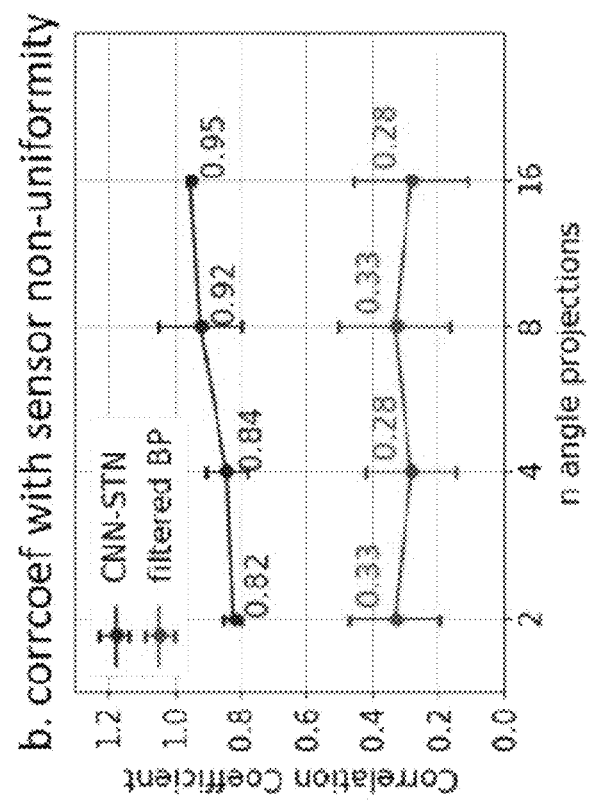
FIG. 33B provides a graph showing the reconstruction correlation coefficient of the disclosed algorithm and filtered backprojection non-uniform sensor in accordance with the disclosed subject matter.
Figure 33A:
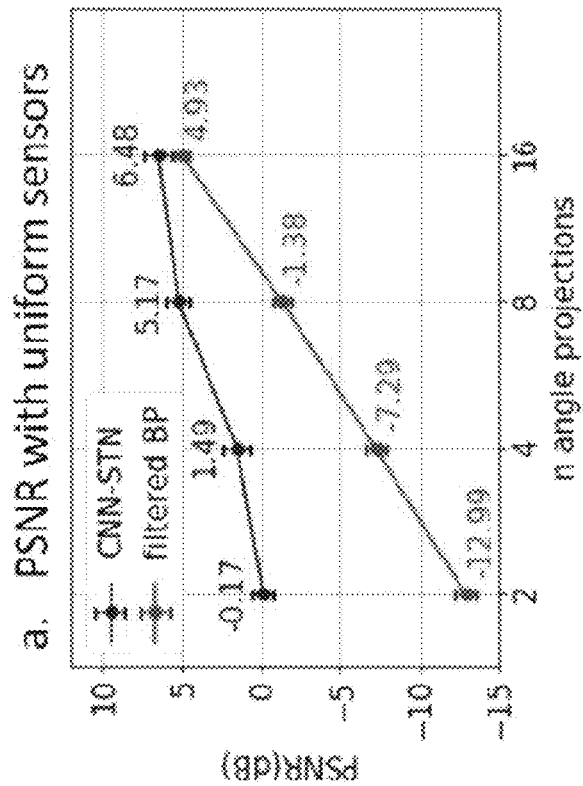
FIG. 33A provides a graph showing the reconstruction PSNR of the disclosed algorithm and filtered backprojection with uniform sensors in accordance with the disclosed subject matter.

FIG. 32 shows two slices' 2/4/8/16-angle projection reconstruction results for the disclosed algorithm compared with filtered backprojection for the case of sensor non-uniformity. Slices A and B are two examples slices of a reconstructed chest CT scan. For each example slice, the left most column is the reconstruction result using the disclosed algorithm, the middle column is the reconstruction result using filtered backprojection and the right image is the ground-truth. Filtered backprojection cannot adjust to sensor non-uniformity and shows strong artifacts. The disclosed algorithm can suppress the impact of sensor non-uniformity and provides reasonable reconstructions. Due to sensor non-uniformity, the intensity and contrast of the original image cannot be recovered, hence a PSNR comparison is meaningless. Instead, the correlation coefficient between ground-truth and reconstructed images was used as an evaluation metric of the reconstruction performance. FIGS. 33A-33B show the correlation coefficients of the disclosed algorithm and filtered backprojection. The disclosed algorithm outperformed the filtered backprojection, with performance continuing to improves as the number of projections acquired increases. This is not true for filtered backprojection, where performance does not improve with more projections when sensors are non-uniform.

An unsupervised backprojection algorithm was introduced using a generator-projector framework based on a CNN and STN. The results show improved performance of the disclosed algorithm than the conventional filtered backprojection algorithm. The deep learning models, with relatively few parameters as we have in the CNN and STN, can be applied to unsupervised tasks that have very limited training data.

With uniform sensors, when the number of projections increases, the performance of the disclosed algorithm increases more slowly than filtered backprojection. With dense projections, filtered backprojection still provides more accurate reconstruction results. However, the disclosed approach enables methods, which are limited in the number of projections or where sensor characteristic is arbitrary or non-uniform. This algorithm can be applied more broadly, for example, to applications when the sensors are sparse and non-uniform, and/or there is no ground-truth, as it is required in supervised learning. For example, radar and visual input based reconstruction have limited numbers of sensors/projections. Acquiring the ground-truth for training can be also expensive and can require human effort/labeling. Sensor non-uniformity can be common for these applications because multiple sensors are often used for different angles. A joint transcoding/prediction can allow the recovery of the latent source space. One of the difficulties can be the absence of ground-truth for the source space. In the disclosed system, the EEG predicted source space and fMRI predicted source space can be considered as two projections of the same source space. As the two modalities can yield different intensity scales of the source space predictions, a backprojection problem can be assessed with sensor non-uniformity.

Example 3: Unsupervised Transformational Backprojection for Simultaneous EEG-fMRI Super-Resolution Latent Neural Source Recovery The source space can be estimated with transcoders from both EEG and fMRI data. While a compromise in resolution enables feasible training and testing for the transcoder, recovery of a high spatio-temporal resolution latent sources estimates is also desired. The latent source space from fMRI can be up-sampled to only 2.86 Hz, which is of a substantially lower temporal resolution than the original 500 Hz sampling rate of the EEG. Likewise, latent sources estimated from EEG can be only expanded to a 3D space of size 15×18×15 voxels (with unit voxel size of 12 mm×12 mm×12 mm), while the original spatial resolution of acquired fMRI is of 2 mm×2 mm× 2 mm. To recover latent source space estimates at the full original resolutions of the neuroimaging data, the two source spaces were fused through backprojection.

A variance of transformational backprojector was used to combine the transcoded EEG and fMRI data to achieve the integrated source space with EEG's temporal resolution and fMRI's spatial resolution. As the latent source space estimated from fMRI still has higher spatial resolution and lower temporal resolution compared to the latent source space estimated from EEG, the latent source space estimated from fMRI was considered as a projection of the integrated latent source space along the time dimension, while the latent source space estimated from EEG is considered as a projection along the spatial dimension.

The disclosed subject matter can provide a method to solve unsupervised very sparse view back projection problem and tested its performance on very sparse view CT images. The disclosed subject matter can also provide techniques for fusing the source space estimated from EEG and the source space estimated from fMRI, which can be considered as a 2-projection backprojection problem.

Figure 34:
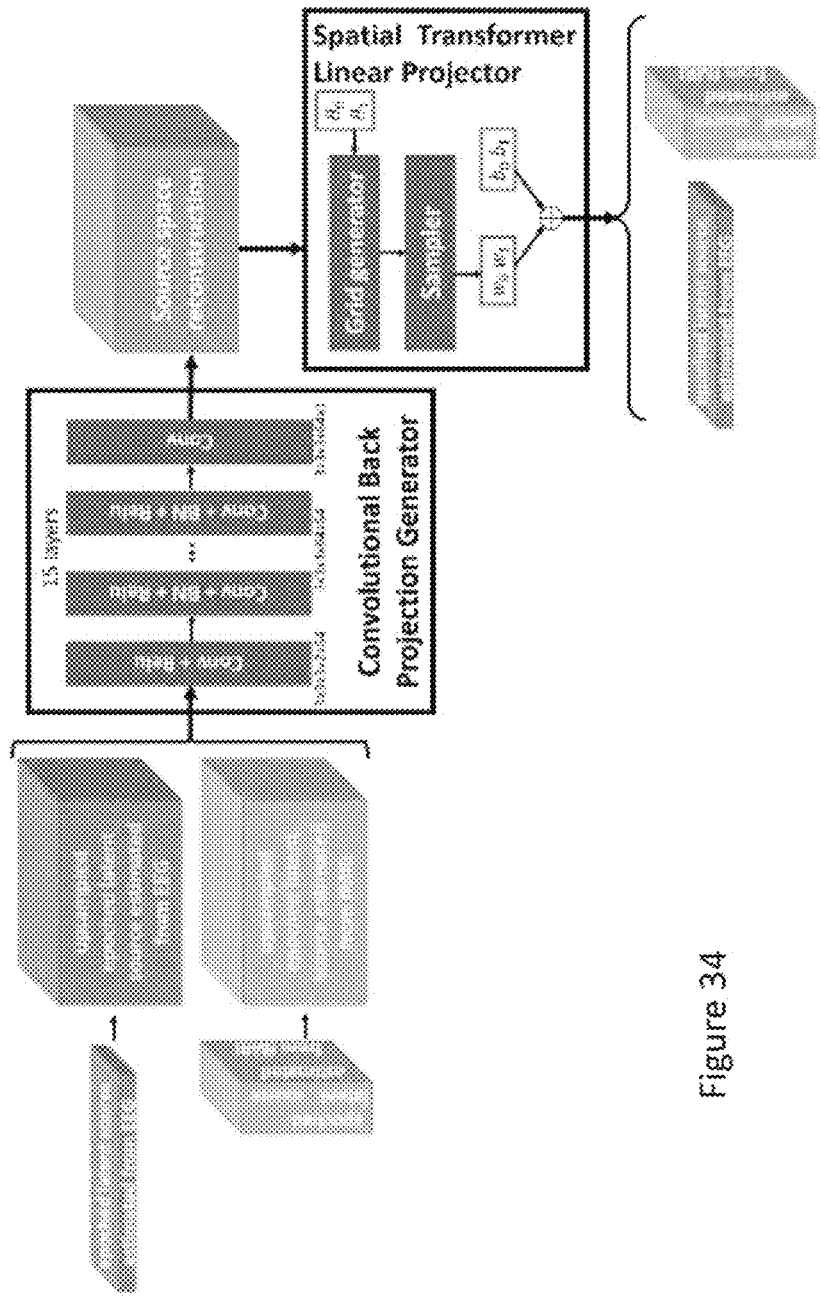
FIG. 34 provides a diagram showing a framework of the transformational back projector in accordance with the disclosed subject matter.

The modified model was used to fuse the two source space. The data was epoched similar to EEG data, and the brain dynamic within 800 ms after the stimuli onset was observed. Given a 6×6×6×175 portion of the latent source space, its field of view was 12 mm×12 mm×12 mm×0.35s. When projected to the temporal dimension, it can collapse to one time point of size 6×6×6×1. This is equivalent to one volume of the latent source space estimated from fMRI. When projected to the spatial dimensions, the source space can collapse to one time series of length 175, which can be considered as one voxel in the latent source space estimated from EEG. Reversing this process by solving the 2-direction back-projection problem, the latent source space estimated from EEG and the latent source space estimated from fMRI were combined to reconstruct the latent source space with the desired spatial and temporal resolution. FIG. 34 shows an illustration of our framework for latent source space reconstruction with simultaneous EEG-fMRI data.

Furthermore, the backprojector on epoched data was applied. The up-sampled epoched source space estimated from EEG and epoched source space estimated from fMRI served as two channels of input data, and represented projections from an epoched integrated source space.

Figure 12A:
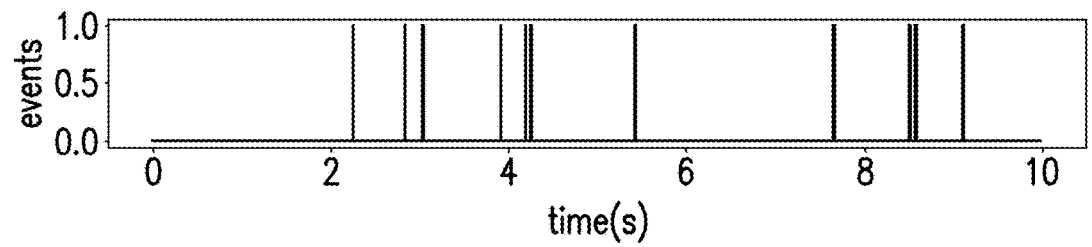
FIG. 12A provides a graph showing an example of epoching jittered events (random starting time of stimuli).
Figure 12B:
FIG. 12B provides a graph showing an example of epoching jittered events (source time series).
Figure 12C:
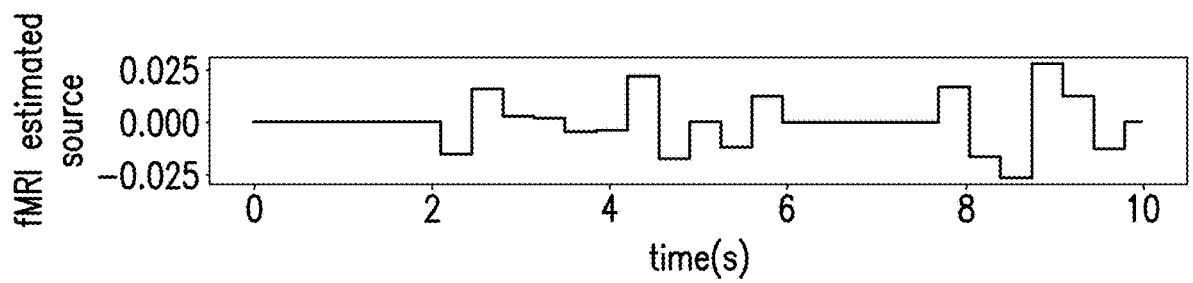
FIG. 12C provides a graph showing an example of epoching jittered events (fMRI estimated source time series) in accordance with the disclosed subject matter.
Figures 13A, 13B:
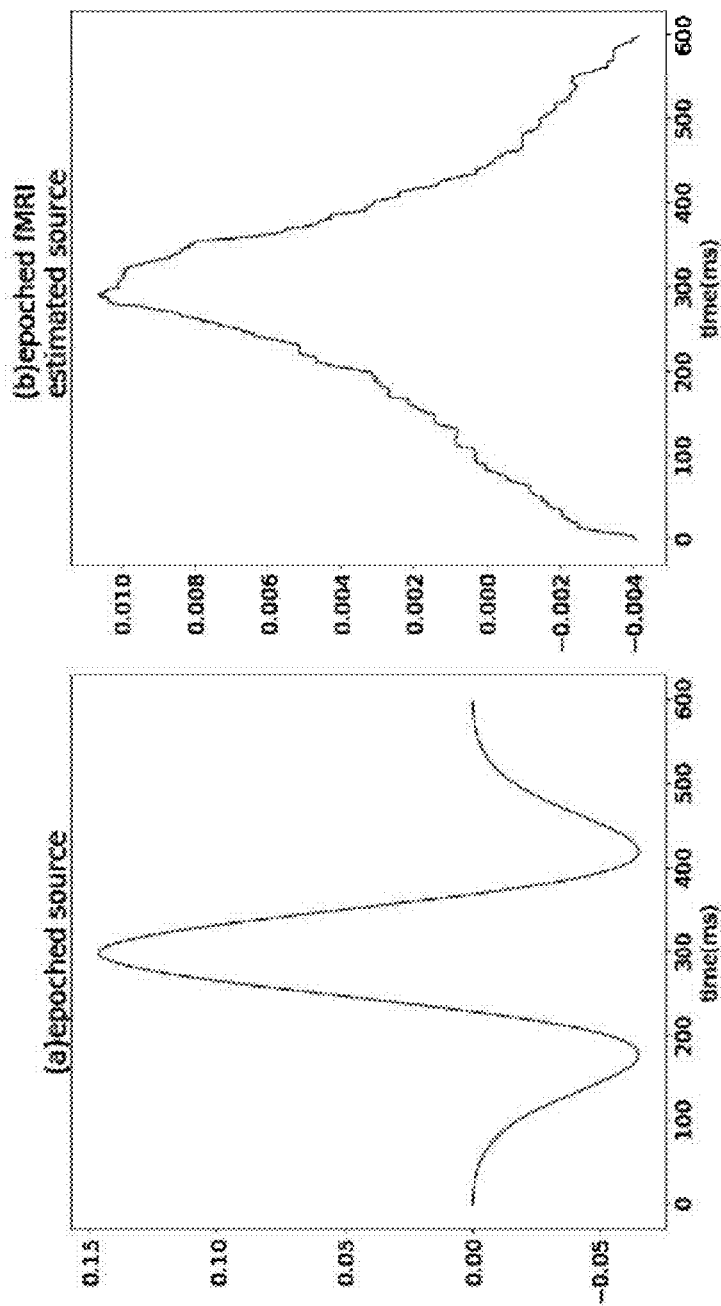
FIG. 13A provides a graph showing an example of epoching jittered events (source impulse response).
FIG. 13B provides a graph showing an example of epoching jittered events (epoched fMRI estimated source).

When stimuli are presented randomly, epoching the data at a low sampling rate can achieve high temporal resolution and solve the temporal backprojection problem for source space estimated from fMRI. In an illustrative example, as shown in FIG. 12, 200 random stimuli spanning a time length of 200 s were generated and convolved with a source impulse response as shown in FIG. 13A. The resulting time series of the simulated source at 500 Hz is shown in FIG. 12. Given the fMRI estimated space has a temporal resolution 2.86 Hz, an underlying 500 Hz source space is projected in the temporal direction for every 175 points. The simulated 2.86 Hz fMRI estimated source signal is thus shown in FIG. 12 (bottom row).

FIGS. 13A-13B show the original designed source impulse response (13A) compared with epoched fMRI estimated source (13B), which is an estimate of the source impulse response. Due to the jittering nature of the stimuli starting time, the epoched fMRI estimated source signal (13B) has a finer temporal resolution and resembles the actual source impulse response in FIG. 13A.

With each time point considered as one data sample, every epoch has 1200 ms (i.e., 600 time points), starting from 350 ms before to 850 ms after the stimulus. A CNN was used to backproject to the epoched integrated source space, then a projector is applied to the data to project the estimated integrated source space back to the source space estimated from fMRI in the direction $\theta_0$ and source space estimated from EEG in direction $\theta_1$. As temporal backprojection is achieved by epoching, only a spatial transformation was applied. Thus the CNN includes only spatial convolution layers in this example. The weights $\omega_0$, $\omega_1$ and biases $b_0$, $b_1$ are fit to model possible scale and baseline difference between the latent source space estimated from fMRI and the latent source space estimated from EEG.

Figure 35:
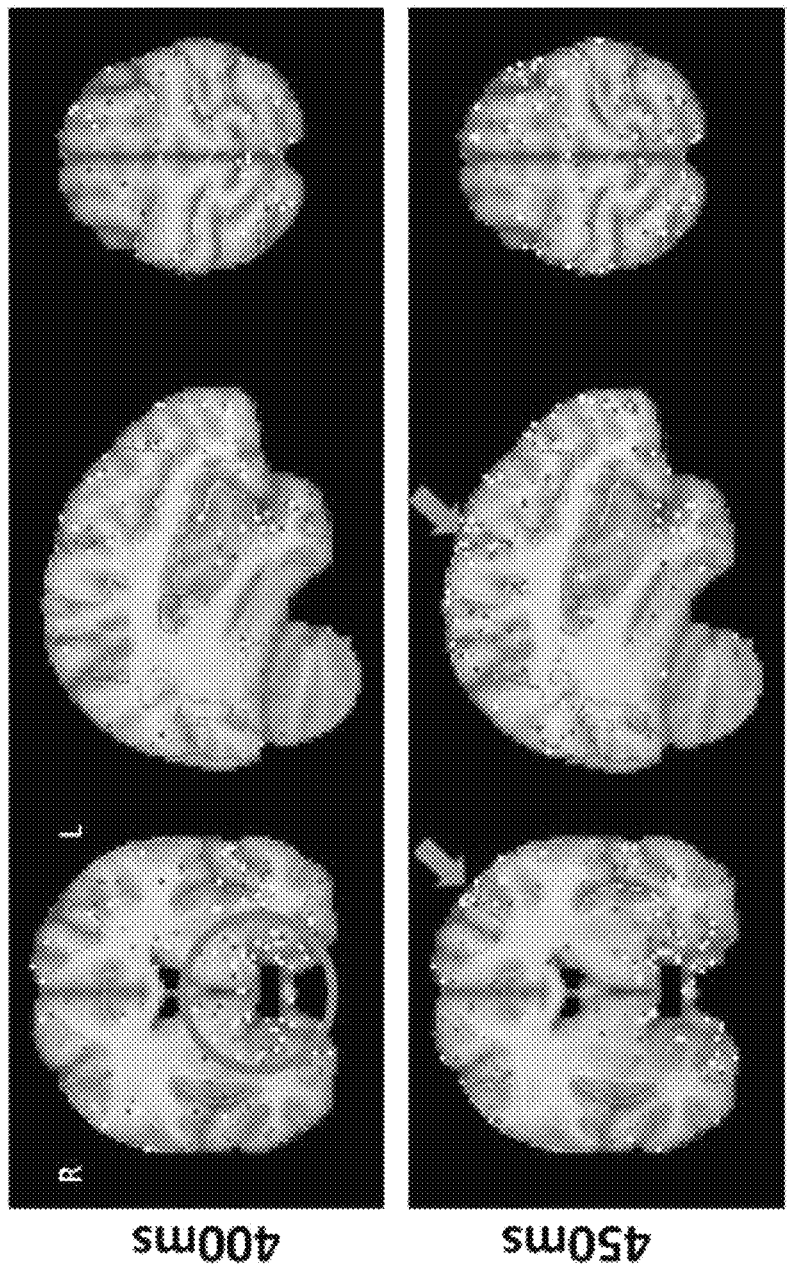
FIG. 35 provides images showing the EEG-fMRI integrated source space for oddball stimuli epochs in accordance with the disclosed subject matter.

FIG. 35 shows representative results of the integrated source space. The figure shows group-level source activation maps of two volumes at 400 ms and 450 ms post-stimulus. The images in FIG. 35 are sources for two time points leading up to a response (right handed button press) for oddball epochs. Source strength is indicated by color (yellow is stronger than red). The green circle highlights subcortical regions that are part of the motor system, including the putamen, globus pallidus and elements of the basal ganglia associated with voluntary movement. The blue arrows point to activity in the motor cortex that is localized to the right hand (contralateral motor cortex). The latent source space has a spatial resolution of 2 mm×2 mm×2 mm and temporal resolution of 500 Hz. The integrated source space exhibits activation patterns associated with an auditory oddball task. For instance, at approximately 450 ms after the onset of the oddball stimulus, activation is seen in the primary motor cortex specifically related to finger movement. Preceding this activation, at 400 ms is strong activation in subcortical regions that are part of the motor system. Thus, cortical and sub-cortical latent sources were resolved at millisecond time scale, that are consistent with the task, which cannot be done without integrated information from EEG and fMRI.

The transformational backprojector was modified so that it can fuse two modalities into a latent source space without compromising the high temporal resolution of EEG or the high spatial resolution of fMRI.

The fused source space is, in itself, a new neuroimaging data representation, having fMRI's spatial resolution (2 mm×2 mm×2 mm) and EEG's temporal resolution (500 Hz). This is a resolution never achieved for in vivo non-invasive human brain imaging. This model, therefore, has the potential of serving as a new tool for human neuroimaging—i.e., it yields a 3D data volume at a high temporal resolution.

The fused source space is of fMRI's spatial resolution (2 mm×2 mm×2 mm) and EEG's temporal resolution of 500 Hz. It shows not only which brain area is activated at each millisecond, even the path the brain activity is traveling through the brain is really clear. At this point, a brain dynamic causal model is straightforward from observing the source space.

Unless otherwise defined, all technical and scientific terms used herein have the same meaning as commonly understood by one of ordinary skill in the art. In case of conflict, the present document, including definitions, will control. Certain methods and materials are described below, although methods and materials similar or equivalent to those described herein can be used in the practice or testing of the presently disclosed subject matter. All publications, patent applications, patents, and other references mentioned herein are incorporated by reference in their entirety. The materials, methods, and examples disclosed herein are illustrative only and not intended to be limiting.

While it will become apparent that the subject matter herein described is well calculated to achieve the benefits and advantages set forth above, the presently disclosed subject matter is not to be limited in scope by the specific embodiments described herein. It will be appreciated that the disclosed subject matter is susceptible to modification, variation, and change without departing from the spirit thereof. Those skilled in the art will recognize or be able to ascertain using no more than routine experimentation, many equivalents to the specific embodiments described herein. Such equivalents are intended to be encompassed by the following claims.

What is claimed is:

1. A system for hierarchical deep transcoding, comprising: a processor configured to
receive a functional magnetic resonance imaging (fMRI) data and/or an extracranial electroencephalogram (EEG) data, wherein the fMRI data and the EEG data are simultaneously acquired; and
reconstruct a latent source space from the fMRI data and/or the EEG data by decoding the EEG data and/or the fMRI data to the latent source space, wherein the processor is configured to transcode the EEG data to an fMRI signal or the fMRI data to an EEG signal.

2. The system of claim 1, wherein the processor is further configured to
train a group-level model with a plurality of EEG and fMRI signals obtained from at least two subjects to determine an intermediate spatial/temporal resolution of the plurality of EEG and fMRI signals; and
generate estimates of the latent source space of the intermediate solution from the EEG and fMRI signals based on the trained group-level model, wherein the interpolated EEG and fMRI signals have a same intermediate resolution for training the group-level model.

3. The system of claim 2, wherein the processor is configured to
train a subject-level model with the group-level latent space estimates from the EEG and fMRI signals to determine a spatial/temporal resolution of the subject-level latent source space, wherein the group-level latent space estimates are epoched to achieve a 3D event related potential (ERP) representation; and
determine the spatial/temporal resolution of the latent source space using the subject-level model.

4. The system of claim 3, wherein the epoched signals are sliced in a spatial and temporal direction.

5. The system of claim 4, wherein the group-level model and the subject-level model are a cyclic convolutional transcoder.

6. The system of claim 4, wherein the EEG data is transcoded to an fMRI signal and/or the fMRI data is transcoded to an EEG signal based on the spatial/temporal resolution of the latent source space determined by the group-level model and the subject-level model.

7. The system of claim 5, wherein the cyclic convolutional transcoder comprises an fMRI decoder, an fMRI encoder, an EEG decoder, an EEG encoder, or combinations thereof.

8. The system of claim 7, wherein the fMRI decoder decodes the latent source space from an fMRI encoding, and the EEG decoder decodes the latent source space from an EEG encoding.

9. The system of claim 7, wherein the fMRI encoder encodes the latent source space into an fMRI encoding, and the EEG encoder encodes the latent source space into an EEG encoding.

10. The system of claim 7, wherein the fMRI decoder and the fMRI encoder comprise temporal convolutional layers.

11. The system of claim 7, wherein the EEG decoder and the EGG encoder comprise spatial convolutional layers.

12. The system of claim 1, wherein the processor is configured to generate a map based on the reconstructed the EEG signal and/or the fMRI signal.

13. The system of claim 1, wherein the processor is configured to estimate a hemodynamic impulse response (RF) function; and
forward or inverse a head conductivity model from the fMRI and EEG data, wherein the conductivity model includes a leadfield matrix.

14. A method for hierarchical deep transcoding, comprising
receiving a functional magnetic resonance imaging (fMRI) data and/or an extracranial electroencephalogram (EEG) data, wherein the fMRI data and the EEG data are simultaneously acquired;
reconstructing a latent source space from the EEG data and/or the fMRI data by decoding the EEG data and the fMRI data to the latent source space;
training a group-level model with a plurality of EEG and fMRI signals obtained from at least two subjects to determine an intermediate spatial/temporal resolution of the plurality of EEG and fMRI signals; and
generating estimates of the latent source space of the intermediate resolution from EEG and fMRI signals based on the trained group-level model, wherein the interpolated EEG and fMRI signals have a same intermediate resolution for training the group-level model.

15. The method of claim 5, further comprising
training a subject-level model with the group-level latent space estimates from the EEG and fMRI signals to determine a spatial/temporal resolution of the latent source space, wherein the ground-level latent space estimates are epoched to achieve a 3D event related potential (ERP) representation; and
determining the spatial/temporal resolution of the latent source space using the subject-level model.

16. The method of claim 15, wherein the EEG data is transcoded to an fMRI signal or the fMRI data is transcoded to an EEG signal based on the spatial/temporal resolution of the latent source space determined by the group-level model and the subject-level model.

17. The method of claim 16, further comprising generating a map based on the reconstructed the EEG signal and/or the fMRI signal, wherein the map comprises an activation map, a Z-statistic map, or combinations thereof.

18. The method of claim 14, further comprising
estimating a hemodynamic impulse response (RF) function; and
forwarding or inversing a head a conductivity model from the fMRI and EEG data, wherein the conductivity model includes a leadfield matrix.

* * * * *